(12) United States Patent
Rodrigo-Gomez et al.

(10) Patent No.: US 11,278,857 B2
(45) Date of Patent: Mar. 22, 2022

(54) POLYMERIC CAPSULES

(71) Applicant: The Procter & Gamble Company, Cincinnati, OH (US)

(72) Inventors: Raul Rodrigo-Gomez, Brussels (BE); Steven Daryl Smith, Cincinnati, OH (US); Yousef Georges Aouad, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 19 days.

(21) Appl. No.: 16/851,133

(22) Filed: Apr. 17, 2020

(65) Prior Publication Data

US 2020/0330951 A1   Oct. 22, 2020

Related U.S. Application Data

(60) Provisional application No. 62/835,008, filed on Apr. 17, 2019.

(51) Int. Cl.
 *B01J 13/14* (2006.01)
 *C11B 9/00* (2006.01)

(52) U.S. Cl.
 CPC ............. *B01J 13/14* (2013.01); *C11B 9/00* (2013.01)

(58) Field of Classification Search
 CPC .................................. B01J 13/14; C11B 9/00
 See application file for complete search history.

(56) References Cited

U.S. PATENT DOCUMENTS

| | | |
|---|---|---|
| 5,278,106 A | 1/1994 | Nakashima |
| RE45,538 E | 6/2015 | Smets |
| 9,415,530 B2 | 8/2016 | Fukuda |
| 2004/0251569 A1 | 12/2004 | Matsubara |
| 2007/0136328 A1 | 6/2007 | Carro |
| 2007/0202063 A1 | 8/2007 | Dihora |
| 2008/0061459 A1 | 3/2008 | Nakajima |
| 2008/0305982 A1 | 12/2008 | Smets |
| 2009/0023189 A1 | 1/2009 | Lau |
| 2009/0120526 A1 | 5/2009 | Berktold |
| 2011/0008427 A1 | 1/2011 | Biggs |
| 2011/0152147 A1 | 6/2011 | Smets |
| 2011/0268802 A1 | 11/2011 | Dihora |
| 2011/0294715 A1 | 12/2011 | Smets |
| 2011/0306116 A1 | 12/2011 | Jin |
| 2012/0152268 A1 | 6/2012 | York |

(Continued)

FOREIGN PATENT DOCUMENTS

| | | |
|---|---|---|
| KR | 20150100309 A | 9/2015 |
| WO | 2014104369 A1 | 3/2014 |

(Continued)

OTHER PUBLICATIONS

Cheng et al., "Preparation of monodisperse poly(N-isopropylacrylamide) microspheres and microcapsules via Shirasu-porous-glass membrane emulsification", Science Direct, Desalination 234, 2008, pp. 184-194.

(Continued)

*Primary Examiner* — Arrie L Reuther
(74) *Attorney, Agent, or Firm* — James E Oehlenschlager

(57) ABSTRACT

A population of capsules can include a plurality of capsules, the capsules can include a core including a benefit agent, and a polymeric shell surrounding the core. The population of capsules can have a delta fracture strength percentage of about 15% to about 230% and a shell thickness of about 20 nm to about 400 nm.

26 Claims, 45 Drawing Sheets

(56) References Cited

U.S. PATENT DOCUMENTS

| | | |
|---|---|---|
| 2014/0079747 A1 | 3/2014 | Dihora |
| 2014/0342972 A1 | 11/2014 | Smets |
| 2016/0184196 A1 | 6/2016 | Baxter |
| 2017/0002301 A1 | 1/2017 | Dihora |
| 2017/0002302 A1 | 1/2017 | Dihora |

FOREIGN PATENT DOCUMENTS

| | | |
|---|---|---|
| WO | WO2015067557 A1 | 5/2015 |
| WO | WO2017058875 A1 | 4/2017 |
| WO | WO2018169531 A1 | 9/2018 |

OTHER PUBLICATIONS

Database WPI, week 201566, Thompson Scientific, London GB, AN 2015-53862D, XP002794945.
EPO Search Report, U.S. Appl. No. 19/169,901, dated Oct. 23, 2019, 9 pgs.
EPO Search Report, U.S. Appl. No. 19/169,905, dated Oct. 8, 2019, 9 pgs.
EPO Search Report, U.S. Appl. No. 19/169,909, dated Oct. 14, 2019, 9 pgs.
Jyothi et al, "Microencapsulation techniques, factors influencing encapsulation efficiency", Journal of Microencapsulation, 27:3, pp. 187-197.
Thompson et al., "Colloidosomes: Synthesis, properties and applications", Journal of Colloid and Interface Science, 447, 2015, pp. 217-228.
Vladisavljevic et al., "Recent developments in manufacturing emulsions and particulate products using membranes", Advances in Colloid and Interface Science, vol. 113, No. 1, Mar. 17, 2005, pp. 1-20.
Cayer, "Polymer-based Functional Particulates: Design, Syntheses and Applications", Nov. 11, 2014, XP 055249238, 44pgs.
Database WPI, week 201566, Thompson Scientific, London GB, AN 2015-53862D, XP002799564.
International Search Report and Written Opinion, U.S. Appl. No. 19/169,901, dated Jul. 22, 2020, 16 pgs.
International Search Report and Written Opinion, U.S. Appl. No. 19/169,909, dated Jun. 29, 2020, 13 pgs.
International Search Report and Written Opinion, U.S. Appl. No. 19/169,905, dated Jun. 19, 2020, 14 pgs.
All Office Actions; U.S. Appl. No. 16/851,129, filed Apr. 17, 2020.
All Office Actions; U.S. Appl. No. 16/851,136, filed Apr. 17, 2020.

# POLYMERIC CAPSULES

FIELD OF THE DISCLOSURE

The disclosure relates to capsules and methods of making capsules for the transfer and triggered release of benefit agents, and more particularly to capsules having narrow distributions of capsule size and/or fracture strength.

BACKGROUND

Encapsulation is a process where droplets of liquids, particles of solids or gasses are enclosed inside a solid shell. The core material is then mechanically separated from the surrounding environment (Jyothi et al., *Journal of Microencapsulation*, 2010, 27, 187-197). Encapsulation technology is attracting attention from various fields of science and has a wide range of commercial applications for different industries. Overall, capsules are capable of one or more of (i) providing stability of a formulation or material via the mechanical separation of incompatible components, (ii) protecting the core material from the surrounding environment, (iii) masking or hiding an undesirable attribute of an active ingredient, (iv) controlling or triggering the release of the active ingredient to a specific time or location. All of these attributes can lead to an increase of the shelf-life of several products and a stabilization of the active ingredient in liquid formulations, as well as tailored delivery of the encapsulated formulation which can improve efficacy and/or efficiency.

Encapsulation can be found in areas such as pharmaceuticals, personal care, textiles, food, coatings, fabric care, home care, construction, and agriculture. In addition, the main challenge faced by encapsulation technologies in real-world commercial applications is that a complete retention of the encapsulated active within the capsule is required throughout the whole supply chain, until a controlled or triggered release of the core material is applied (Thompson et al., *Journal of Colloid and Interface Science*, 2015, 447, 217-228).

SUMMARY

In accordance with embodiments, a method of making capsules that include a core surrounded by a polymeric shell, can include dispersing droplets of a disperse-phase in a continuous phase by passing the disperse phase through a plurality of holes in a membrane, from a first side of the membrane to a second side of the membrane and into the continuous phase, while the continuous phase is flowed across the second side of the membrane and the membrane is mechanically moved. The disperse phase can include a polymer precursor, a process aider, and a benefit agent, and the continuous phase includes water. In the method, upon exiting the plurality of holes on the second side of the membrane, the disperse phase is formed into droplets of disperse phase. The method can further include exposing the dispersion of droplets of disperse phase in the continuous phase under conditions sufficient to initiate polymerization of the polymer precursor within the droplets of disperse phase. The polymer precursor becomes insoluble in the disperse phase and migrates to the interface between the disperse phase and the continuous phase, while the benefit agent remains in the core after polymerization. In embodiments, a stabilizer system is present in one or both of the disperse phase and the continuous phase, one or both of the disperse phase and the continuous phase comprises an initiator. In embodiments, the polymer precursor is soluble in the disperse phase and comprises a multifunctional ethylenically unsaturated monomer.

In accordance with embodiments, a population of capsules can include a plurality of capsules, each capsule can include a core including a benefit agent, and a polymeric shell surrounding the core. The population of capsules can have a delta fracture strength percentage of about 15% to about 230% and a shell thickness of 20 nm to 400 nm.

In accordance with embodiments, a population of capsules can include a plurality of capsules, each capsule can include a core including a benefit agent, and a polymeric shell surrounding the core. The population of capsules can have a number population diameter coefficient of variation of 10% to 100% and the capsules have a mean shell thickness of 20 nm to 400 nm.

In accordance with embodiments, a capsule or capsules can include a core containing a benefit agent, and a polymeric shell surrounding the core. In embodiments, the capsules can have a mean weight core-shell ratio of greater than about 90 to 10. In embodiments, the capsules can have a mean weight core-shell ratio of about 95 to 5. In embodiments, the capsules can have a mean effective volumetric core-shell ratio of greater than about 90 to 10. In embodiments, the capsules can have a mean effective volumetric core-shell ratio of greater than about 95 to 5.

BRIEF DESCRIPTION OF THE DRAWINGS

While the specification concludes with claims particularly pointing out and distinctly claiming the subject matter presented herein, it is believed that the disclosure herein will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION

Figure 1:
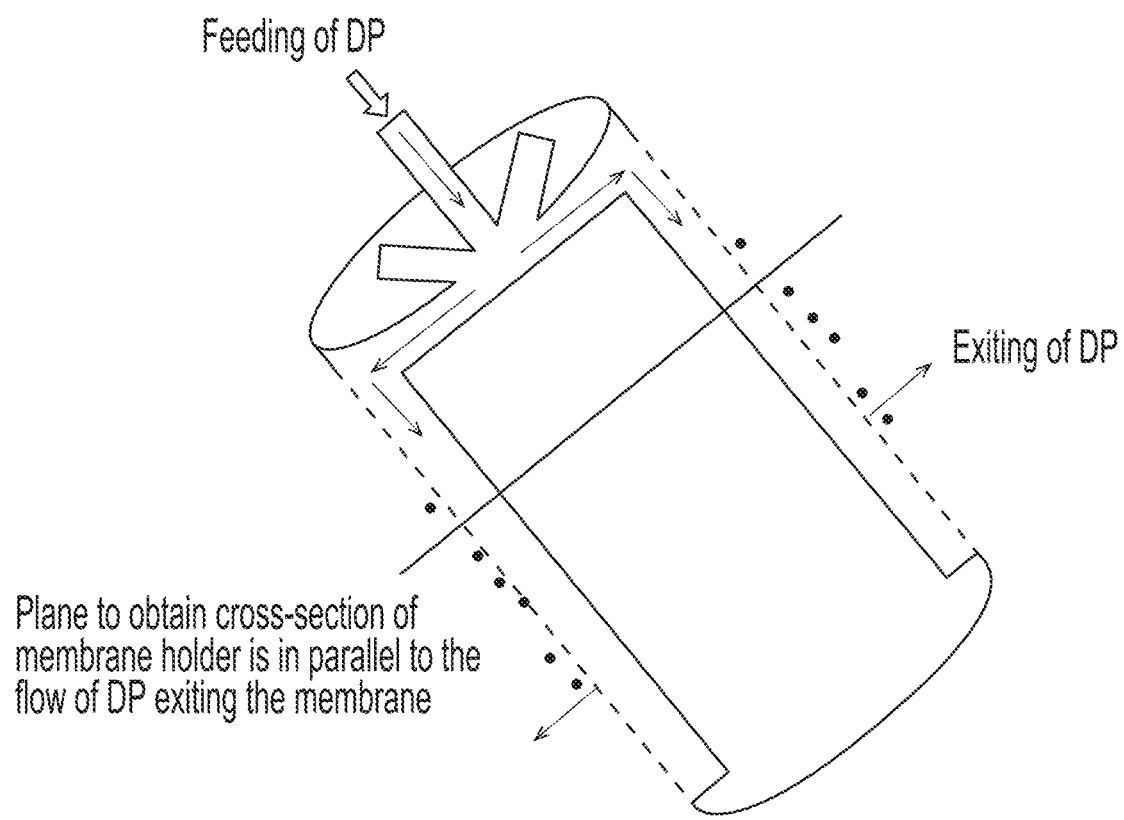
FIG. 1 is a schematic illustration of an embodiment of a cylindrical membrane device for use in methods in accordance with embodiments of the disclosure.

Provided herein are capsules having a polymeric shell surrounding a core and methods of making capsules. Capsules in accordance with embodiments of the disclosure can include a benefit agent. In embodiments, the capsules can be incorporated into a formulated product for release of the benefit agent upon capsule rupture. Various formulated products having capsules are known in the art and capsules in accordance with the disclosure can be used in any such products. Examples include, but are not limited to, laundry detergent, hand soap, cleaning products, lotions, fabric enhancers, skin care products, beauty care products, and other cosmetic products.

In various embodiments, capsules are produced having a narrow distribution of capsule size. In various embodiments, capsules can have a delta fracture strength percentage, as discussed in more detail below, of 15% to 230% and a shell thickness of about 20 nm to about 400 nm. In various embodiments, the capsules have a mean diameter of greater than 1 µm. In embodiments, each of the capsules has a diameter greater than 1 µm. In various embodiments, the capsules can have a number population diameter coefficient of variation of 10% to 100%, and a mean shell thickness of about 20 nm to about 400 nm. In embodiments, the capsules can have a mean weight core-shell ratio of greater than about 90 to 10. In embodiments, the capsules can have a mean weight core-shell ratio of about 95 to 5. In embodiments, the capsules can have a mean effective volumetric core-shell ratio of greater than about 90 to 10. In embodiments, the capsules can have a mean effective volumetric core-shell ratio of greater than about 95 to 5.

In embodiments, the capsules can have a delta fracture strength percentage, as discussed in more detail below, of 15% to 350%. In embodiments, the capsules can have a delta fracture strength percentage, as discussed in more detail below, of 15% to 230%. In any of the embodiments, the capsules can have a shell thickness of about 20 nm to about 400 nm. In any of the embodiments, the capsules can have a number population diameter coefficient of variation of about 10% to about 100%.

In embodiments, the population of capsules can include a delta fracture strength percentage of about 15% to about 230% and a shell thickness of about 20 nm to about 400 nm. In embodiments, the population of capsules can include a number population diameter coefficient of variation of about 10% to about 100% and a shell thickness of about 20 nm to about 400 nm. In embodiments, the population of capsules can have a delta fracture strength percentage, as discussed in more detail below, of about 15% to about 230%. In embodiments, the population of capsules can have a shell thickness of about 20 nm to about 400 nm. In embodiments, the population of capsules can have a number population diameter coefficient of variation of about 10% to about 100%.

The foregoing represents example embodiments of combinations of capsule properties. These and various additional properties are further described in detail below. It should be understood herein that other combinations of such properties are contemplated herein and can be any one or more of such properties described in the following paragraphs can be used in various combinations.

In various embodiments, a capsule is provided as a single capsule, as part of a population of capsules, or as a part of a plurality of capsules in any suitable number. Reference to individual capsule features, parameters and properties made herein shall be understood to apply to a plurality of capsules or population of capsules. It should be understood herein that such features and associated values can be mean values for a plurality or population of capsules, unless otherwise specified herein.

In any of the embodiments herein, the core can include a benefit agent. In various embodiments, the core can be liquid.

In embodiments, a capsule or a population of capsules can have a mean weight core-shell ratio of at least about 80 to 20, 85 to 15, 90 to 10, 95 to 5, 98 to 2, 99 to 1, 99.5 to 0.5, 99.9 to 0.1, or 99.99 to 0.01. For example, a capsule or a population of capsules can have a mean weight core-shell ratio of 80 to 20, 85 to 15, 90 to 10, 95 to 5, 98 to 2, 99 to 1, 99.5 to 0.5, 99.9 to 0.1, or 99.99 to 0.01. In embodiments, the population of capsules can have a mean weight core-shell ratio of about 80 to 20 to about 99.9 to 0.1, or about 90 to 10 to about 99.9 to 0.1, or about 95 to 5 to about 99.99 to 0.01, or about 97 to 3 to about 99.99 to 0.01, or about 95 to 5 to about 99.5 to 0.5. In embodiments, the entire population of capsules can have a mean weight core-shell ratio of at least 80 to 20, or at least 90 to 10 or at least 95 to 5, or at least 97 to 3. As used herein, a weight core-shell ratio refers to the ratio of weight percent based on the total weight of the capsule of core material to shell material.

In embodiments, a capsule or a population of capsules can have a mean effective volumetric core-shell ratio of at least 80 to 20, 85 to 15, 90 to 10, 95 to 5, 98 to 2, 99 to 1, 99.5 to 0.5, 99.9 to 0.1, or 99.99 to 0.01. For example, a capsule or a population of capsules can have a mean effective volumetric core-shell ratio of 80 to 20, 85 to 15, 90 to 10, 95 to 5, 98 to 2, 99 to 1, 99.5 to 0.5, 99.9 to 0.1, or 99.99 to 0.01. In embodiments, the population of capsules can have a mean effective volumetric core-shell ratio of about 80 to 20 to about 99.9 to 0.1, or about 90 to 10 to about 99.9 to 0.1, or about 95 to 5 to about 99.99 to 0.01, or about 97 to 3 to about 99.99 to 0.01 or about 95 to 5 to about 99.5 to 0.5. In embodiments, the entire population of capsules can have a mean effective volumetric core-shell ratio based on mass balance of core material to shell material of at least 80 to 20, or at least 90 to 10 or at least 95 to 5, or at least 97 to 3. Calculation of the mean effective volumetric core-shell ratio is detailed below.

High core to shell material ratios (either by weight or volume) can advantageously result in highly efficient capsules having a high content of benefit agent per capsule. This can, in embodiments, allow for high loading of benefit agent in a formulated product having the capsules and/or allow for lower amounts of capsules to be used in a formulated product. In embodiments, capsules having high core to shell material ratios can advantageously require less shell material, which in various embodiments is a non-function material. Less mass of such nonfunctional material reduces waste, can reduce cost by reducing the amount of precursor required, and can improve environmental impact by reducing the amount of organic precursor material required.

In embodiments, capsules or a population of capsules can have a delta fracture strength percentage of about 10% to about 500%, or about 10% to about 350%, 15% to about 350%, about 50% about 350%, or about 10% to about 230%, about 15% to about 230%, about 50% to about 230%, about 15% to about 200%, about 30% to about 200%. For example, the population of capsules can have a delta fracture strength percentage of about 10%, 15%, 20%, 25%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 300%, 350%, 400%, or 500%. The delta fracture strength percentage can be calculated using the following equation:

$$\text{Delta Fracture Strength}(\%) = \frac{FS@d_5 - FS@d_{90}}{FS@d_{50}} * 100$$

wherein the FS stands for fracture strength and FS at $d_i$ is the FS of the capsules at the percentile "i" of the volume size distribution. The delta fracture strength can be measured by the Delta Fracture Strength Test Method further described below and $d_5$, $d_{50}$, and $d_{90}$ can be measured as shown below.

Delta fracture strength percentages of about 15% to about 230% can be advantageous to ensure proper and more uniform capsule release of a benefit agent in a formulated product at the desired time. For example, in embodiments the formulated product can be a fabric care product, laundry detergent, soaps, dishwashing aid, cleaning, or skin or hair care products, and capsules having delta fracture strength percentages of about 15% to about 230% can beneficially ensure that substantially all the capsules release the benefit agent at the targeted phase of consumer use of the product.

In embodiments, the capsules can have a fracture strength at $d_{50}$ (absolute fracture strength at the median size of the population) of about 0.2 MPa to about 30 MPa, or about 0.4 MPa to about 10 MPa, or about 0.6 MPa to about 5 MPa, or even from about 0.8 MPa to about 4 MPa. For example, the fracture strength at $d_{50}$ can be about 0.2 MPa, 0.3 MPa, 0.4 MPa, 0.5 MPa, 0.6 MPa, 0.7 MPa, 0.8 MPa, 0.9 MPa, 1 MPa, 1.5 MPa, 2 MPa, 2.5 MPa, 3 MPa, 3.5 MPa, 4 MPa, 4.5 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 25 MPa, or 30 MPa.

In embodiments, the capsules can have a diameter of greater than 1 μm. In embodiments, capsules or a population of capsules can have a mean diameter of greater than 1 μm. In embodiments, capsules or a population of capsules can have a median diameter of greater than 1 μm. In any of the forgoing embodiments, the referenced diameter can be greater than or equal to 1 μm, 2 μm, 3 μm, 4 μm, 5 μm, 10 μm, 15 μm, 20 μm, or 25 μm. In any of the foregoing embodiments, the actual, mean, $d_{50}$ or other referenced diameter can be about 1 μm to 100 μm, or 1 μm to 80 μm, or 1 μm to 65 μm, or 1 μm to 50 μm, or 5 μm to 80 μm, or 10 μm to 80 μm, or 10 μm to 65 μm, or 15 μm to 65 μm, or 20 μm to 60 μm. For example, the referenced diameter can be about 1 μm, 2 μm, 3 μm, 4 μm, 5 μm, 10 μm, 15 μm, 20 μm, 25 μm, 30 μm, 35 μm, 40 μm, 50 μm, 55 μm, 60 μm, 65 μm, 70 μm, 75 μm, 80 μm, 85 μm, 90 μm, 95 μm, or 100 μm. In embodiments, the entire population of capsules can have a diameter of greater than 1 μm, 2 μm, 3 μm, 4 μm, 5 μm, or 10 μm. In embodiments, the entire population of capsules can include a diameter of 1 μm to 80 μm, 3 μm to 80 μm, or 5 μm to 65 μm, or 10 μm to 65 μm, 15 μm to 65 μm. For example, the capsules herein can have a diameter in the foregoing ranges, as illustrated, for example, in the cryo-SEM images shown in FIG. 5A, FIG. 6A, FIG. 7A, FIG. 8A, FIG. 9A, and FIG. 10A.

In embodiments, the capsules can have coefficient of variation ("CoV") of the diameter based on volume percent (or volume weighted size distribution) of less than 50%, or less than 45%, or less than 40%, or less than 35%. For example, the capsules CoV of diameter based on volume percent of about 20% to about 50%, or about 25% to about 40%, or about 20% to about 45%, or about 30% to about 40%. The CoV of diameter based on volume percent is calculated from the following equation:

$$CoVv(\%) = \frac{\sigma_v}{\mu_v} * 100$$

wherein $$\sigma_v = \left( \sum_{i=1\ um}^{493.3\ um} (x_{i,v} * (d_i - \mu_v)^2) \right)^{0.5}$$

$$\mu_v = \frac{\sum_{i=1\ um}^{493.3\ um} (x_{i,v} * d_i)}{\sum_{i=1\ um}^{493.3\ um} x_{i,v}}$$

where:
CoVv—Coefficient of variation of the volume weighted size distribution
$\sigma_v$—Standard deviation of distribution of volume weighted size distribution
$\mu_v$—mean of the distribution of volume weighted size distribution
$d_i$—diameter in fraction i (>1 um)
$x_{i,v}$—frequency in fraction i (corresponding to diameter i) of volume weighted size distribution.

In embodiments, the capsules can have a coefficient of variation of diameter based on number percent (number population diameter coefficient of variation) of about 1% to about 150%, or about 1% to about 100%, or about 10% to about 100%, or about 10% to about 80%, or about 25% to about 100%, or about 25% to about 75%. For example, the capsules can have coefficient of variation of diameter based on number percent of about 1%, 5%, 10%, 15%, 20%, 25%, 30%, 35%, 40%, 45%, 50%, 60%, 70%, 80%, 90%, 100%, or 150%. The number population diameter coefficient of variation can be calculated by the following equation:

$$CoVn(\%) = \frac{\sigma_n}{\mu_n} * 100$$

wherein $$\sigma_n = \left( \sum_{i=1\,um}^{493.3\,um} (x_{i,n} * (d_i - \mu_n)^2) \right)^{0.5}$$

$$\mu_n = \frac{\sum_{i=1\,um}^{493.3\,um} (x_{i,n} * d_i)}{\sum_{i=1\,um}^{493.3\,um} x_{i,n}}$$

Where:
CoVn—Coefficient of variation of the number weighted size distribution
- $\sigma_n$—Standard deviation of distribution of number weighted size distribution
- $\mu_n$—mean of the distribution of number weighted size distribution
- $d_i$—diameter in fraction i (>1 um)
- $x_{i,n}$—frequency in fraction i (corresponding to diameter i) of number weighted size distribution
- $\mu_n$—mean of the distribution of number distribution
- $x_{i,n}$—frequency in fraction i (corresponding to diameter i) of number distribution $$x_{i,n} = \frac{n_i}{\sum_{i=1\,um}^{493.3\,um} n_i}$$

$n_i$—number of capsules in the fraction i

The relationship between frequency in number and volume weighted size distribution is represented by the following equation:

$$x_{i,v} = \frac{x_{i,n} * d_i^3}{\sum_{i=1\,um}^{493.3\,um} (x_{i,n} * d_i^3)}$$

wherein the coefficients are defined as above.

Core

In any of the embodiments disclosed herein, the capsules can include a benefit agent in the core. In embodiments, the benefit agent can include one or more perfume compositions, perfume raw materials, silicone oils, waxes, hydrocarbons, higher fatty acids, essential oils, lipids, skin coolants, vitamins, sunscreens, antioxidants, glycerine, catalysts, bleach encapsulates, silicon dioxide encapsulates, malodor reducing agents, odor-controlling materials, chelating agents, antistatic agents, softening agents, agricultural materials such as pesticides, insecticides, nutrients, herbicides, fungus control, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, other construction agents, such as phase change materials, self-healing materials, skin care agents, glycerin, and natural actives, antibacterial actives, antiperspirant actives, cationic polymers, and dyes, food and feed agents such as antioxidants, probiotics and food and beverage colorants. In embodiments, the benefit agent can include one or more of perfume compositions, perfume raw materials, sanitization agents, disinfecting agents, antiviral agents, fabric refreshing agents and freshness extending agents, chlorine bleach odor control agents, dye fixatives, dyes, optical brighteners, color restoration/rejuvenation, enzymes, anti-foaming agents, fabric comfort agents, skin care agents, lubricants, waxes, hydrocarbons, malodor reducing agents, odor-controlling materials, fertilizers, nutrients, and herbicides.

In embodiments, the benefit agent can include a perfume or a perfume composition. In embodiments, the perfume composition can include one or more of perfume raw materials, essential oils, malodour reducing agents, and odour controlling agents.

In various embodiments, the perfume composition can include one or more perfume raw materials. In embodiments, the perfume composition can include, by weight based on the total weight of the perfume composition, a combination of (1) about 2.5% to about 30%, or about 5% to about 30%, of perfume raw materials characterized by a log P of less than 3.0 and a boiling point of less than 250° C.; (2) about 5% to about 30%, or about 7% to about 25%, of perfume raw material characterized by a log P of less than or equal to 3.0 and a boiling point greater than or equal to 250° C.; (3) about 35% to about 60%, or about 40% to about 55%, of perfume raw materials characterized by having a log P of greater than 3.0 and a boiling point of less than 250° C.; and (4) about 10% to about 45%, or about 12% to about 40%, of perfume raw materials characterized by having a log P greater than 3.0 and a boiling point greater than 250° C.

The value of the log of the Octanol/Water Partition Coefficient (log P) is computed for each perfume raw material in the perfume composition being tested. The log P of an individual perfume raw material is calculated using the Consensus log P Computational Model, version 14.02 (Linux) available from Advanced Chemistry Development Inc. (ACD/Labs) (Toronto, Canada), or equivalent, to provide the unitless log P value. The ACD/Labs' Consensus log P Computational Model is part of the ACD/Labs model suite, further details are provided in the Logarithm Octanol/Water Partition Coefficient (log P) Test Method below.

In embodiments, the perfume raw materials can be one or more of the following:

| Common Name | IUPAC Name |
| --- | --- |
| Methyl 2-methyl butyrate | methyl 2-methylbutanoate |
| Isopropyl 2-methyl butyrate | propan-2-yl 2-methylbutanoate |
| Ethyl-2 Methyl Butyrate | ethyl 2-methylbutanoate |
| Ethyl-2 Methyl Pentanoate | ethyl 2-methylpentanoate |
| Ethyl heptanoate | ethyl heptanoate |
| Ethyl octanoate | Ethyl octanoate |
| isobutyl hexanoate | 2-methylpropyl hexanoate |
| Amyl butyrate | pentyl butanoate |
| Amyl heptanoate | Pentyl heptanoate |
| Isoamyl isobutyrate | 3-methylbutyl 2-methylpropanoate |

| Common Name | IUPAC Name |
| --- | --- |
| Hexyl acetate | hexyl acetate |
| hexyl butyrate | hexyl butanoate |
| hexyl isobutyrate | hexyl 2-methylpropanoate |
| hexyl isovalerate | hexyl 3-methylbutanoate |
| hexyl propionate | hexyl propanoate |
| Ethyl 2-cyclohexyl propanoate | ethyl 2-cyclohexylpropanoate |
| Ethyl 3,5,5-trimethyl hexanoate | ethyl 3,5,5-trimethylhexanoate |
| glyceryl 5-hydroxydecanoate | 2,3-dihydroxypropyl 5-hydroxydecanoate |
| Prenyl acetate | 3-methyl 2-butenyl acetate |
| 3-methyl 2-butenyl acetate | 3-methyl 2-butenyl acetate |
| methyl 3-nonenoate | methyl non-3-enoate |
| Ethyl (E)-dec-4-enoate | Ethyl (E)-dec-4-enoate |
| Ethyl (E)-oct-2-enoate | Ethyl (E)-oct-2-enoate |
| Ethyl 2,4-decadienoate | ethyl (2E,4Z)-deca-2,4-dienoate |
| Ethyl 3-octenoate | ethyl (E)-oct-3-enoate |
| Citronellyl acetate | 3,7-dimethyloct-6-enyl acetate |
| Ethyl trans-2-decenoate | ethyl (E)-dec-2-enoate |
| 2-hexen-1-yl isovalerate | [(E)-hex-2-enyl]acetate |
| 2-hexen-1-yl propionate | [(E)-hex-2-enyl]propanoate |
| 2-hexen-1-yl valerate | [(E)-hex-2-enyl]pentanoate |
| 3-hexen-1-yl (E)-2-hexenoate | [(Z)-hex-3-enyl](E)-hex-2-enoate |
| 3-Hexen-1-yl 2-methyl butyrate | [(Z)-hex-3-enyl]2-methylbutanoate |
| 3-hexen-1-yl acetate | [(Z)-hex-3-enyl]acetate |
| 3-hexen-1-yl benzoate | [(Z)-hex-3-enyl]benzoate |
| 3-hexen-1-yl formate | [(Z)-hex-3-enyl]formate |
| 3-hexen-1-yl tiglate | [(Z)-hex-3-enyl](Z)-2-methylbut-2-enoate |
| 2-methyl butyl 2-methyl butyrate | 2-methylbutyl 2-methylbutanoate |
| Butyl isovalerate | butyl 3-methylbutanoate |
| Geranyl acetate | [(2E)-3,7-dimethylocta-2,6-dienyl] acetate |
| Geranyl butyrate | [(2E)-3,7-dimethylocta-2,6-dienyl] butanoate |
| Geranyl isovalerate | [(3E)-3,7-dimethylocta-3,6-dienyl]3-methylbutanoate |
| Geranyl propionate | [(2E)-3,7-dimethylocta-2,6-dienyl] propanoate |
| Allyl cyclohexane acetate | prop-2-enyl 2-cyclohexylacetate |
| Allyl Cyclohexyl Propionate | prop-2-enyl 3-cyclohexylpropanoate |
| allyl cyclohexyl valerate | prop-2-enyl 5-cyclohexylpentanoate |
| benzyl octanoate | benzyl octanoate |
| cocolactone | 6-pentyl-5,6-dihydropyran-2-one |
| coconut decanone | 8-methyl-1-oxaspiro(4.5)decan-2-one |
| gamma undecalactone | 5-heptyloxolan-2-one |
| gamma-decalactone | 5-hexyloxolan-2-one |
| gamma-dodecalactone | 5-octyloxolan-2-one |
| jasmin lactone | 6-[(E)-pent-2-enyl]oxan-2-one |
| Jasmolactone | 5-[(Z)-hex-3-enyl]oxolan-2-one |
| Nonalactone | 6-butyloxan-2-one |
| 6-acetoxydihydrotheaspirane | [2a,5a(S*)]-2,6,10,10-tetramethyl-1-oxaspiro[4.5]decan-6-yl acetate |
| Phenoxyethyl isobutyrate | 2-(phenoxy)ethyl 2-methylpropanoate |
| Pivacyclene | |
| Verdox | (2-tert-butylcyclohexyl) acetate |
| cyclobutanate | 3a,4,5,6,7,7a-hexahydro-4,7-methano-1g-inden-5(or 6)-yl butyrate |
| Dimethyl Anthranilate | methyl 2-methylaminobenzoate |
| Methyl Antranilate | methyl 2-aminobenzoate |
| Octyl Aldehyde | Octanal |
| Nonanal | Nonanal |
| Decyl aldehyde | Decanal |
| Lauric Aldehyde | Dodecanal |
| Methyl Nonyl Acetaldehyde | 2-methyl undecanal |
| Methyl Octyl Acetaldehyde | 2-methyl decanal |
| 2,4-Hexadienal | (2E,4E)-hexa-2,4-dienal |
| Intreleven Aldehyde | undec-10-enal |
| Decen-1-al | (E)-dec-2-enal |
| Nonen-1-al | (E)-2-nonen-1-al |
| Adoxal | 2,6,10-trimethylundec-9-enal |
| Geraldehyde | (4Z)-5,9-dimethyldeca-4,8-dienal |
| Iso cyclo citral | 2,4,6-trimethylcyclohex-3-ene-1-carbaldehyde |
| d-limonene mainly | 1-methyl-4-prop-1-en-2-yl-cyclohexene |
| Ligustral | 2,4-dimethylcyclohex-3-ene-1-carbaldehyde |
| Myrac aldehyde | 4-(4-methylpent-3-enyl)cyclohex-3-ene-1-carbaldehyde |
| Tridecenal | tridec-2-enal |
| Triplal | 2,4-dimethyl-3-cyclohexene-1-carboxaldehyde |
| Vertoliff | 1,2-dimethylcyclohex-3-ene-1-carbaldehyde |
| Cyclal C | 2,4-dimethylcyclohex-3-ene-1-carbaldehyde |
| Anisic aldehyde | 4-methoxybenzaldehyde |
| Helional | 3-(1,3-benzodioxol-5-yl)-2-methylpropanal |
| Heliotropin | 1,3-benzodioxole-5-carbaldehyde |
| Neocaspirene | |
| Beta Naphthol Ethyl Ether | 2-ethoxynaphtalene |
| Beta Naphthol Methyl Ether | 2-methoxynaphtalene |
| hyacinth ether | 2-cyclohexyloxyethylbenzene |
| 2-heptyl cyclopentanone (fleuramone) | 2-heptylcyclopentan-1-one |
| menthone-8-thioacetate | O-[2-[(1S)-4-methyl-2-oxocyclohexyl]propan-2-yl] ethanethioate |
| Nectaryl | 2-[2-(4-methyl-1-cyclohex-3-enyl)propyl]cyclopentan-1-one |
| Phenyl Naphthyl Ketone | naphthalen-2-yl-phenylmethanone |
| decen-1-yl cyclopentanone | 2-[(2E)-3,7-dimethylocta-2,6-dienyl]cyclopentan-1-one |
| fruity cyclopentanone (veloutone) | 2,2,5-trimethyl-5-pentylcyclopentan-1-one |
| 4-methoxy-2-methyl butane thiol (blackcurrant mercaptan) | 4-methoxy-2-methylbutane-2-thiol |
| Grapefruit Mercaptan | 2-(4-methyl-1-cyclohex-3-enyl)propane-2-thiol |
| Buccoxime | N-(1,5-dimethyl-8-bicyclo[3.2.1]octanylidene) hydroxylamine |
| Labienoxime | 2,4,4,7-Tetramethyl-6,8-nonadiene-3-one oxime |
| Undecavertol | (E)-4-methyldec-3-en-5-ol |
| Decanal diethyl acetal | 1,1-diethoxydecane |
| Diethyl maleate | diethyl but-2-enedioate |
| Ethyl Acetoacetate | ethyl 3-oxobutanoate |
| frutonile | 2-Methyldecanenitrile |
| Methyl dioxolan | ethyl 2-(2-methyl-1,3-dioxolan-2-yl)acetate |
| Cetalox | 3a,6,6,9a-tetramethyl-2,4,5,5a,7,8,9,9b-octahydro-1H-benzo[e][1]benzofuran |
| Cyclopentol | |
| Delta-damascone | (E)-1-(2,6,6-trimethyl-1-cyclohex-3-enyl)but-2-en-1-one |
| Eucalyptol | 1,3,3-trimethyl- 2-oxabicyclo[2,2,2] octane |
| Flor acetate | |
| Ionone gamma methyl | (E)-3-methyl-4-(2,6,6-trimethyl-1-cyclohex-2-enyl)but-3-en-2-one |
| Laevo trisandol | |
| Linalool | 3,7-dimethylocta-1,6-dien-3-ol |
| Violiff | [(4Z)-1-cyclooct-4-enyl]methyl carbonate |
| Cymal | 3-(4-propan-2-ylphenyl)butanal |
| Bourgeonal | 3-(4-tert-butylphenyl)propanal |

Malodour reducing agents maybe selected from antibacterial materials, enzyme inhibitors, reactive aldehydes, masking perfume raw materials and masking accords, and binding polymers, e.g., polyethylene imines.

In embodiments, the perfume raw materials can be present in an amount of about 10% to 100% by weight of the total weight of the perfume composition, or about 15% to about 95%, or about 20% to about 90%, or about 30% to about 90%, or about 20% to 100% by weight of the total weight of the perfume composition. In embodiments, the perfume raw materials can be present in an amount of about 10%, 15%, 20%, 25%, 30%, 40%, 50%, 60%, 70%, 80%, 90%, 95% or 100% by weight of the total weight of the perfume composition.

In embodiments, the perfume composition may include a perfume raw material characterized by having a log P of less than 3.0 and a boiling point of less than 250° C., in an amount of about 2.5% to 30% based on the total weight of perfume composition, or about 5% to 30%, or about 7% to 30%, or about 10% to 25%.

In embodiments, the perfume composition may include a perfume raw material characterized by having a log P of less or equal to 3.0 and a boiling point of greater than or equal to 250° C., in an amount of about 5% to 30% based on the total weight of perfume composition, or about 7% to 30%, or about 7% to 25%, or about 10% to 25%.

In embodiments, the perfume composition may include a perfume raw material characterized by having a log P of greater than 3.0 and a boiling point of less than 250° C., in an amount of 35% to 60% based on the total weight of the perfume composition, or 40% to 55%, or 45% to 55%.

In embodiments, the perfume composition may include a perfume raw material characterized by having a log P of greater than 3.0 and a boiling point of greater than 250° C., in an amount of 10% to 45% based on the total weight of the perfume composition, or 12% to 40%, or 15% to 35%, or 15% to 40%.

In embodiments, the benefit agent can be present in about 10 wt % or more based on the total weight of the core. In embodiments, the perfume composition can be present in about 10 wt % or more based on the total weight of the core. For example, the perfume composition can be present in about 20 wt % or more based on the total weight of the core, or about 30% or more, or about 40% or more, or about 45% or more, or about 50% or more, or about 60% or more, or about 70% or more, or about 80% or more, or about 90% or more or 100%.

In embodiments, the benefit agent can have a log P value of greater than or equal to 1. In embodiments, the benefit agent can have a log P value of 1 to 5, or 1 to 4, or 1 to 3 or 1 to 2. For example, the benefit agent can have a log P value of about 1, 1.5, 2, 2.5, 3, 3.5, 4, 4.5 or 5.

In embodiments, the core can further include additional components such as excipients, carriers, diluents, and other agents. In embodiments, the benefit agent can be admixed with an oil. Non-limiting examples of oils include isopropyl myristate, mono-, di-, and tri-esters of $C_4$-$C_{24}$ fatty acids, castor oil, mineral oil, soybean oil, hexadecanoic acid, methyl ester isododecane, isoparaffin oil, polydimethylsiloxane, brominated vegetable oil, and combinations thereof. Capsules may also have varying ratios of the oil to the benefit agent so as to make different populations of capsules that may have different bloom patterns. Such populations may also incorporate different perfume oils so as to make populations of capsules that display different bloom patterns and different scent experiences. U.S. Patent Application No. 2011/0268802 discloses other non-limiting examples of oils and is hereby incorporated by reference. In embodiments, the oil admixed with the benefit agent can include isopropyl myristate.

Shell

In any of the embodiments disclosed herein, the capsule shell can be a polymeric shell and can include greater than 90% polymeric material, or greater than 95% polymeric material, or greater than 98% polymeric material or greater than 99% polymeric material. In embodiments, the polymeric shell can include one or more of a homopolymer, a copolymer, and a crosslinked polymer. In embodiments, the polymeric shell can include a copolymer and a crosslinked polymer. In embodiments, the polymeric shell can be made from simple and/or complex coacervation. In embodiments, the polymeric shell can include one or more of polyacrylate, polymethacrylate, amino plastics such as melamine formaldehyde, polyurea, polyurethane, polyamide, polyvinyl alcohol, chitosan, gelatin, polysaccharides, or gums. In embodiments, the polymeric shell comprises poly(meth)acrylate. As used herein, the term "poly(meth)acrylate" can be polyacrylate, polymethacrylate, or a combination thereof. Suitable shell materials include materials selected from the group consisting of reaction products of one or more amines with one or more aldehydes, such as urea cross-linked with formaldehyde or gluteraldehyde, melamine cross-linked with formaldehyde; gelatin-polyphosphate coacervates optionally cross-linked with gluteraldehyde; gelatin-gum Arabic coacervates; cross-linked silicone fluids; polyamine reacted with polyisocyanates and mixtures thereof. In one aspect, the shell material comprises melamine cross-linked with formaldehyde.

Suitable shell materials include materials selected from the group consisting of reaction products of aliphatic or aromatic isocyanates, aliphatic or aromatic polyisocyanates, aliphatic or aromatic diisocyanates with aldehydes, or amines or polyamines or diamines and mixtures thereof. Suitable isocyanates include Desmodur N100, Takenate D-110N, Desmodur RC and Desmodur L75. Suitable amines include guanidine, 1,2-diaminopropane, 1,2-diaminoethane, diethylenetriamine, tris(2-aminoethyl)amine.

In embodiments, the capsules can have a shell thickness or an mean shell thickness of about 1 nm to about 1000 nm, or about 1 nm to about 800 nm, or about 1 nm to about 500 nm, or about 5 nm to about 500 nm, or about 5 nm to about 400 nm, or about 10 nm to about 500 nm, or about 10 nm to about 400 nm, or about 20 nm to about 500 nm, or about 20 nm to about 400 nm, or about 50 nm to about 400 nm, or about 50 nm to about 350 nm. For example, the shell thickness or mean shell thickness can be about 1 nm, 5 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 600 nm, 700 nm, 800 nm, 900 nm, or 1000 nm. In embodiments, the entire population of capsules can have a shell thickness of less than 1000 nm, or less than 800 nm, or less than 600 nm, or less than 400 nm, or less than 350 nm. FIGS. 5B, 6B, 7B, 8B, 9B, and 10B illustrate capsules in accordance with embodiments of the disclosure having shell thickness as recited herein.

In various embodiments, capsules and methods of making capsules allow for reduced shell thickness. For example, capsules can have thickness of about 20 nm to about 400 nm. In various embodiments, capsules having a shell thickness of about 20 nm to about 400 nm can minimize permeation of benefit agent during shelf life while maintaining sufficient fracture strength and a desired release profile to remain functional for a formulated product. For example, in such embodiments, capsules can have an absolute fracture strength at the median of the population ($d_{50}$) of about 0.2 MPa to about 30 MPa, or about 0.4 MPa to about 10 MPa, or about 0.6 MPa to about 5 MPa, or about 0.8 MPa to about 4 MPa. In such embodiments, the reduced shell thickness as compared to conventional capsules can beneficially allow for reduced amount of polymeric precursor material being required, which can reduce cost and can reduce environmental impact via increased activity and more efficient formulation.

In embodiments, capsules can have a delta fracture strength of about 15% to about 230%, and a shell thickness of about 20 nm to about 400 nm. Such a combination can be advantageous, allowing for uniform and timely release of the benefit agent in a formulated product, as well as reducing the polymeric material needed, which reduces cost of making the capsules and is more sustainable.

In embodiments, the capsules can have a number population diameter coefficient of variation of about 10% to about 100% and a mean shell thickness of about 20 nm to about 400 nm.

In embodiments, the capsules can have a number population diameter coefficient of variation of diameter of about 10% to about 100%, a delta fracture strength of about 15% to about 230%, and a mean shell thickness of about 20 nm to about 400 nm.

In embodiments, capsules can have a mean effective volumetric core-shell ratio of the capsule of core mater to shell material of greater than or equal to about 95 to 5, a delta fracture strength of about 15% to about 230%, and a shell thickness of about 20 nm to about 400 nm. In embodiments, capsules can have an mean effective volumetric core-shell ratio of greater than or equal to about 95 to 5, a number population diameter coefficient of variation of about 10% to about 100% and an mean shell thickness of about 20 nm to about 400 nm. In embodiments, capsules can have a mean effective volumetric core-shell ratio of greater than or equal to about 95 to 5, a number population diameter coefficient of variation of about 10% to about 100%, a delta fracture strength of about 15% to about 230%, and a mean shell thickness of about 20 nm to about 400 nm. In various embodiments, the capsules can have a number population diameter CoV of about 10% to about 100%. It is believed that such a CoV can allow for improved release performance and ability to formulate the capsules in to a final product. In various embodiments, capsules can have a delta fracture strength of about 15% to about 230%. Without intending to be bound by their, it is believed that the narrow delta fracture strength can correlate to improved and uniform fracturing of the capsules. In various embodiments, capsules can have a shell thickness of about 20 nm to about 400 nm and a mean effective volumetric core-shell ratio of greater than or equal to about 95 to 5. In such embodiments, less polymeric material can be required for making the shell, which can reduce waste and environmental impact without sacrificing stability and mechanically resistant capsules.

Method of Making

In accordance with embodiments, methods of making capsules having a core surrounded by a polymeric shell can include use of membrane emulsification. In various embodiments, capsules can be made by coacervation or solvent extraction methods. In various embodiments, methods of making capsules can include dispersing droplets of a dispersed phase in a continuous phase by passing the dispersed phase through a plurality of holes in a membrane. In embodiments, the method can include passing the dispersed phase through the membrane, from a first side of the membrane to a second side of the membrane, into a continuous phase flowing across the second side of the membrane. Upon exiting the plurality of holes on the second side of the membrane, the dispersed phase is formed into droplets of dispersed phase. In embodiments, the membrane can be mechanically moved while the dispersed phase is passed through the membrane to generate shear force on the second side of the membrane to exit the membrane and disperse into the flowing continuous phase.

In embodiments, the dispersed phase can include a polymer precursor and a benefit agent. In embodiments, the method can further include subjecting the emulsion of dispersed phase in continuous phase to conditions sufficient to initialize polymerization of a polymer precursor within the droplets of dispersed phase. Selection of suitable polymerization conditions can be made as is known in the art for particular polymer precursors present in the dispersed phase. Without intending to be bound by theory, it is believed that upon initialization of the polymerization, the polymer becomes insoluble in the dispersed phase and migrates within the droplet to the interface between the dispersed phase and the continuous phase, thereby defining the capsules shell.

In embodiments, the method can form capsules using polymerization method in which the shell forms from precursors polymerizing with in the core material and migrating to the interface to surround the core. In particular, the method can include dispersed phase droplets include a soluble polymer precursor that becomes insoluble upon polymerization and migrates to the interface between the dispersed phase and the continuous phase to thereby form the capsule shell surrounding the core, which includes the remaining components of the dispersed phase, such as a benefit agent, upon full polymerization.

In embodiments, the dispersed phase can include one or more of a polymer precursor, a process aider, and a benefit agent. In embodiments, the polymer precursor can include one or more monomers and oligomers, including mixtures of monomers and oligomers. In embodiments, the polymer precursor is soluble in the dispersed phase. In embodiments, the polymer precursor is multifunctional. As used herein, the term "multifunctional" refers to having more than one reactive chemical functional groups. For example, a reactive chemical functional group F can be a carbon-carbon double bond (i.e. ethylenic unsaturation) or a carboxylic acid. In embodiments, the polymer precursor can have any desired number of functional groups F. For example, the polymer precursor can include two, three, four, five, six, seven, eight, nine, ten, eleven, or twelve functional groups F. In embodiments, the polymer precursor can include a monomer or oligomer including at least one ethylenic unsaturation. In embodiments, the polymer precursor can include at least one multifunctional ethylenically unsaturated monomer having at least three functionalities. In embodiments, the polymer precursor can include a combination of ethylenically unsaturated monomers. In embodiments, the polymer precursor can include one or more ethylenically unsaturated monomers in combination with one or more ethylenically unsaturated monomers including one or more of other functionalities. In embodiments, the polymer precursor can include at least one ethylenically unsaturated monomer with one or more of other functionalities, such as, amino, amido, alcohol, thiol, sulfonic acid, and/or carboxylic functionality, in combination with one or more polymer precursors including at least one ethylenically unsaturated unmodified monomer. In embodiments, the polymer precursor can include one or more ethylenically unsaturated monomers in combination with one or more monomers including one or more of other functionalities selected from amine, amide, alcohol, thiol, sulfonic acids, and carboxylic acid functional group.

In embodiments, the polymer precursor can include one or more amine monomers selected from the group consisting of aminoalkyl acrylates, alkyl aminoalkyl acrylates, dialkyl aminoalkyl acrylates, aminoalkyl methacrylates, alkylamino aminoalkyl methacrylates, dialkyl aminoalkyl methacrylates, tertiarybutyl aminoethyl methacrylates, diethylaminoethyl methacrylates, dimethylaminoethyl methacrylates, and dipropylaminoethyl methacrylates; styrenic, allylic, vinylic, glycidyl ether, epoxy, and a plurality of multifunctional monomers or multifunctional oligomers. In embodiments, the polymer precursor can include one or more acrylate ester. For example, the polymer precursor can include one or more of methacrylate, ethyl acrylate, propyl acrylate, and butyl acrylate. In embodiments, the polymer precursor is one or more ethylenically unsaturated monomers or oligomer. In various embodiments, the ethylenically unsaturated monomer or oligomer is multifunctional. In embodiments, the multifunctional ethylenically unsaturated monomer or oligomer is a multifunctional ethylenically unsaturated (meth)acrylate monomer or oligomer. In embodiments, the multifunctional ethylenically unsaturated monomer or oligomer can be one or more of multifunctional urethane acrylates, pentaerytritol acrylates, and multi pentaerytritol acrylates. In embodiments, the multifunctional ethylenically unsaturated monomer or oligomer can include two, three, four, five, six, seven, eight, nine, ten, eleven, or twelve functional groups. In embodiments, the multifunctional ethylenically unsaturated monomer or oligomer can include at least three functional groups. In embodiments, the multifunctional ethylenically unsaturated monomer or oligomer can include at least four functionalities. In embodiments, the multifunctional ethylenically unsaturated monomer or oligomer can include at least five functional groups. Multifunctional monomers or oligomers can demonstrate improved crosslinking Without intending to be bound by theory it is believed that, the double bonds of the multifunctional monomers are serving as crosslinkers in polymerizations, such as radical polymerizations, thereby, the higher the number of double bonds, i.e., the more multifunctional the monomer is, the higher the crosslinking density.

In embodiments, the polymer precursor can include a multifunctional urethane acrylate. For example, the polymer precursor can include one or more of CN975 (Hexafunctional aromatic urethane acrylate), Ebecryl® 248 (an aliphatic urethane diacrylate diluted with 12% 1,6-hexanediol diacrylate, MW 1200 g/mol), CN9001 (aliphatic urethane acrylate), Incorez 701 (Incorez Ltd England, 1050 g/equivalent), CN9001NS (Sartmoer Co. USA, functionality 2, and MW 2813 g/mol), Laromer LR 8987, Laromer LR 8765, and Laromer LR 9000 (BASF, double-functionalized), aliphatic PUA (Tianjin, China, MW 3000 g/mol), ether-type urethane diacrylate oligomer (Wuxi Tianjiao-saite Co.), AR-12 [88] (Eternal Chemical, Taiwan, epoxy acrylate, difunctional), SM6020, EB2002 (waterborne resin, functionality 2), PUA CN972 (Sartomer Co., MW 3500 g/mol), Bayhydrol UV 2282 (Sayer Material Science, aqueous PUA), Genomer 4269 and Ganomer 6043 (Rahn USA, aliphatic urethane polyester acrylate), OAK-27 (Ciba Geigy Co., PUA), Ebecryl @ 270 (UCB, aliphatic, functionality 2 and MW 1500), bifunctional urethane acrylate oligomers, for example, Exothane 8, Exothane 10 and Exothane 26 (Esstech, USA), Ebecryl® 1290 (UCB, aliphatic urethane hexaacrylate), Ebecryl® 220 (UCB, aromatic urethane hexaacrylate), Ebecryl® 830 (UCB, polyester hexaacrylate), and Ebecryl® 8301 (UCB, aliphatic urethane hexaacrylate). In embodiments, the polymer precursor can include one or more of a melamine, polyacrylamide, silicones, polystyrene, polyurea, polyurethanes, polyacrylate based materials, polyacrylate esters based materials, gelatin, styrene malic anhydride, polyamides, aromatic alcohols, polyvinyl alcohol, resorcinol-based materials, poly-isocyanate-based materials, acetals (such as 1,3,5-triol-benzene-gluteraldehyde and 1,3,5-triol-benzene melamine), starch, cellulose acetate phthalate, and gums. In embodiments, the polymer precursor can include a polyacrylate or polymethacrylate precursor with at least three functionalities.

For example, the polymer precursor can be one or more of a hexafunctional aromatic urethane acrylate oligomer such as CN975, Ebecryl® 8301, pentaerythrityl tri-tetraacrylate, pentaerythritol triacrylate, dipentaerythritol pentaacrylate and dipentaerythritol hexaacrylate. In embodiments, the polymer precursor can be one or more of the following compounds:

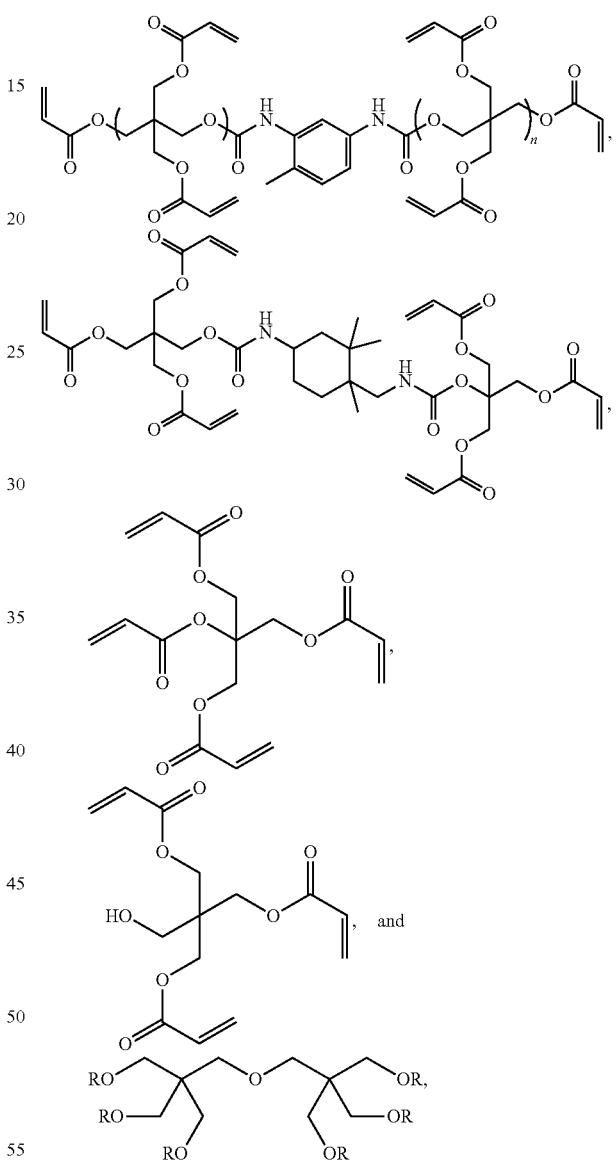

wherein R can be H or

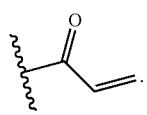

In embodiments, the polymer precursor can include one or more of the compounds in Table 1 below.

TABLE 1

| Commercial name | Name |
|---|---|
| CD561 | ALKOXYLATED HEXANEDIOL DIACRYLATE |
| CD564 | ALKOXYLATED HEXANEDIOL DIACRYLATE |
| CD595 | ACRYLATE ESTER |
| CD9043 | ALKOXYLATED NEOPENTYL GLYCOL DIACRYLATE |
| PRO11315 | PROPOXYLATED NEOPENTYL GLYCOL DIACRYLATE |
| SR101 | ETHOXYLATED BISPHENOL A DIMETHACRYLATE |
| SR205 | TRIETHYLENE GLYCOL DIMETHACRYLATE |
| SR209 | TETRAETHYLENE GLYCOL DIMETHACRYLATE |
| SR213 | 1,4-BUTANEDIOL DIACRYLATE |
| SR214 | 1,4-BUTANEDIOL DIMETHACRYLATE |
| SR230 | DIETHYLENE GLYCOL DIACRYLATE |
| SR231 | DIETHYLENE GLYCOL DIMETHACRYLATE |
| SR238B | 1,6 HEXANEDIOL DIACRYLATE |
| SR239 | 1,6 HEXANEDIOL DIMETHACRYLATE |
| SR247 | NEOPENTYL GLYCOL DIACRYLATE |
| SR252 | POLYETHYLENE GLYCOL (600) DIMETHACRYLATE |
| SR259 | POLYETHYLENE GLYCOL (200) DIACRYLATE |
| SR262 | 1,12 DODECANEDIOL DIMETHACRYLATE |
| SR268 | TETRAETHYLENE GLYCOL DIACRYLATE |
| SR272 | TRIETHYLENE GLYCOL DIACRYLATE |
| SR297 | 1,3-BUTYLENE GLYCOL DIMETHACRYLATE |
| SR306F | TRIPROPYLENE GLYCOL DIACRYLATE |
| SR306HP | TRIPROPYLENE GLYCOL DIACRYLATE |
| SR344 | POLYETHYLENE GLYCOL (400) DIACRYLATE |
| SR348 | ETHOXYLATED (2) BISPHENOL A DIMETHACRYLATE |
| SR349 | ETHOXYLATED (3) BISPHENOL A DIACRYLATE |
| SR480 | ETHOXYLATED (10) BISPHENOL DIMETHACRYLATE |
| SR508 | DIPROPYLENE GLYCOL DIACRYLATE |
| SR508IJ | DIPROPYLENE GLYCOL DIACRYLATE |
| SR540 | ETHOXYLATED (4) BISPHENOL A DIMETHACRYLATE |
| SR541 | ETHOXYLATED(6) BISPHENOL A DIMETHACRYLATE |
| SR601 | ETHOXYLATED (4) BISPHENOL A DIACRYLATE |
| SR602 | ETHOXYLATED (10) BISPHENOL A DIACRYLATE |
| SR610 | POLYETHYLENE GLYCOL (600) DIACRYLATE |
| SR644 | POLYPROPYLENE GLYCOL (400) DIMETHACRYLATE |
| SR9003B | PROPOXYLATED (2) NEOPENTYL GLYCOL DIACRYLATE |
| SR9038 | ETHOXYLATED (30) BISPHENOL A DIACRYLATE |
| SR9209A | ALKOXYLATED ALIPHATIC DIACRYLATE |
| SR350 | TRIMETHYLOLPROPANE TRIMETHACRYLATE |
| SR351H | TRIMETHYLOLPROPANE TRIACRYLATE |
| SR351LV | LOW VISCOSITY TRIMETHYLOPROPANE TRIACRYLATE |
| SR368 | TRIS (2-HYDROXY ETHYL) ISOCYANURATE TRIACRYLATE |
| SR368D | TRIS (2-HYDROXY ETHYL) ISOCYANURATE TRIACRYLATE |
| SR415 | ETHOXYLATED(20) TRIMETHYLOLPROPANE TRIACRYLATE |
| SR444 | PENTAERYTHRITOL TRIACRYLATE |
| SR454 | ETHOXYLATED (3) TRIMETHYLOLPROPANE TRIACRYLATE |
| SR454HP | ETHOXYLATED (3) TRIMETHYLOLPROPANE TRIACRYLATE |
| SR492 | PROPOXYLATED (3) TRIMETHYLOLPROPANE TRIACRYLATE |
| SR499 | ETHOXYLATED (6) TRIMETHYLOLPROPANE TRIACRYLATE |
| SR501 | PROPOXYLATED (6) TRIMETHYLOLPROPANE TRIACRYLATE |
| SR502 | ETHOXYLATED (9) TRIMETHYLOLPROPANE TRIACRYLATE |
| SR9020 | PROPOXYLATED (3) GLYCERYL TRIACRYLATE |
| SR9020HP | PROPOXYLATED (3) GLYCERYL TRIACRYLATE |
| SR295 | PENTAERYTHRITOL TETRAACRYLATE |
| SR355 | DI-TRIMETHYLOLPROPANE TETRAACRYLATE |
| SR399 | DIPENTAERYTHRITOL PENTAACRYLATE |
| SR494 | ETHOXYLATED (4) PENTAERYTHRITOL TETRAACRYLATE |
| SR9041 | PENTAACRYLATE ESTER |
| SR306HP | TRIPROPYLENE GLYCOL DIACRYLATE |
| SR351HP | TRIMETHYLOLPROPANE TRIACRYLATE |
| SR454HP | ETHOXYLATED (3) TRIMETHYLOLPROPANE TRIACRYLATE |
| CD9051 | TRIFUNCTIONAL ACID ESTER |
| CD9054 | TRIFUNCTIONAL ACID ESTER |
| SR9009 | TRIFUNCTIONAL METHACRYLATE ESTER |
| SR9011 | TRIFUNCTIONAL METHACRYLATE ESTER |
| SR9012 | TRIFUNCTIONAL ACRYLATE ESTER |
| SR9050 | MONOFUNCTIONAL ACID ESTER |
| CN104A80Z | EPOXY ACRYLATE BLENDED WITH SR306 |
| CN104D80 | EPOXY ACRYLATE BLENDED WITH SR9020 |
| CN104Z | EPOXY ACRYLATE |
| CN110 | EPOXY ACRYLATE OLIGOMER |
| CN111US | EPOXIDIZED SOY BEAN OIL ACRYLATE |
| CN112C60 | EPOXY NOVOLAK ACRYLATE BLENDED WITH SR351 |
| CN113D70 | ACRYLIC OLIGOMER/MONOMER BLEND |

TABLE 1-continued

| Commercial name | Name |
|---|---|
| CN116 | MODIFIED EPOXY ACRYLATE |
| CN117 | MODIFIED EPOXY ACRYLATE |
| CN118 | MODIFIED EPOXY ACRYLATE |
| CN119 | MODIFIED EPOXY ACRYLATE |
| CN120A75 | EPOXY ACRYLATE BLENDED WITH SR306 |
| CN120c60 | EPOXY ACRYLATE BLENDED WITH SR351 |
| CN120c80 | EPOXY ACRYLATE BLENDED WITH SR351 |
| CN120D80 | EPOXY ACRYLATE BLENDED WITH SR9020 |
| CN131 | LOW VISCOSITY AROMATIC MONOACRYLATE |
| CN131B | LOW VISCOSITY ACRYLIC OLIGOMER |
| CN132 | LOW VISCOSITY DIACRYLATE OLIGOMER |
| CN133 | LOW VISCOSITY TRIACRYLATE OLIGOMER |
| CN136 | MODIFIED EPOXY ACRYLATE |
| CN160 | ACRYLATED LINSEED OIL OLIGOMER |
| CN2003B | MODIFIED EPOXY ACRYLATE OLIGOMER |
| CN2602 | EPOXY ACRYLATE OLIGOMER |
| CN UVE 150/80 | EPOXY ACRYLATE BLENDED WITH 20% TRIPROPYLENE GLYCOL DIACRYLATE |
| CN UVE 151 | EPOXY ACRYLATE |
| CN154 | EPOXY METHACRYLATE |
| CN131 | LOW VISCOSITY AROMATIC MONOACRYLATE |
| CN131B | LOW VISCOSITY ACRYLIC OLIGOMER |
| CN132 | LOW VISCOSITY DIACRYLATE OLIGOMER |
| CN152 | LOW VISCOSITY MONOACRYLATE OLIGOMER |
| CN549 | ACRYLIC OLIGOMER |
| CN2285 | ACRYLIC OLIGOMER |
| CN3100 | LOW VISCOSITY OLIGOMER |
| CN3105 | LOW VISCOSITY OLIGOMER |
| CN292 | POLYESTER ACRYLATE |
| CN293 | ACRYLATED POLYESTER OLIGOMER |
| CN299 | ACRYLATED POLYESTER OLIGOMER |
| CN704 | ACRYLATED POLYESTER ADHESION PROMOTER |
| CN2200 | POLYESTER ACRYLATE OLIGOMER |
| CN2203 | POLYESTER ACRYLATE OLIGOMER |
| CN2207 | POLYESTER ACRYLATE OLIGOMER |
| CN2261 | POLYESTER ACRYLATE OLIGOMER |
| CN2261LV | POLYESTER ACRYLATE OLIGOMER |
| CN2262 | POLYESTER ACRYLATE |
| CN2264 | POLYESTER ACRYLATE OLIGOMER |
| CN2270 | POLYESTER ACRYLATE OLIGOMER |
| CN2271E | POLYESTER ACRYLATE OLIGOMER |
| CN2273 | POLYESTER ACRYLATE OLIGOMER |
| CN2279 | POLYESTER ACRYLATE |
| CN2281 | POLYESTER ACRYLATE OLIGOMER |
| CN2282 | POLYESTER ACRYLATE OLIGOMER |
| CN2298 | ACRYLATED POLYESTER OLIGOMER |
| CN2302 | POLYESTER ACRYLATE OLIGOMER |
| CN2303 | POLYESTER ACRYLATE OLIGOMER |
| CN2304 | POLYESTER ACRYLATE OLIGOMER |
| CN929 | ALIPHATIC TRIFUNCTIONAL URETHANE ACRYLATE |
| CN959 | ALIPHATIC URETHANE DIACRYLATE OLIGOMER WITH ACRYLATE MONOMER DILUENT |
| CN961H81 | ALIPHATIC URETHANE ACRYLATE BLENDED WITH SR256 |
| CN962 | ALIPHATIC URETHANE ACRYLATE |
| CN963A80 | ALIPHATIC URETHANE ACRYLATE BLENDED WITH SR306 |
| CN963B80 | ALIPHATIC URETHANE ACRYLATE BLENDED WITH SR238 |
| CN963E80 | ALIPHATIC URETHANE ACRYLATE BLENDED WITH SR454 |
| CN963J85 | ALIPHATIC URETHANE ACRYLATE BLENDED WITH SR506 |
| CN964 | ALIPHATIC URETHANE ACRYLATE |
| CN964A85 | ALIPHATIC URETHANE ACRYLATE BLENDED WITH SR306 |
| CN965 | ALIPHATIC URETHANE ACRYLATE |
| CN966H90 | ALIPHATIC URETHANE ACRYLATE BLENDED WITH SR256 |
| CN966J75 | ALIPHATIC URETHANE ACRYLATE BLENDED WITH SR506 |
| CN968 | ALIPHATIC URETHANE ACRYLATE |
| CN980 | ALIPHATIC URETHANE ACRYLATE |
| CN981 | ALIPHATIC URETHANE ACRYLATE |
| CN981B88 | ALIPHATIC URETHANE ACRYLATE BLENDED WITH SR238 |
| CN982A75 | ALIPHATIC URETHANE ACRYLATE BLENDED WITH SR306 |
| CN982B88 | ALIPHATIC URETHANE ACRYLATE BLENDED WITH SR238 |
| CN983 | ALIPHATIC URETHANE ACRYLATE |
| CN985B88 | ALIPHATIC URETHANE ACRYLATE BLENDED WITH SR238 |
| CN986 | ALIPHATIC URETHANE ACRYLATE |
| CN989 | ALIPHATIC URETHANE ACRYLATE |
| CN991 | ALIPHATIC URETHANE ACRYLATE |
| CN996 | ALIPHATIC URETHANE ACRYLATE |
| CN2920 | ALIPHATIC URETHANE ACRYLATE OLIGOMER |
| CN2921 | ALIPHATIC URETHANE ACRYLATE BLEND |
| CN3211 | ALIPHATIC URETHANE ACRYLATE OLIGOMER |

TABLE 1-continued

| Commercial name | Name |
|---|---|
| CN9001 | ALIPHATIC URETHANE ACRYLATE OLIGOMER |
| CN9004 | ALIPHATIC URETHANE ACRYLATE |
| CN9005 | ALIPHATIC URETHANE ACRYLATE |
| CN9006 | ALIPHATIC URETHANE ACRYLATE |
| CN9007 | ALIPHATIC URETHANE ACRYLATE |
| CN9009 | ALIPHATIC URETHANE ACRYLATE OLIGOMER |
| CN9010 | ALIPHATIC URETHANE ACRYLATE OLIGOMER |
| CN9011 | ALIPHATIC URETHANE OLIGOMER |
| CN9013 | ALIPHATIC URETHANE ACRYLATE OLIGOMER |
| CN9018 | ALIPHATIC URETHANE ACRYLATE OLIGOMER |
| CN9021 | ALIPHATIC URETHANE ACRYLATE OLIGOMER |
| CN9039 | ALIPHATIC URETHANE ACRYLATE OLIGOMER |
| CN9178 | ALIPHATIC URETHANE ACRYLATE |
| CN9290US | ALIPHATIC URETHANE ACRYLATE |
| CN9788 | ALIPHATIC URETHANE ACRYLATE |
| CN9893 | ALIPHATIC URETHANE ACRYLATE |
| CN970A60 | AROMATIC URETHANE ACRYLATE BLENDED WITH SR306 |
| CN970E60 | AROMATIC URETHANE ACRYLATE BLENDED WITH SR454 |
| CN971A80 | AROMATIC URETHANE ACRYLATE BLENDED WITH SR306 |
| CN972 | AROMATIC URETHANE ACRYLATE |
| CN973A80 | AROMATIC URETHANE ACRYLATE BLENDED WITH SR306 |
| CN973H85 | AROMATIC URETHANE ACRYLATE BLENDED WITH SR256 |
| CN973J75 | AROMATIC URETHANE ACRYLATE BLENDED WITH SR506 |
| CN975 (mix) | AROMATIC HEXAFUNCTIONAL URETHANE ACRYLATE |
| CN978 | AROMATIC URETHANE ACRYLATE |
| CN992 | AROMATIC URETHANE ACRYLATE |
| CN997 | AROMATIC URETHANE ACRYLATE OLIGOMER |
| CN9165US | AROMATIC ACRYLATE ESTER |
| CN9167US | AROMATIC URETHANE ACRYLATE |
| CN9782 | AROMATIC URETHANE ACRYLATE |
| CN9783 | AROMATIC URETHANE ACRYLATE |
| CN1963 | URETHANE METHACRYLATE |
| CN501 | AMINE-MODIFIED POLYETHER ACRYLATE OLIGOMER |
| CN550 | AMINE-MODIFIED POLYETHER ACRYLATE OLIGOMER |
| CN551 | AMINE-MODIFIED POLYETHER ACRYLATE OLIGOMER |
| CN146 | ACRYLIC OLIGOMER |
| CN147 | ACIDIC ACRYLATE OLIGOMER |
| CN704 | ACRYLATED POLYESTER ADHESION PROMOTER |
| CN820 | ACRYLIC OLIGOMER |
| CN301 | POLYBUTADIENE DIMETHACRYLATE |
| CN303 | POLYBUTADIENE DIMETHACRYLATE |
| CN309 | HYDROPHOBIC ACRYLATE ESTER |
| CN990 | SILICONIZED URETHANE ACRYLATE OLIGOMER |
| CN9800 | ALIPHATIC SILICONE ACRYLATE |
| SR228 | HIGH Tg ACRYLATE MONOMER |
| SR833S | TRICYCLODECANE DIMETHANOL DIACRYLATE |
| SR496 | HIGHLY ALKOXYLATED TETRAACRYLATE |
| SR496 | HIGHLY ALKOXYLATED TETRAACRYLATE |
| CN120Z | EPOXY ACRYLATE |
| CN9029 | ALIPHATIC URETHANE ACRYLATE |
| CN9030 | ALIPHATIC URETHANE ACRYLATE OLIGOMER |
| CN9031 | ALIPHATICURETHANE ACRYLATE OLIGOMER |
| CN9062 | DUAL CURE ALIPHATIC URETHANE ACRYLATE OLIGOMER |
| SR206 | ETHYLENE GLYCOL DIMETHACRYLATE |
| SR4368 | |
| CN975 | AROMATIC HEXAFUNCTIONAL URETHANE ACRYLATE |

In embodiments, the polymer precursor can include one or more of methyl methacrylate (MMA) ethyl methacrylate (EMA), methyl acrylate (MA), 2-ethylhexyl acrylate, di(ethylene glycol)ethyl ether acrylate (DEGEEA), butyl acrylate (BA), trimethylol propane triacrylate (TMPTA), tripropylene glycol diacrylate (TPGDA), acrylonitrile, ethyl acrylate, 2-hydroxy acrylate (2-HBA), 2-hydroxyethyl acrylate (2-HEA), 2-hydroxypropyl acrylate (2-HPA), 2-(2-ethoxyethoxy) ethyl acrylate (EOEOEA), Lauryl methacrylate, styrene, iso-bornyl acrylate (iBOA), stearyl acrylate, dipentaerylthritol penta-acrylate (DPHPA), vinyl methacrylate, Photomer 4003 (ethoxylated (4) nonylphenol acrylate and photomer 8061 (propoxylated (3) nonylphenol ether acrylate, Bisphenol A bis(2-hydroxy-3-methacryloxypropyl) ether (Bis-GMA), 1,6-hexanediol diacrylate (HDDA), heptadecafluorodecyl methacrylate, glycidyl methacrylate (GMA), 2,2,3,3-tetrafluoropro-pyl acrylate (TFPA), di-pentaerythritol penta/hexa acrylate (DPHPA), trimethylol-propane triacrylate (TMPTA), triethylene glycol dimethacrylate (TEGDMA), 2-phenoxyl ethyl acrylate, 2,2,2-trifluoroethyl methacrylate, N,N'-dimethyl aminoethyl methacrylate (DMAEMA), pentaerythriyol tetraacrylate (PETEA), triallyl cyanurate, triallyl isocyanurate, and N-acryloyl-morpholinrs (AMCO).

In embodiments, the polymer precursor present in the dispersed phase can be in an amount of about 0.01 wt % to about 30 wt % based on the total weight of the dispersed phase, or about 0.01 wt % to about 20 wt %, or about 0.05 wt % to about 20 wt %, or about 0.1 wt % to about 15 wt %, or about 0.5 wt % to about 15 wt %, or about 1 wt % to about 15 wt %, or about 5 wt % to about 15 wt %, or about 0.05 wt % to about 15 wt %, or about 0.1 wt % to about 10 wt %, or about 0.1 wt % to about 5 wt %, or about 0.1 wt % to about 2 wt % based on the total weight of the dispersed phase. For example, the polymer precursor can be present in about 0.01 wt %, 0.05 wt %, 0.1 wt %, 0.5 wt %, 1 wt %, 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, or 15 wt %, based on the total weight of the dispersed phase.

In embodiments, the polymer precursor can include a main monomer and a minor monomer, where the main monomer is present in an amount of at least 51% and the minor monomer is present in an amount of no more than 49% based on the total weight of the polymer precursor. In embodiments, the minor monomer can include a combination of one or more of the monomers or oligomers provided in any suitable ratio to achieve a total minor monomer content of up to 49% based on the total weight of the polymer precursor. In embodiments, the main monomer is an ethylenically unsaturated monomer or oligomer and the minor monomer is any one or more ethylenically unsaturated monomers having a different functionality, such as amino, amido, alcohol, thiol, sulfonic acid, and/or carboxylic functionality.

In embodiments, the continuous phase can be free or substantially free of polymer precursor. As used herein, the term "substantially free of polymer precursor" means that the continuous phase contains 1 wt % or less of the polymer precursor based on the total weight of the continuous and dispersed phase.

In embodiments, the polymer precursor included in the dispersed phase is polymerized into the polymer that makes up about 50% or more of the shell, 75% or more of the shell, 90 wt % or more of the shell, or about 95 wt % or more of the shell, or about 96 wt % of the shell, or about 97 wt % of the shell, or about 98 wt % of the shell.

In embodiments, the method of making the capsules can include a stabilizer system in one or both of the dispersed phase and the continuous phase. In embodiments, the stabilizer system can be present in an amount of about 0.01 wt % to about 30 wt % based on the total weight of the continuous phase, or about 0.1 wt % to about 25 wt %, or about 0.5 wt % to about 20 wt %, or about 1 wt % to about 20 wt %, or about 0.5 wt % to about 10 wt % based on the total weight of the continuous phase. For example, the stabilizer system can be present in an amount of about 0.1 wt %, 0.2 wt %, 0.3 wt %, 0.4 wt %, 0.5 wt %, 1 wt %, 2 wt %, 3 wt %, 4 wt %, 5 wt %, 6 wt %, 7 wt %, 8 wt %, 9 wt %, or 10 wt %. In embodiments, the polyvinyl alcohol aqueous solution can have a viscosity of about 2 cP to 200 cP, or about 5 cP to 180 cP, or about 10 cP to about 150 cP. For example, the polyvinyl alcohol can have a viscosity of about 2 cP, 3 cP, 4 cP, 5 cP, 10 cP, 15 cP, 20 cP, 25 cP, 30 cP, 40 cP, 50 cP, 60 cP, 70 cP, 80 cP, 90 cP, 100 cP, 110 cP, 120 cP, 130 cP, 140 cP, 150 cP, 160 cP, 170 cP, 180 cP, 190 cP, or 200 cP.

In embodiments, the stabilizer system can include a primary stabilizer present in the continuous phase. In embodiments, the primary stabilizer can be present in an amount of about 51 wt % to about 100 wt % based on the total weight of the stabilizer system. In embodiments, the primary stabilizer can include an amphiphilic non-ionic stabilizer that can be soluble or dispersible in the continuous phase. In embodiments, the primary stabilizer can include one or more of a polysaccharide, a polyacrylic acid based stabilizer, a pyrrolidone based polymer, naturally derived gums, polyalkylene glycol ether; condensation products of alkyl phenols, aliphatic alcohols, or fatty acids with alkylene oxide, ethoxylated alkyl phenols, ethoxylated arylphenols, ethoxylated polyaryl phenols, carboxylic esters solubilized with a polyol, polyvinyl alcohol, polyvinyl acetate, copolymers of polyvinyl alcohol and polyvinyl acetate, polyacrylamide, poly(N-isopropylacrylamide), poly(2-hydroxypropyl methacrylate), poly(2-ethyl-2-oxazoline), polyalkylenimine, poly(2-isopropenyl-2-oxazoline-co-methyl methacrylate), poly(methyl vinyl ether), polyvinyl alcohol-co-ethylene, and acetatecyl modified polyvinyl alcohol. In embodiments, the primary stabilizer can include a polyvinyl alcohol. In embodiments, the polyvinyl alcohol can have a degree of hydrolysis of 50% to 99.9%. In embodiments, the polyvinyl alcohol can have a degree of hydrolysis of below 95%. In embodiments, the polyvinyl alcohol can have a degree of hydrolysis of 50% to 95%, or 50% to 95%, or 60% to 95%, or 70% to 95%, or 75% to 95%. For example, the degree of hydrolysis can be 50%, 55%, 60%, 65%, 70%, 75%, 80%, 85%, 90% or 95%.

In embodiments, selection of the stabilization system as described herein can beneficially aid in stabilization of the droplets at the membrane surface, which in turn can provide a more uniform droplet size, with a low coefficient of variation or capsules size, a low delta fracture strength percentage, and also serve to tune the mean size of the distribution. In embodiments, the primary stabilizer, such as polyvinyl alcohol, can be utilized to stabilize the emulsion at the interface between the dispersed phase droplets and the continuous phase and aid in preventing or reducing coalescence of the droplets. In embodiments, the stabilizer system can aid in providing an emulsion with a number population diameter coefficient of variation of about 10% to about 100%.

In embodiments, the stabilizer system further includes one or more minor stabilizers. The combination of two or more types of surfactants can be used in embodiments to address the kinetic and thermodynamic stability of emulsion. In embodiments, the stabilizer system includes minor stabilizers in an amount of about 0 wt % to about 49 wt % based on the total weight of the stabilizer system. For example, the minor stabilizer can be present in an amount of 0%, 1%, 2%, 3%, 4%, 5%, 10%, 20%, 30%, 40%, or 49%, of the total weight of the stabilizer system. In embodiments, the minor stabilizers can include a minor protective colloid present in the continuous phase. In embodiments, the minor protective colloid can include one or more of a low molecular weight surfactant, a cationic stabilizer, and an anionic stabilizer. In embodiments, the minor stabilizer can include a low molecular weight surfactant, wherein the low molecular weight surfactant can include one or more short chain ethylene oxide/propylene oxide copolymers and an alkylsulfate. In embodiments, the ethylene oxide/propylene oxide copolymers have a molecular weight of less than or equal to 3500 g/mol. In embodiments, the ethylene oxide/propylene oxide copolymers have a ratio of ethylene oxide to propylene oxide of about 0.7 to 1.4. In embodiments, the ethylene oxide/propylene oxide copolymers have less than 30% branching.

In accordance with embodiments, the method can utilize a membrane having any desired shape. For example, the membrane can have a cross-sectional shape that is round, square, elliptical, rectangular. The cross section of the membrane is the cross section through a plane parallel to the direction of flow of the dispersed phase through the membrane. In embodiments, the membrane can be planar. In embodiments, the membrane can be cylindrical, for example, as illustrated in FIG. 1.

In embodiments, the membrane can mechanically move in one or more directions. For example, the membrane can be oscillated, rotated about an axis, vibrated, or pulsed.

In embodiments, the membrane can be moved in a direction perpendicular to the exiting direction of the disperse phase from the membrane.

In embodiments, the movement of the membrane can be at a rotation frequency of about 5 Hz to about 100 Hz, or about 10 Hz to about 100 Hz, or about 10 Hz to about 70 Hz. For example, the rotation frequency can be about 5 Hz, 10 Hz, 15 Hz, 20 Hz, 25 Hz, 30 Hz, 35 Hz, 40 Hz, 45 Hz, 50 Hz, 60 Hz, 70 Hz, 80 Hz, 90 Hz or 100 Hz.

In embodiments, the membrane can have an amplitude of movement of about 0.1 mm to about 30 mm, or about 1 mm to about 20 mm, or about 1 mm to about 10 mm. For example, the membrane can have an amplitude of movement of about 0.1 mm, 0.5 mm, 1 mm, 2 mm, 3 mm, 4 mm, 5 mm, 6 mm, 7 mm, 8 mm, 9 mm, 10 mm, 15 mm, 20 mm, 25 mm, or 30 mm.

In embodiments, the membrane can have a thickness of about 1 μm to about 1000 μm, or about 5 μm to about 500 μm, or about 10 μm to about 500 μm, or about 20 μm to about 200 μm. For example, the membrane can have a thickness of about 10 μm, 15 μm, 20 μm, 25 μm, 30 μm, 40 μm, 50 μm, 60 μm, 70 μm, 80 μm, 90 μm, 100 μm, 110 μm, 120 μm, 130 μm, 140 μm, 150 μm, or 200 μm.

In embodiments, the membrane can be made of one or more of metal, ceramic material, silicon or silicon oxide and polymeric material. In embodiments, the membrane is substantially metallic, or wholly metallic. According to another embodiment, the membrane is a chemically-resistant metal such as nickel or steel.

Figure 2:
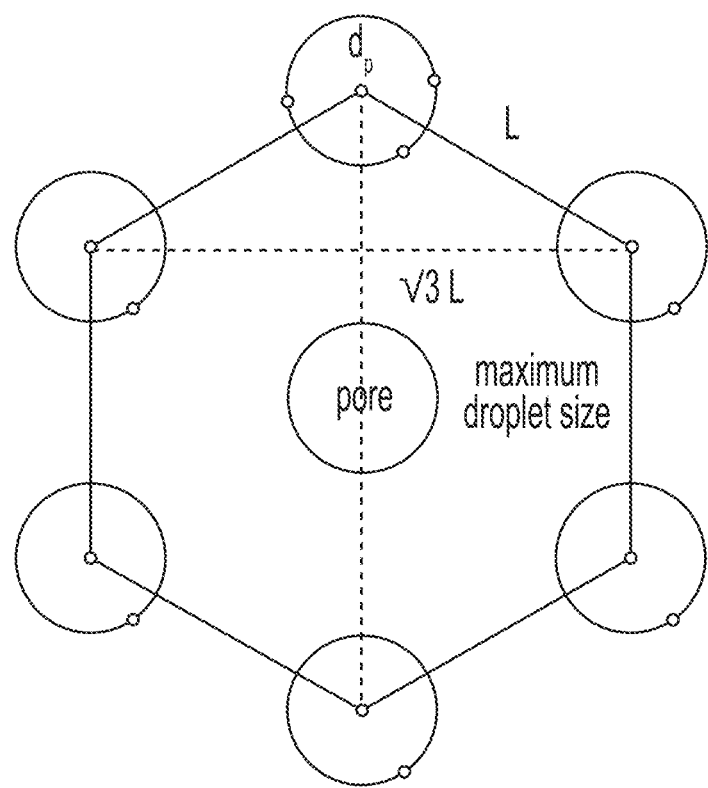
FIG. 2 is a schematic illustration of a membrane having a plurality of holes in the membrane for use in methods in accordance with embodiments of the disclosure.
Figure 3A:
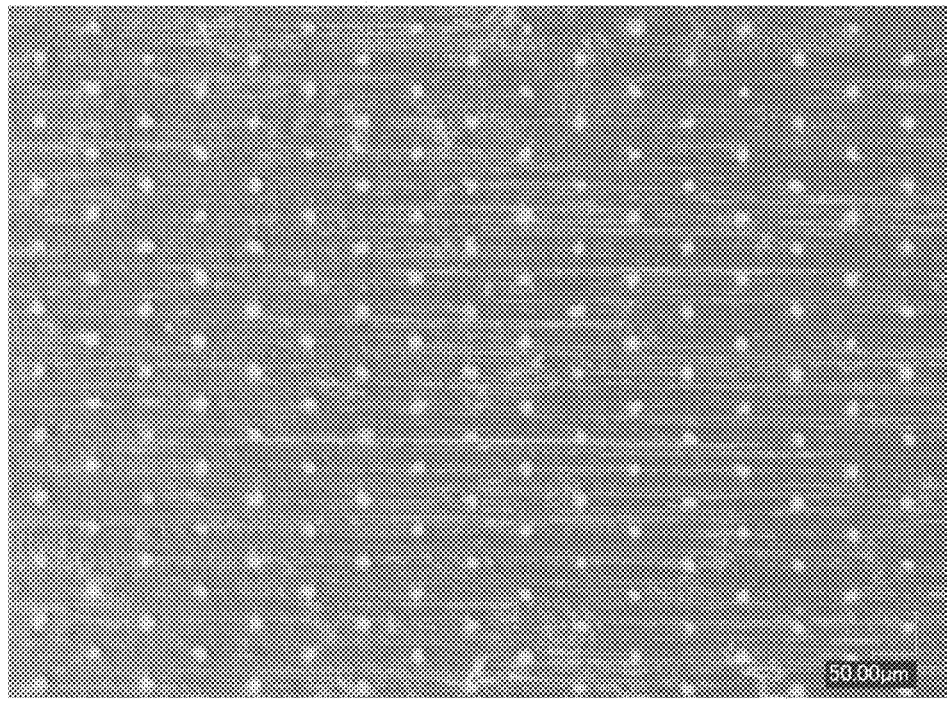
FIG. 3A is a photograph of a membrane having a plurality of holes in the membrane for use in methods in accordance with embodiments of the disclosure.
Figure 3B:
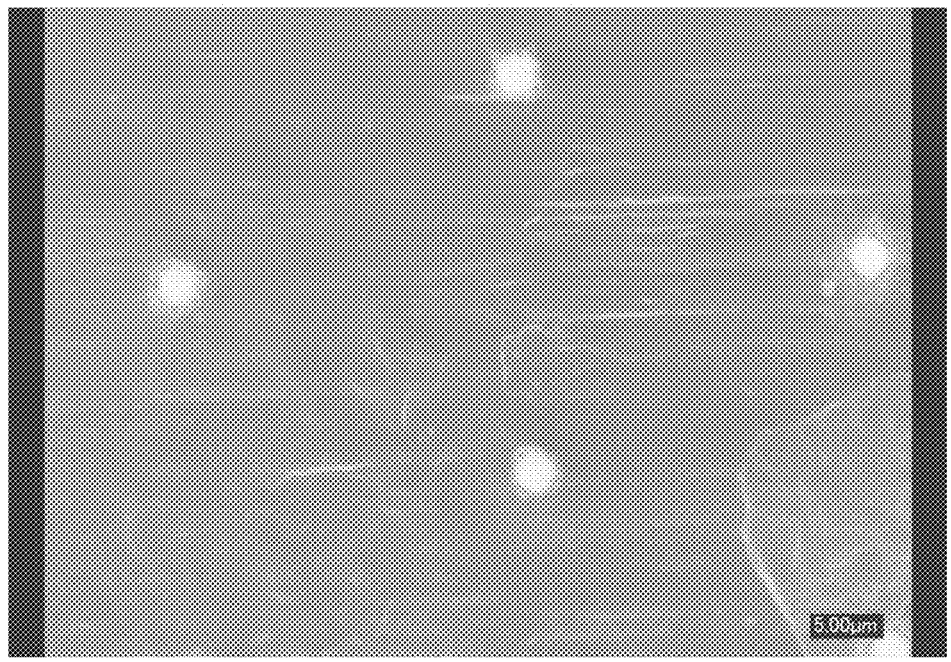
FIG. 3B is a zoomed in photograph of the membrane of FIG. 3A.
Figure 4A:
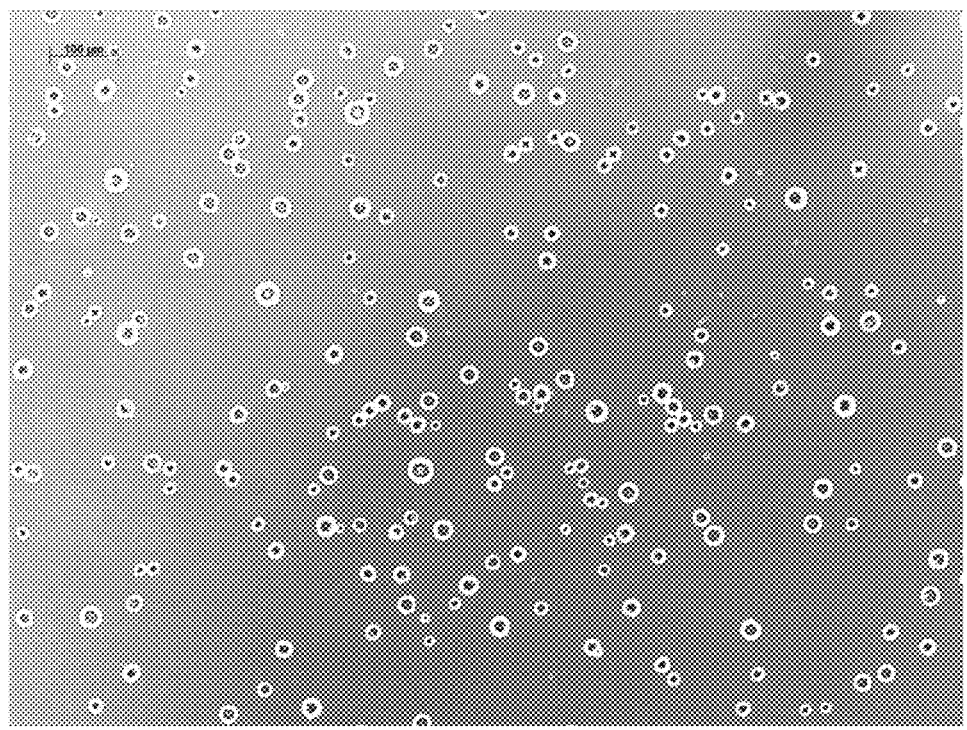
FIG. 4A is an optical microscopy image of a population of capsules in accordance with embodiments of the disclosure.
Figure 4B:
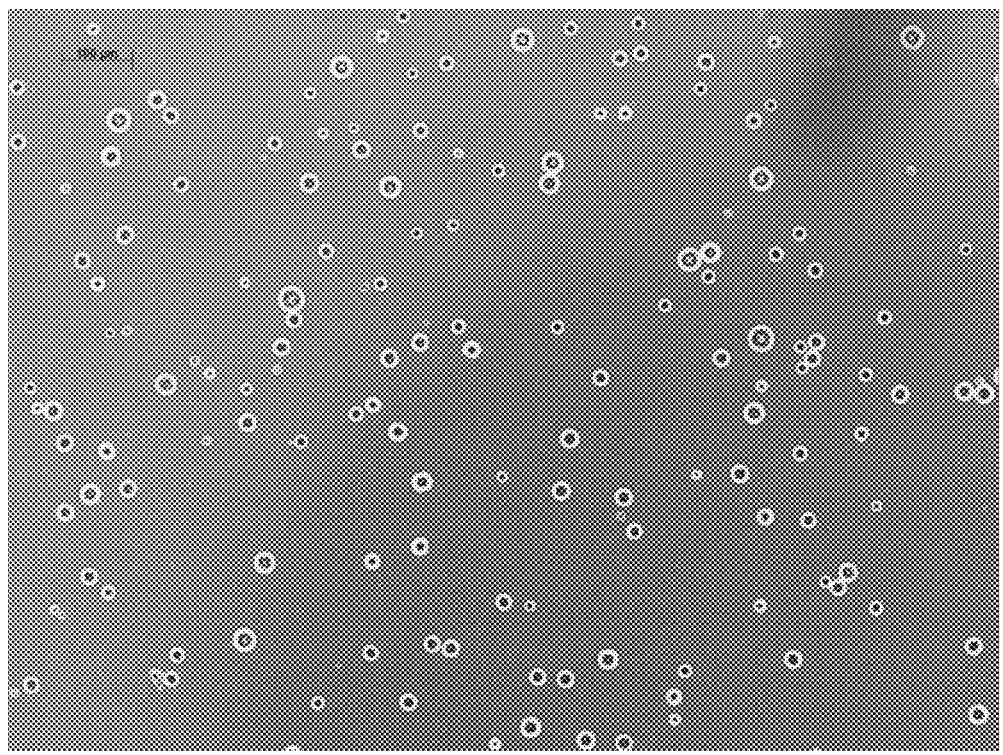
FIG. 4B is an optical microscopy image of a population of capsules in accordance with embodiments of the disclosure.
Figure 5A:
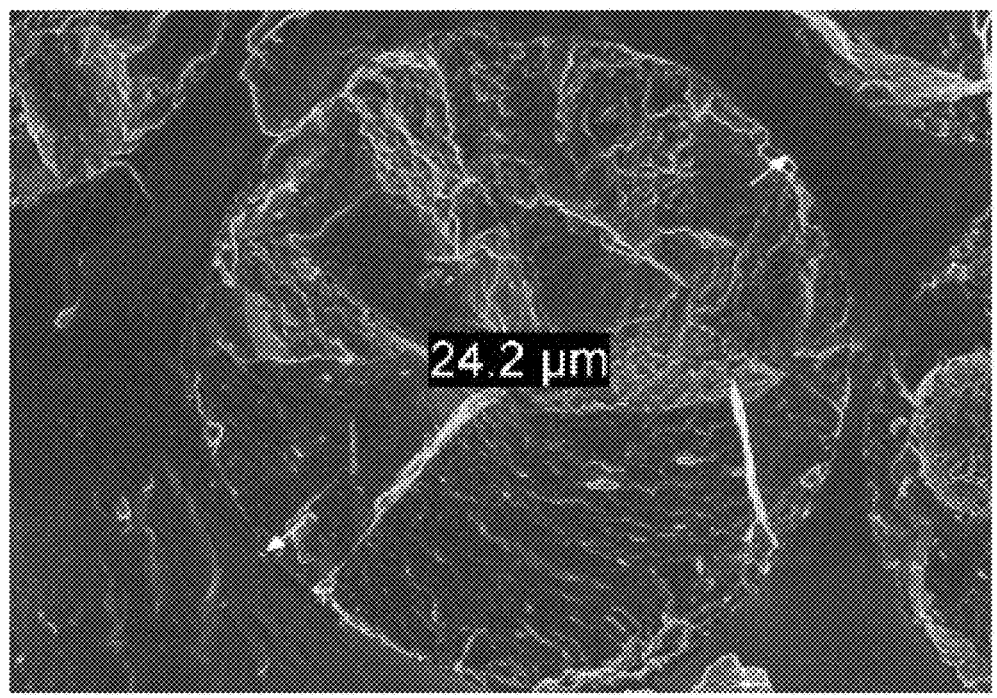
FIG. 5A is a cryo-scanning electron microscopy image of a capsule in accordance with embodiments of the disclosure, illustrating the diameter of the capsule is 24.2 μm (the white arrows indicate the two end points of the diameter measurement)
Figure 5B:
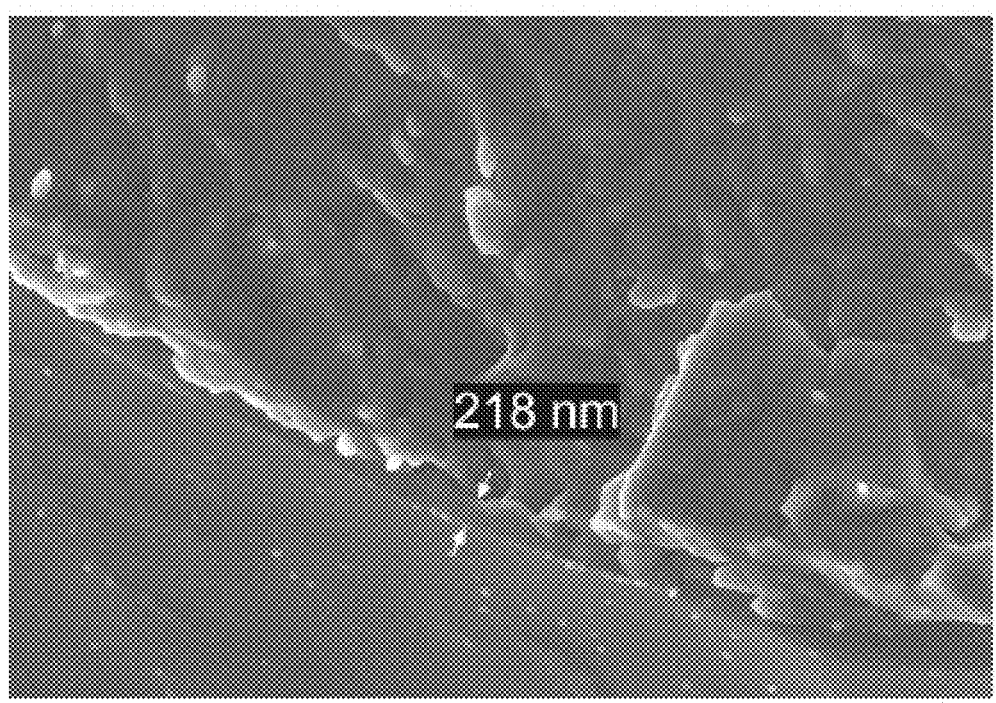
FIG. 5B is a cryo-scanning electron microscopy image of the capsules of FIG. 5A, illustrating the shell thickness of the capsule is 218 nm (the white arrows indicate the two end points of the shell thickness measurement)
Figure 6A:
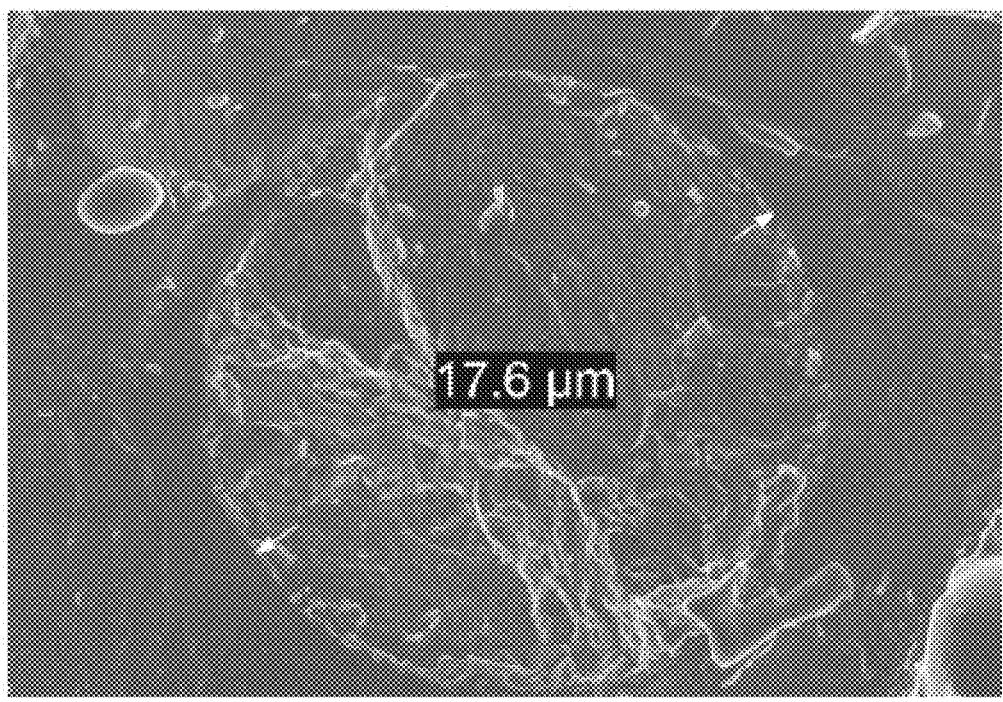
FIG. 6A is a cryo-scanning electron microscopy image of a capsule in accordance with embodiments of the disclosure, illustrating the diameter of the capsule is 17.6 µm (the white arrows indicate the two end points of the diameter measurement)
Figure 6B:
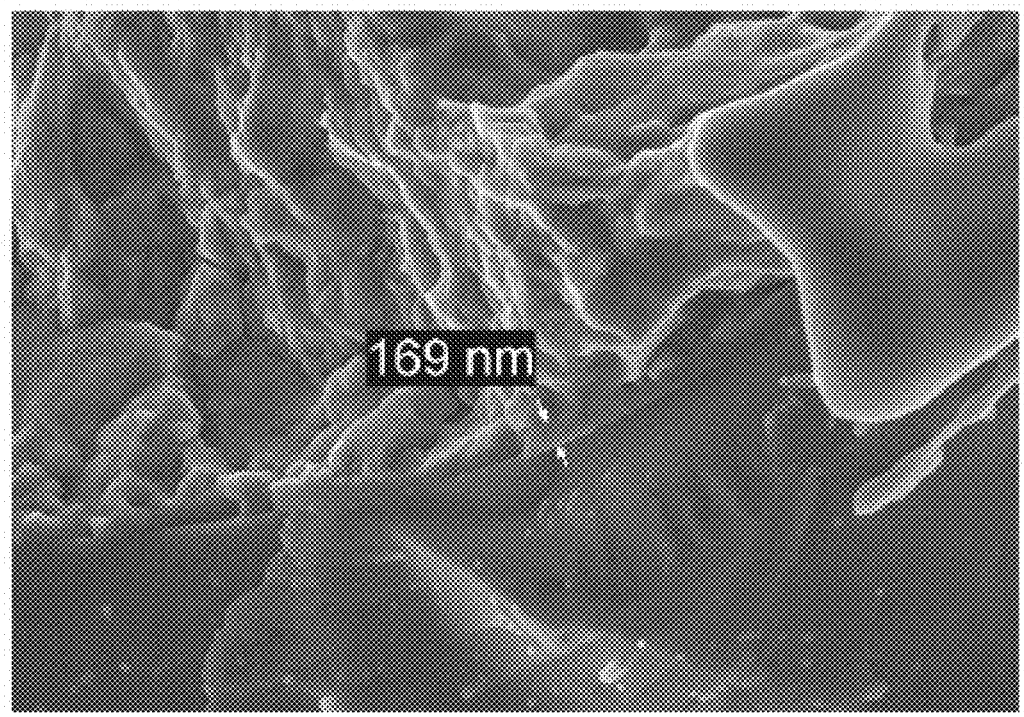
FIG. 6B is a cryo-scanning electron microscopy image of the capsule of FIG. 6A, illustrating the shell thickness of the capsule is 169 nm (the white arrows indicate the two end points of the shell thickness measurement)
Figure 7A:
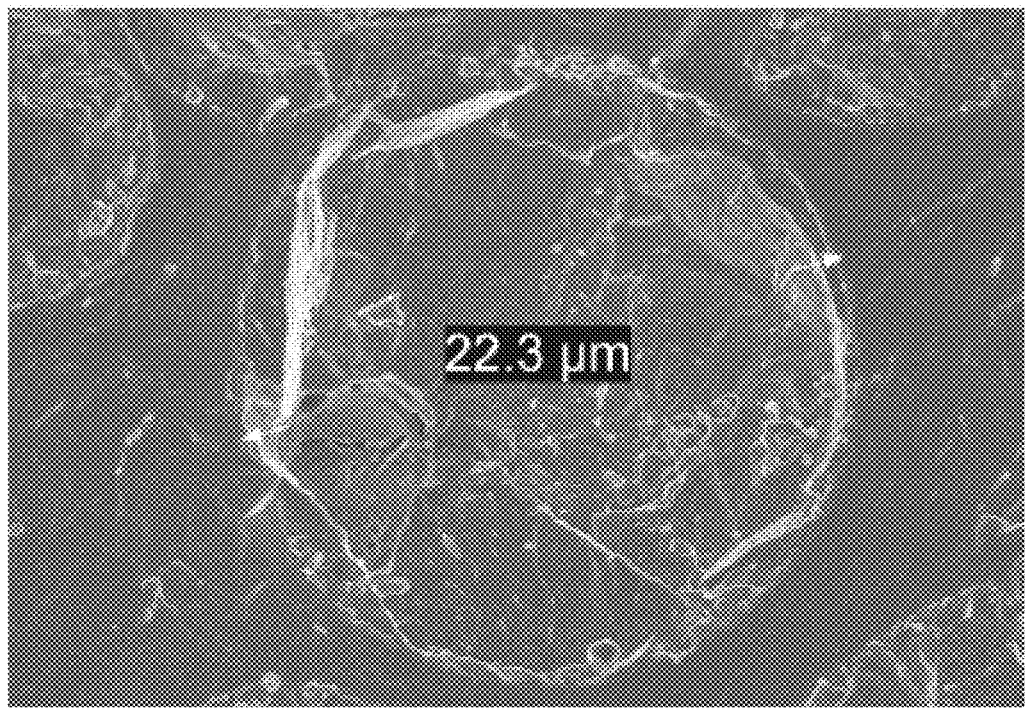
FIG. 7A is a cryo-scanning electron microscopy image of a capsule in accordance with embodiments of the disclosure, illustrating the diameter of the capsule is 22.3 µm (the white arrows indicate the two end points of the diameter measurement)
Figure 7B:
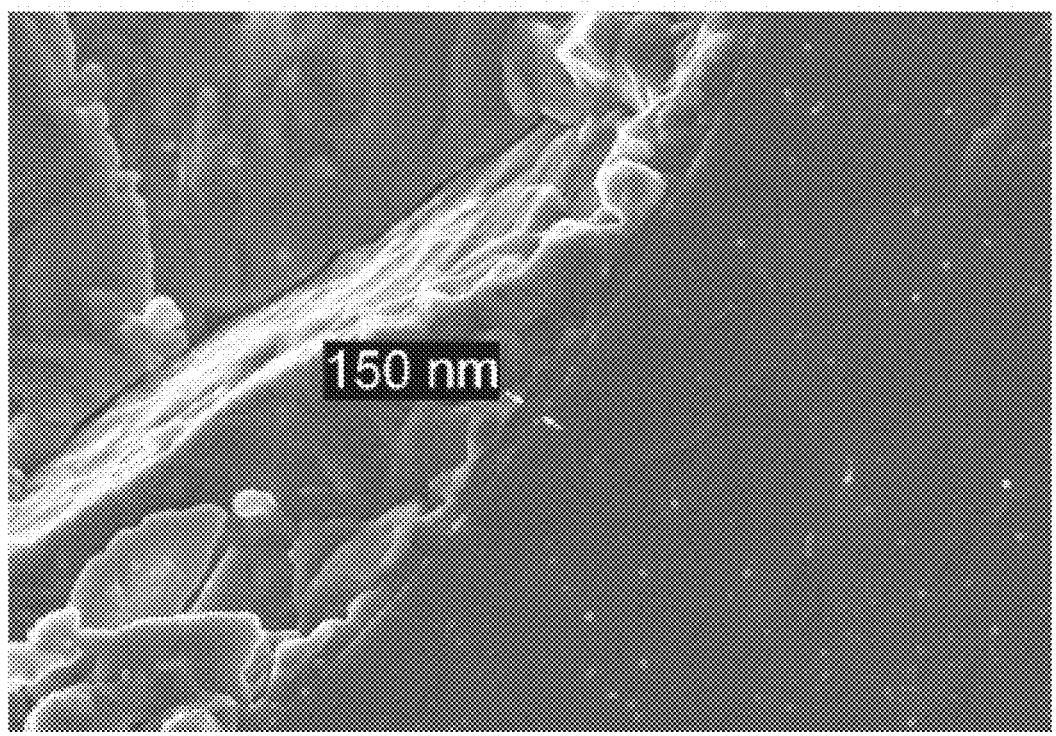
FIG. 7B is a cryo-scanning electron microscopy image of the capsule of FIG. 7A, illustrating the shell thickness of the capsule is 150 nm (the white arrows indicate the two end points of the shell thickness measurement)
Figure 8A:
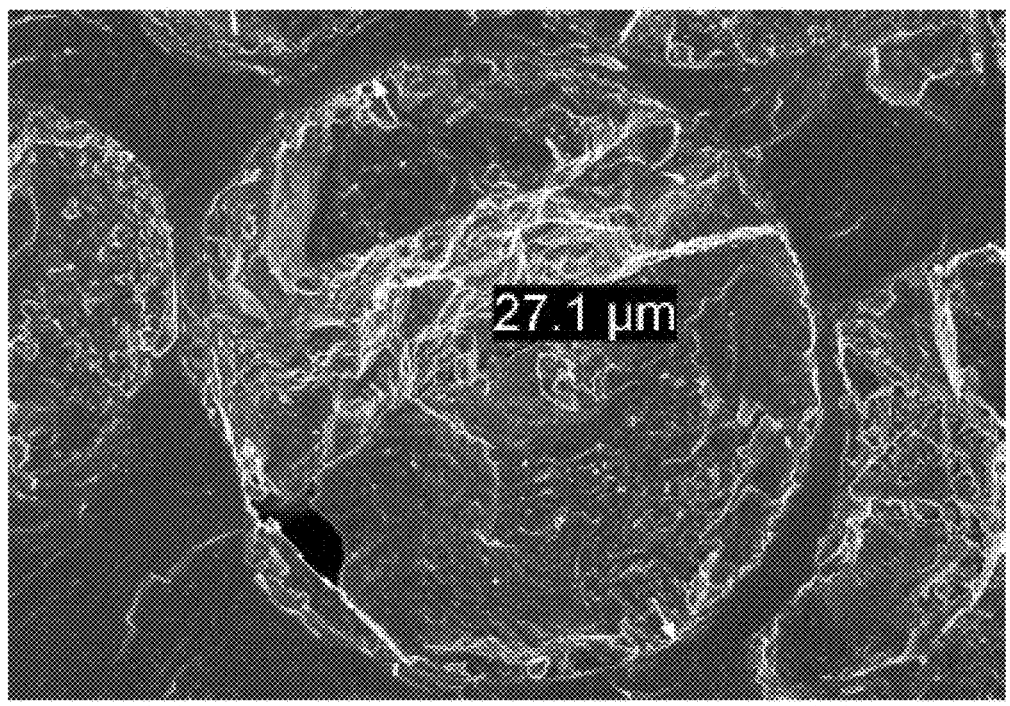
FIG. 8A is a cryo-scanning electron microscopy image of a capsule in accordance with embodiments of the disclosure, illustrating the diameter of the capsule is 27.1 µm (the white arrows indicate the two end points of the diameter measurement)
Figure 8B:
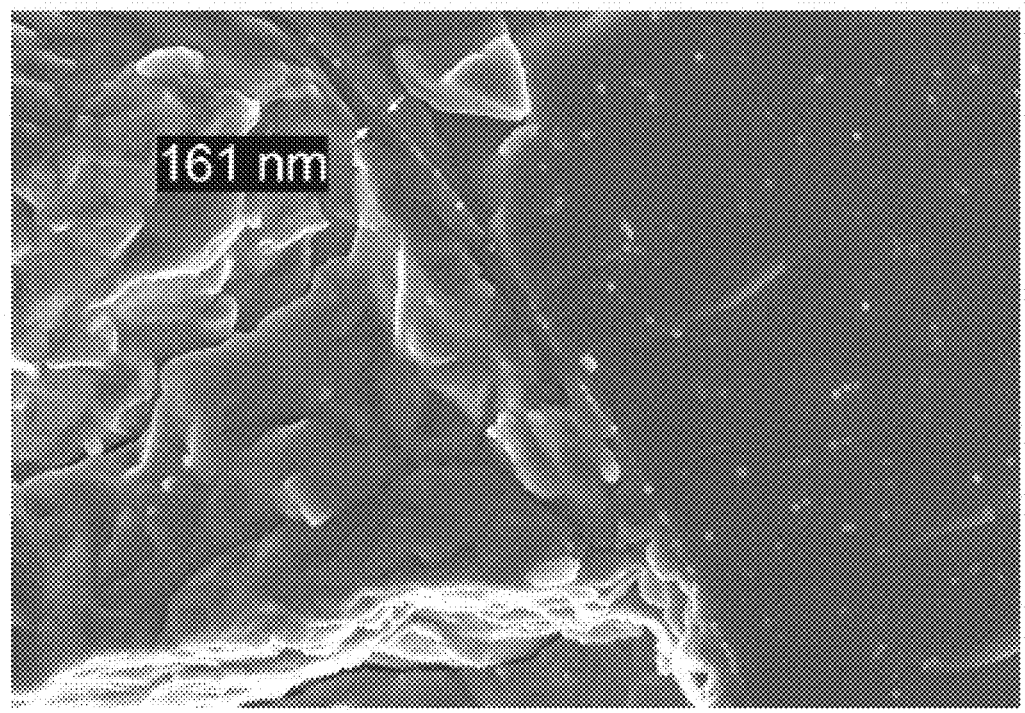
FIG. 8B is a cryo-scanning electron microscopy image of the capsule of FIG. 8A, illustrating the shell thickness of the capsule is 161 nm (the white arrows indicate the two end points of the shell thickness measurement)
Figure 9A:
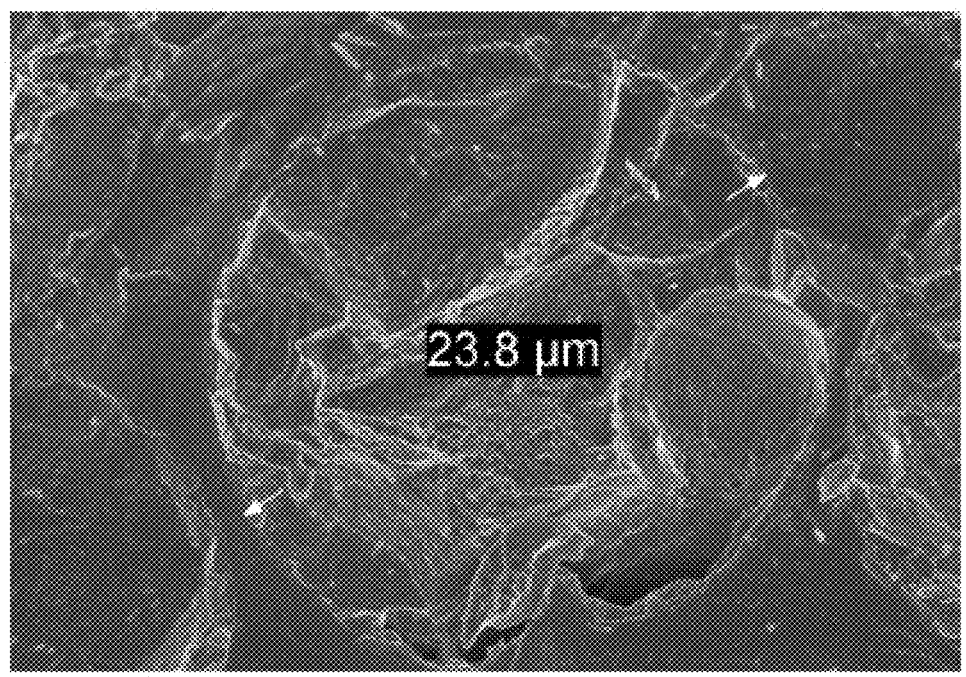
FIG. 9A is a cryo-scanning electron microscopy image of a capsule in accordance with embodiments of the disclosure, illustrating the diameter of the capsule is 23.8 µm (the white arrows indicate the two end points of the diameter measurement)
Figure 9B:
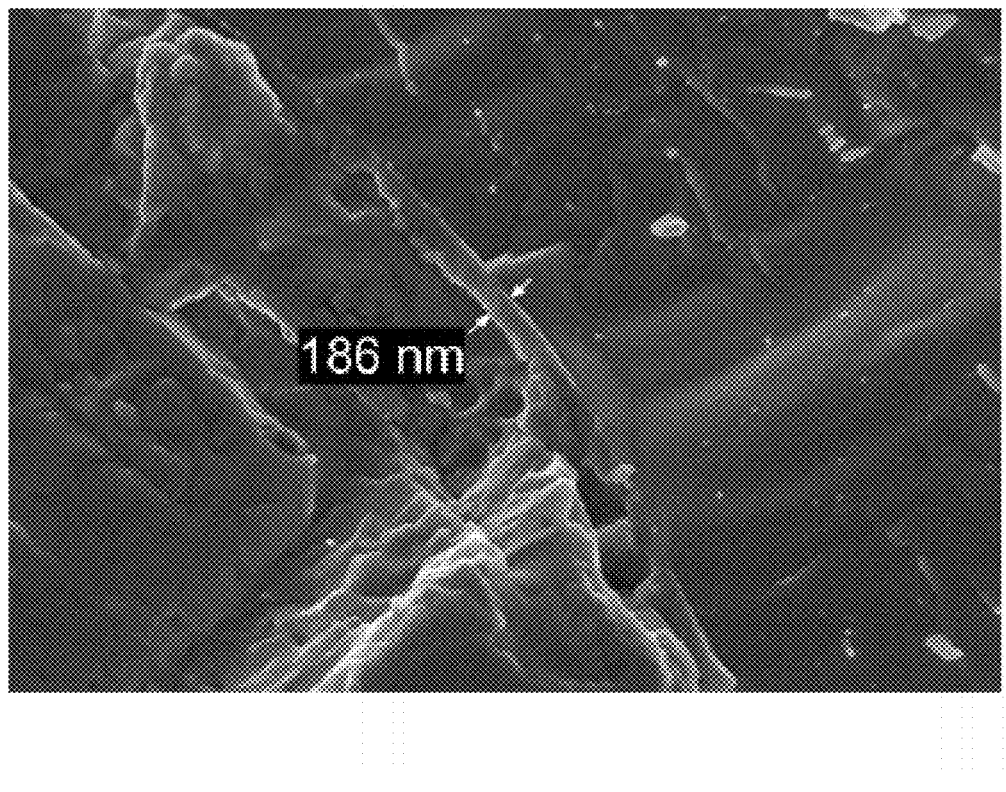
FIG. 9B is a cryo-scanning electron microscopy image of the capsule of FIG. 9A, illustrating the shell thickness of the capsule is 186 nm (the white arrows indicate the two end points of the shell thickness measurement)
Figure 10A:
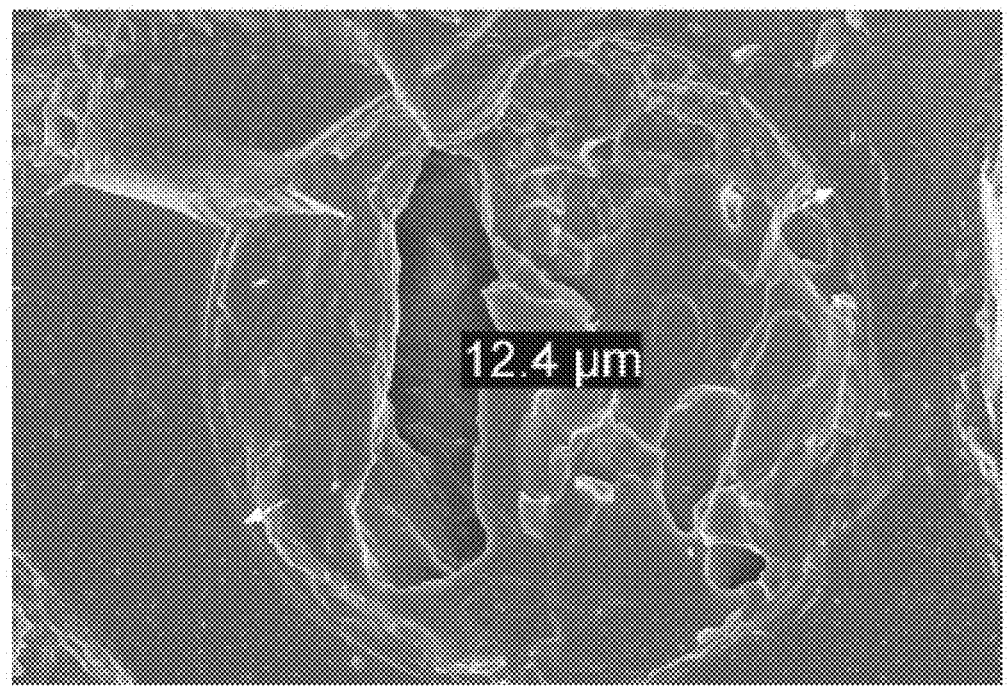
FIG. 10A is a cryo-scanning electron microscopy image of a capsule in accordance with embodiments of the disclosure, illustrating the diameter of the capsule is 12.4 µm (the white arrows indicate the two end points of the diameter measurement)
Figure 10B:
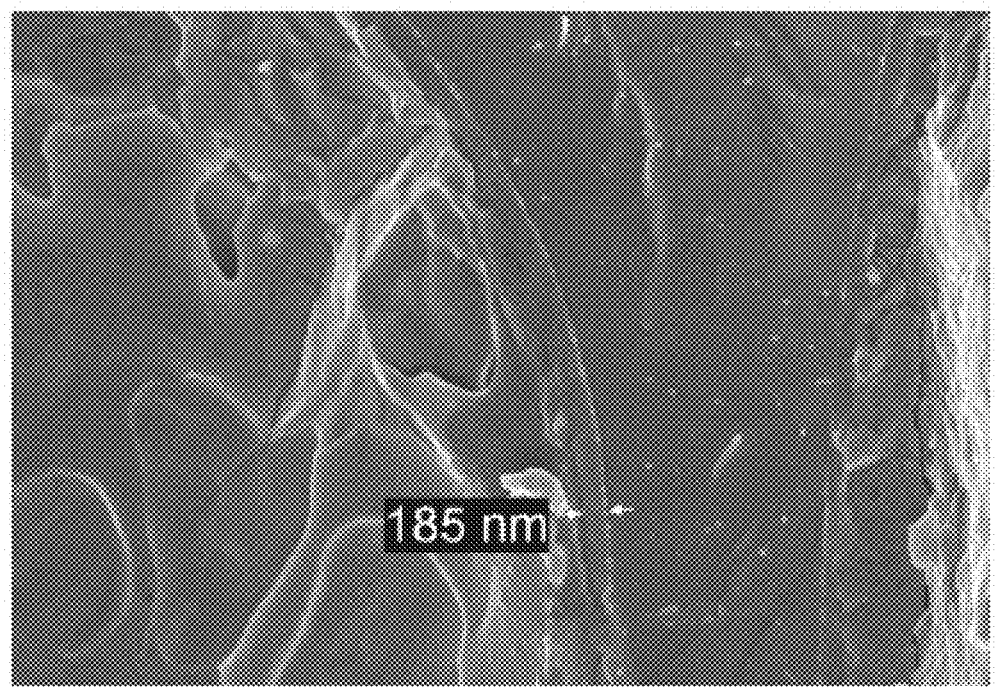
FIG. 10B is a cryo-scanning electron microscopy image of a capsule of FIG. 10A, illustrating the shell thickness of the capsule is 185 nm (the white arrows indicate the two end points of the shell thickness measurement)
Figure 11A:
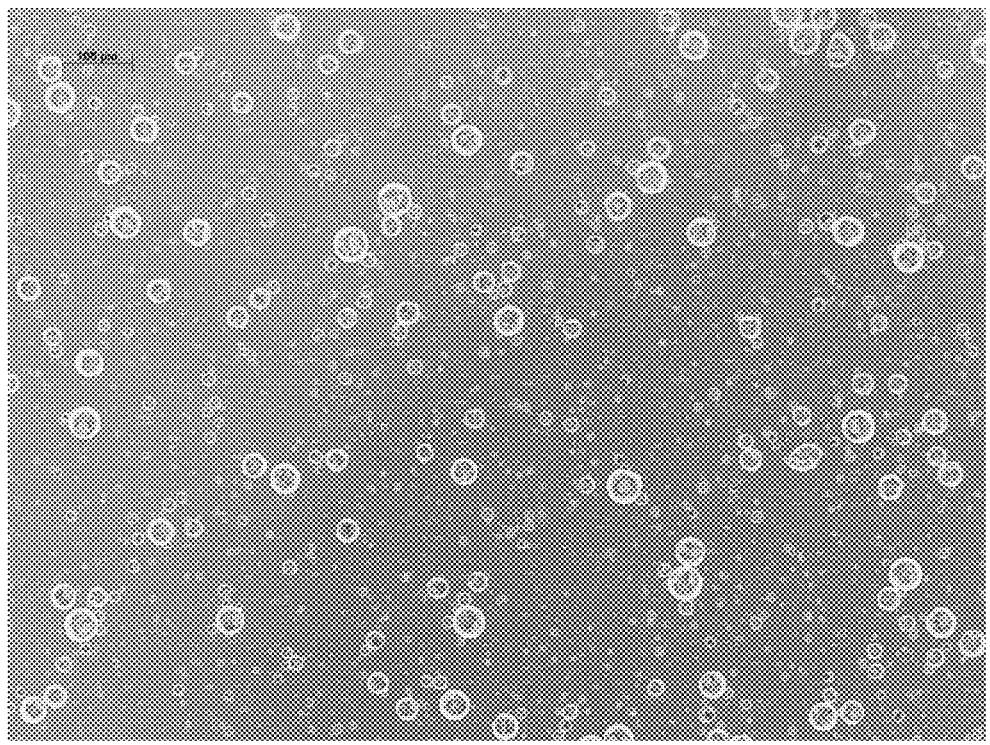
FIG. 11A is a comparative example of an optical microscopy image of a population of capsules not in accordance with embodiments of the disclosure.
Figure 11B:
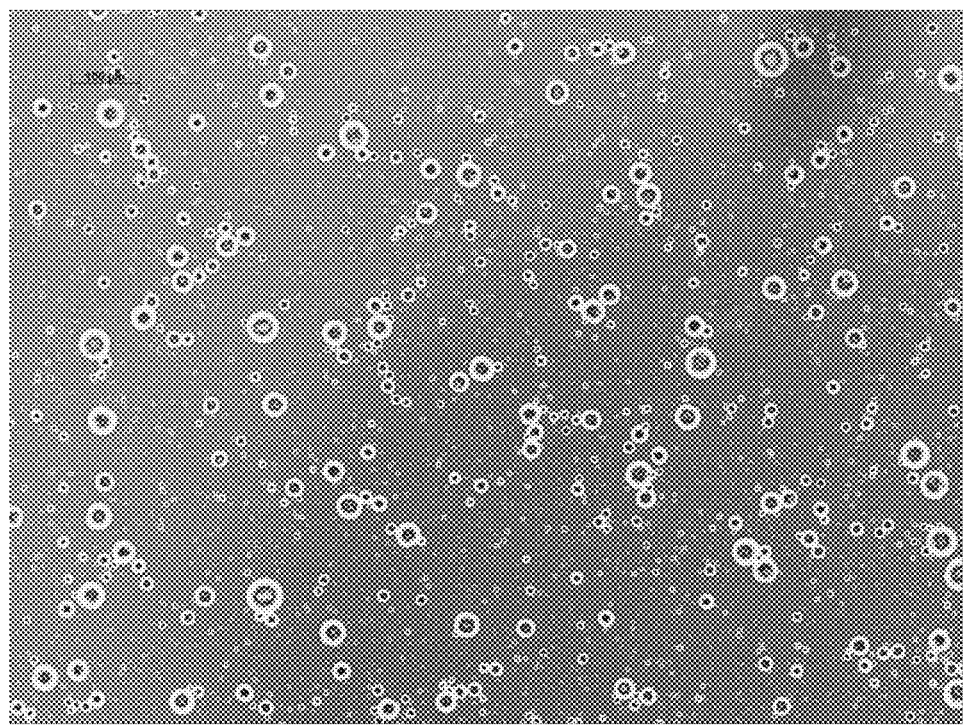
FIG. 11B is a comparative example of an optical microscopy image of a population of capsules not in accordance with embodiments of the disclosure.
Figure 12A:
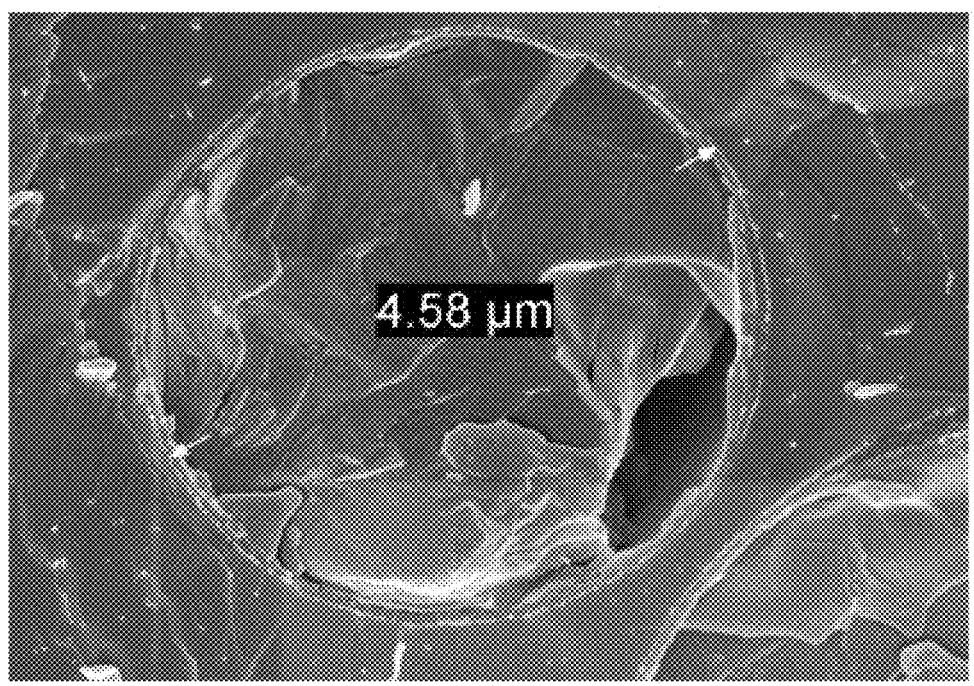
FIG. 12A is a cryo-scanning electron microscopy image of a capsule prepared in accordance with conventional batch methods as described in the comparative examples, illustrating the diameter of the capsule is 4.58 µm (the white arrows indicate the two end points of the diameter measurement)
Figure 12B:
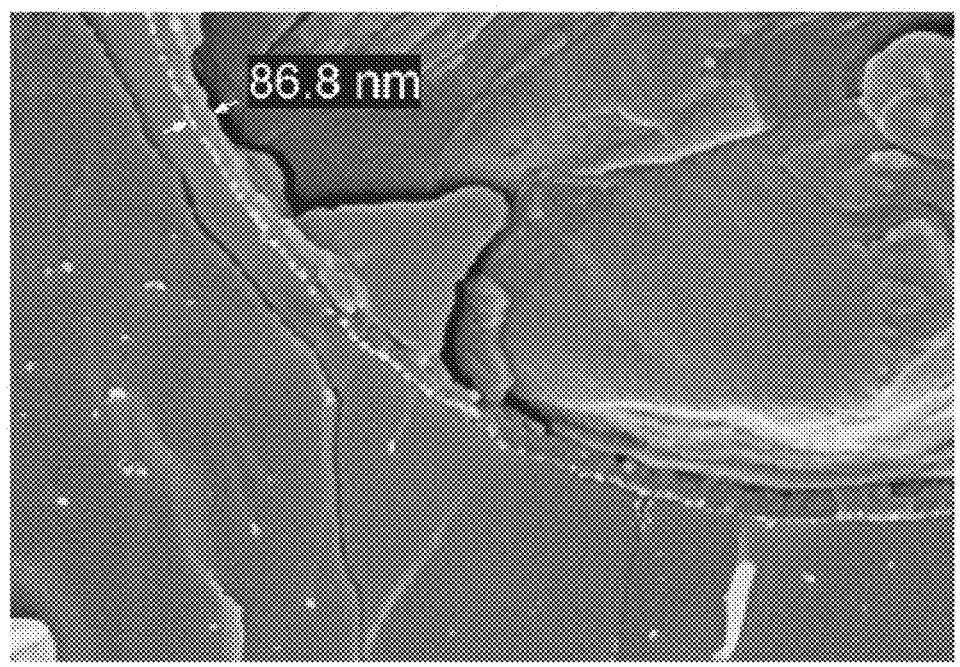
FIG. 12B is a cryo-scanning electron microscopy image of the capsule of FIG. 12A, illustrating the shell thickness of the capsule is 86.8 nm (the white arrows indicate the two end points of the shell thickness measurement)
Figure 13A:
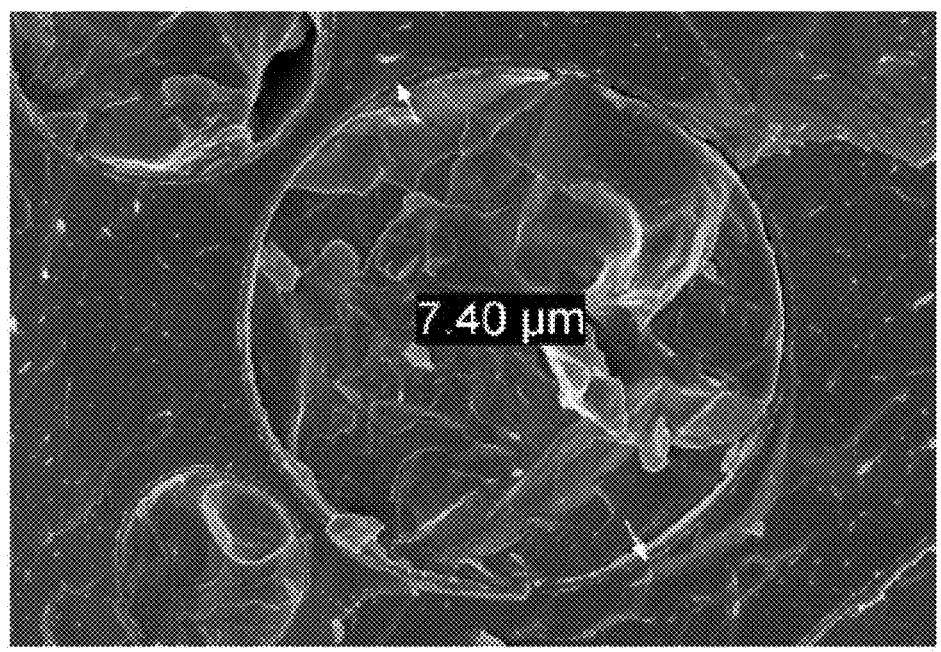
FIG. 13A is a cryo-scanning electron microscopy image of a capsule prepared by conventional batch processing in accordance with the comparative examples, illustrating the diameter of the capsule is 7.40 µm (the white arrows indicate the two end points of the diameter measurement)
Figure 13B:
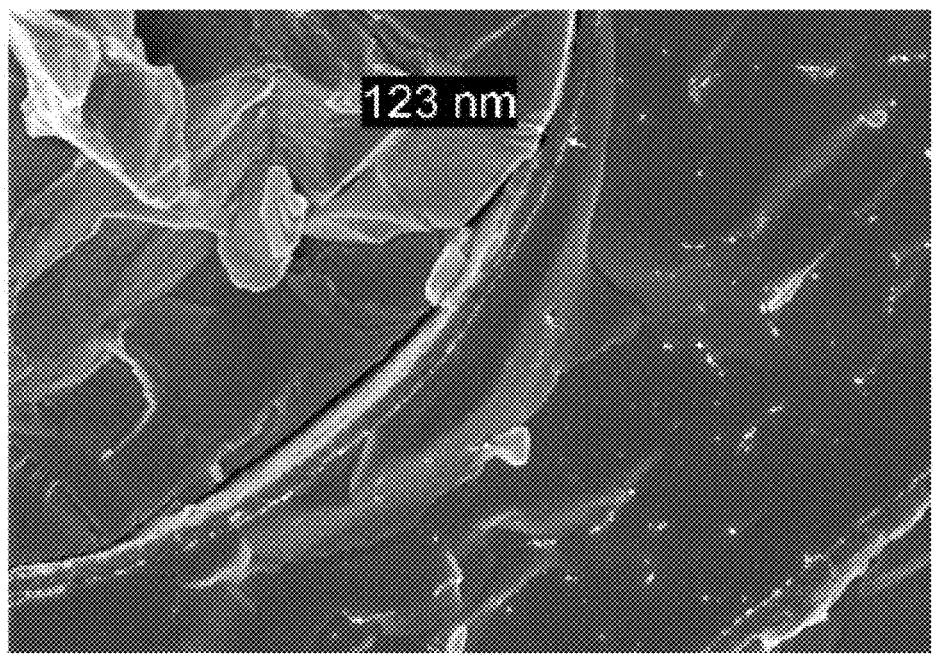
FIG. 13B is a cryo-scanning electron microscopy image of the capsule of FIG. 13A, illustrating the shell thickness of the capsule is 123 nm (the white arrows indicate the two end points of the shell thickness measurement)
Figure 14A:
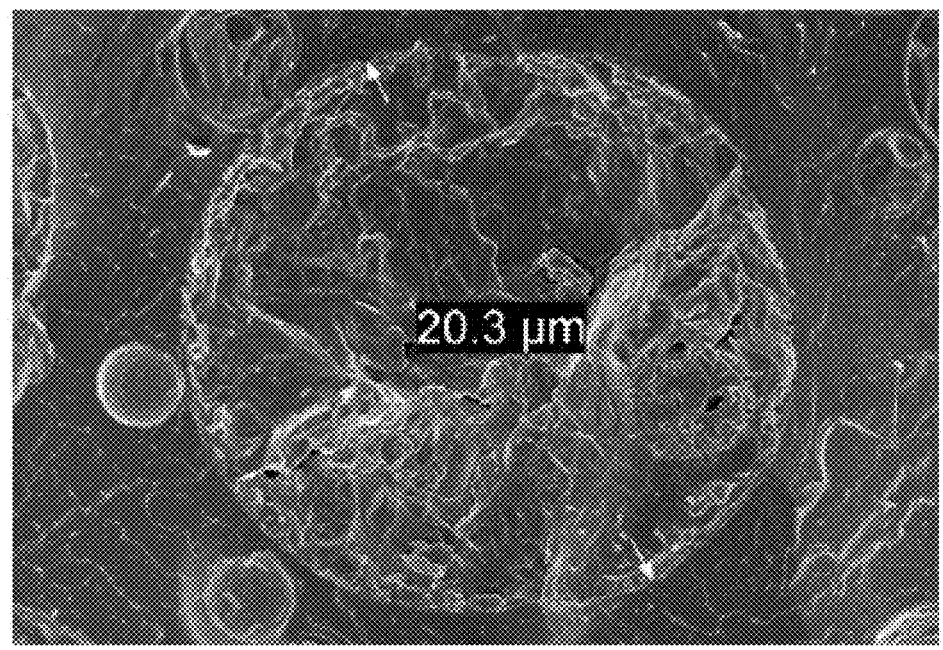
FIG. 14A is a cryo-scanning electron microscopy image of a capsule prepared by conventional batch processing in accordance with the comparative examples, illustrating the diameter of the capsule is 20.3 µm (the white arrows indicate the two end points of the diameter measurement)
Figure 14B:
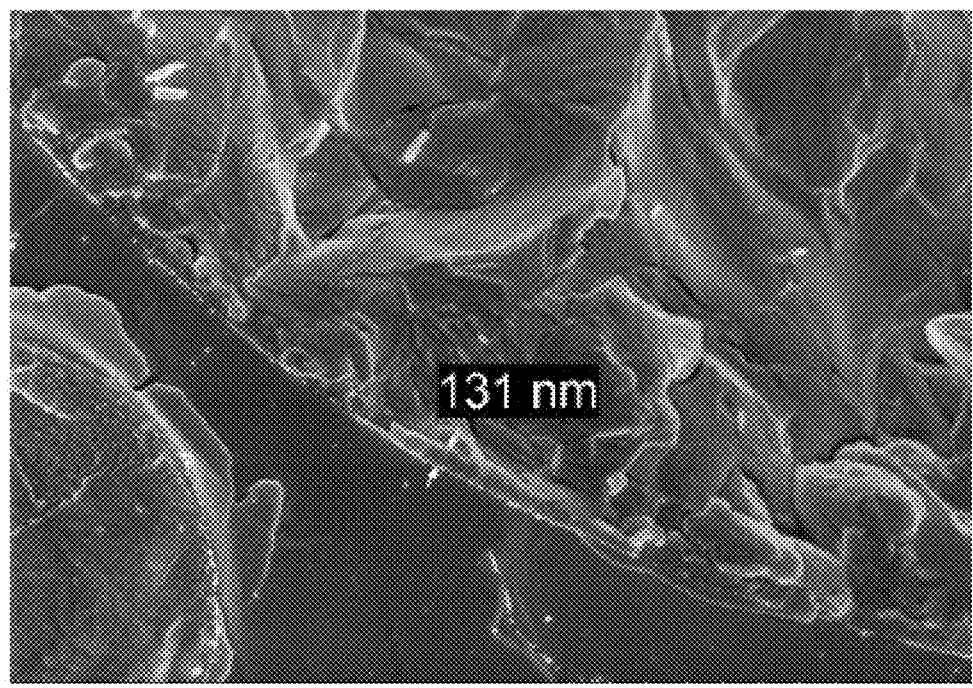
FIG. 14B is a cryo-scanning electron microscopy image of the capsule of FIG. 14A, illustrating the shell thickness of the capsule is 131 nm (the white arrows indicate the two end points of the shell thickness measurement)
Figure 15A:
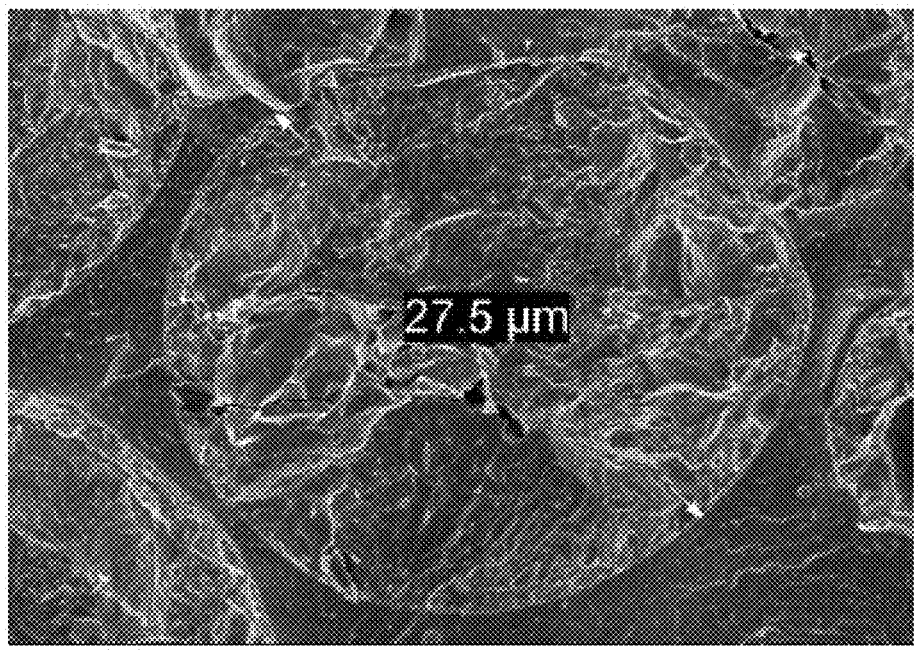
FIG. 15A is a cryo-scanning electron microscopy image of a capsule prepared by conventional batch processing in accordance with the comparative examples, illustrating the diameter of the capsule is 27.5 µm (the white arrows indicate the two end points of the diameter measurement)
Figure 15B:
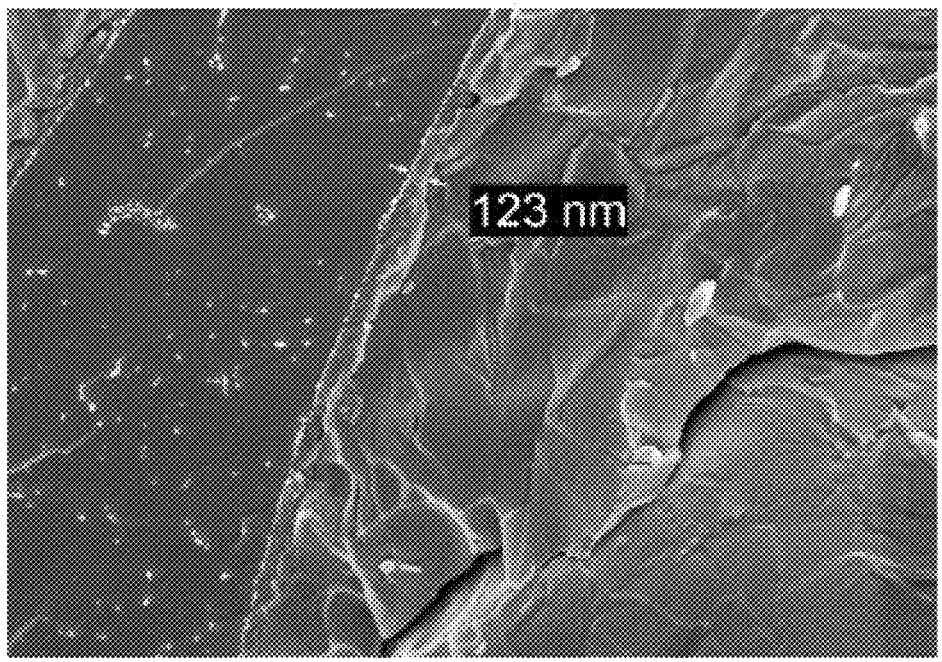
FIG. 15B is a cryo-scanning electron microscopy image of the capsule of FIG. 15A, illustrating the shell thickness of the capsule is 123 nm (the white arrows indicate the two end points of the shell thickness measurement)
Figure 16A:
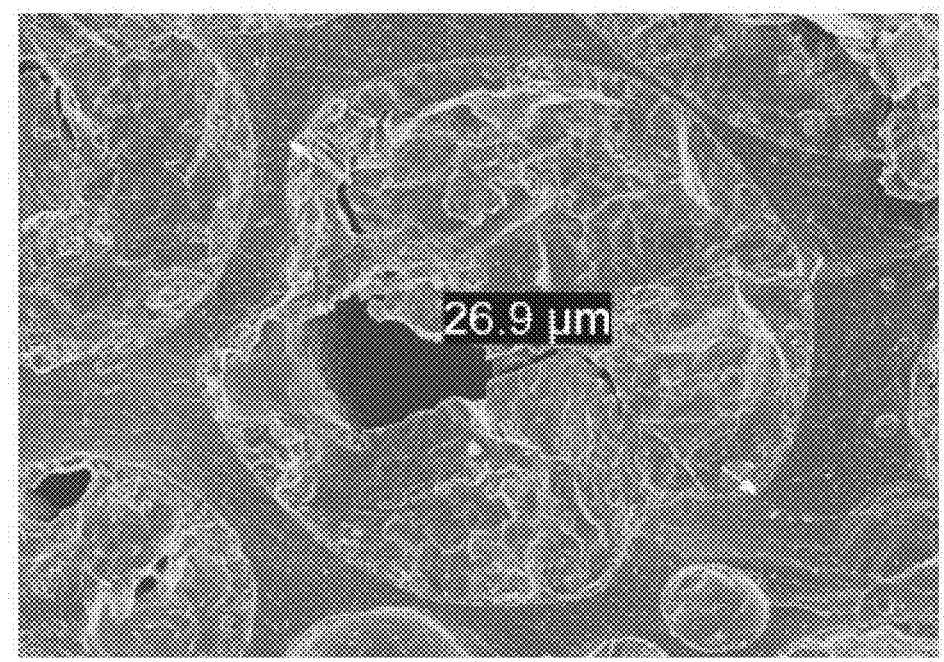
FIG. 16A is a cryo-scanning electron microscopy image of a capsule prepared by conventional batch processing in accordance with the comparative examples, illustrating the diameter of the capsule is 26.9 µm (the white arrows indicate the two end points of the diameter measurement)
Figure 16B:
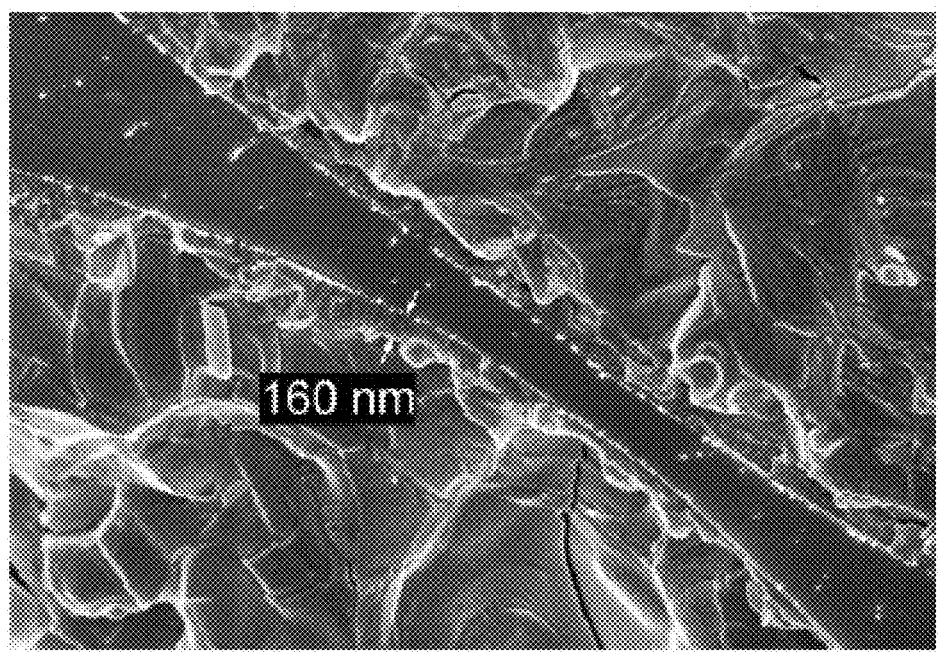
FIG. 16B is a cryo-scanning electron microscopy image of the capsule of FIG. 16A, illustrating the shell thickness of the capsule is 160 nm (the white arrows indicate the two end points of the shell thickness measurement)
Figure 17A:
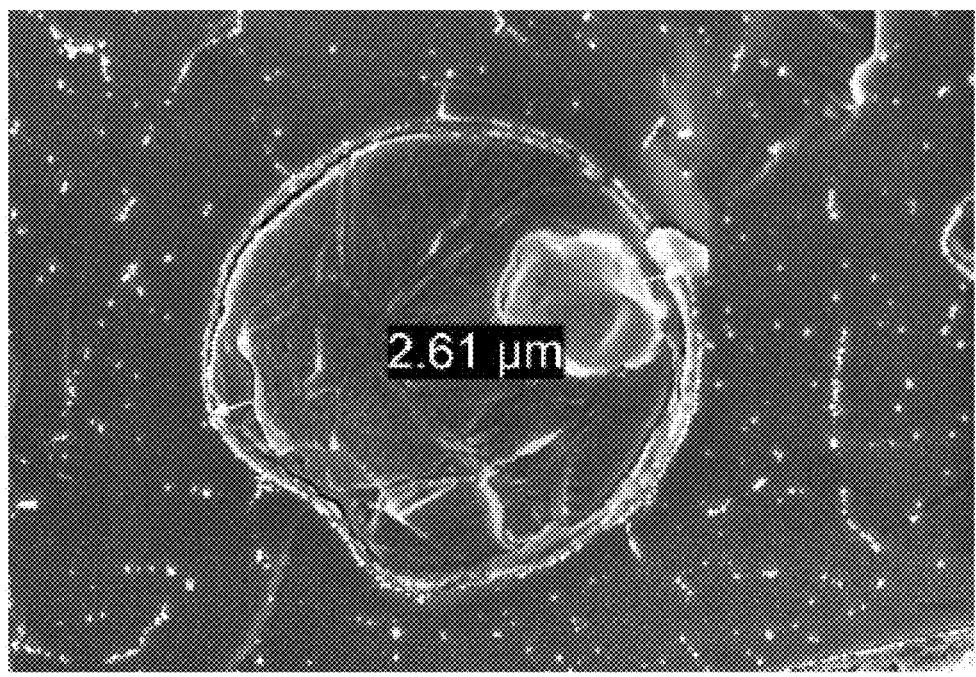
FIG. 17A is a cryo-scanning electron microscopy image of a capsule prepared by conventional batch processing in accordance with the comparative examples, illustrating the diameter of the capsule is 2.61 µm (the white arrows indicate the two end points of the diameter measurement)
Figure 17B:
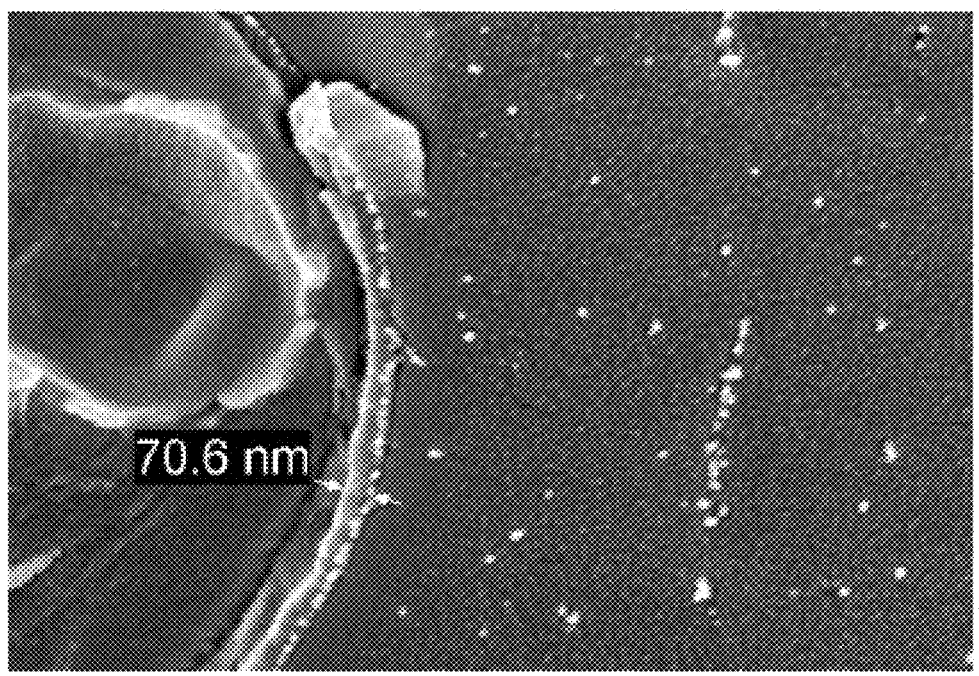
FIG. 17B is a cryo-scanning electron microscopy image of the capsule of FIG. 17A, illustrating the shell thickness of the capsule is 70.6 nm (the white arrows indicate the two end points of the shell thickness measurement)
Figure 18A:
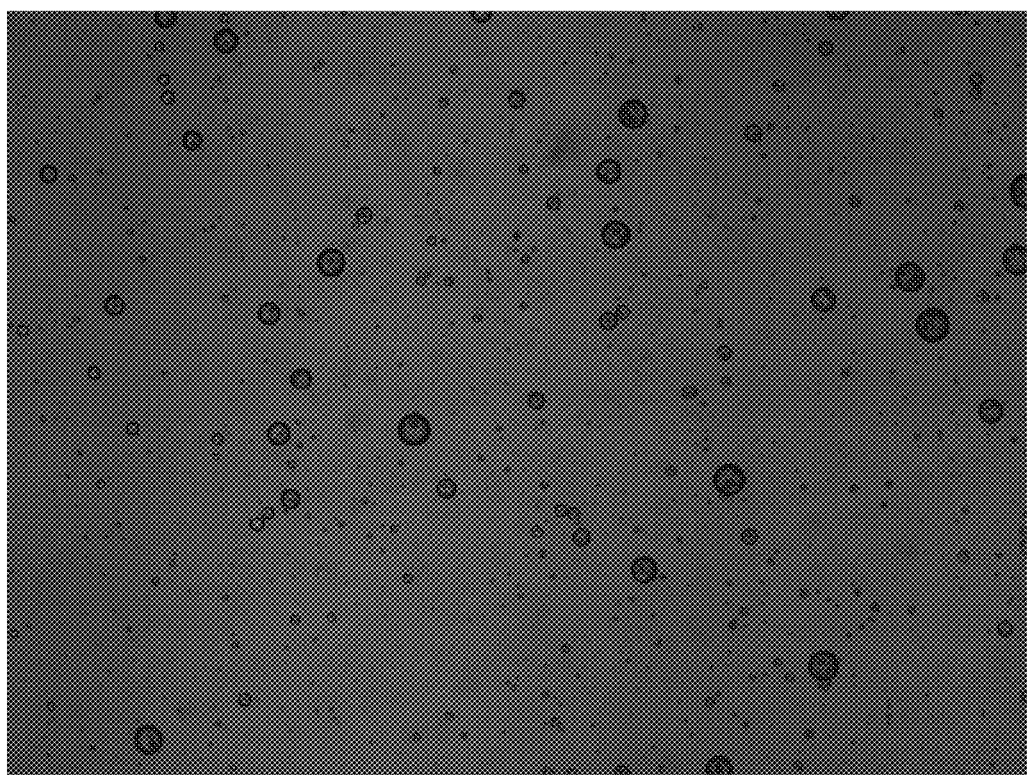
FIG. 18A is an optical microscopy image of a population of capsules not in accordance with embodiments of the disclosure.
Figure 18B:
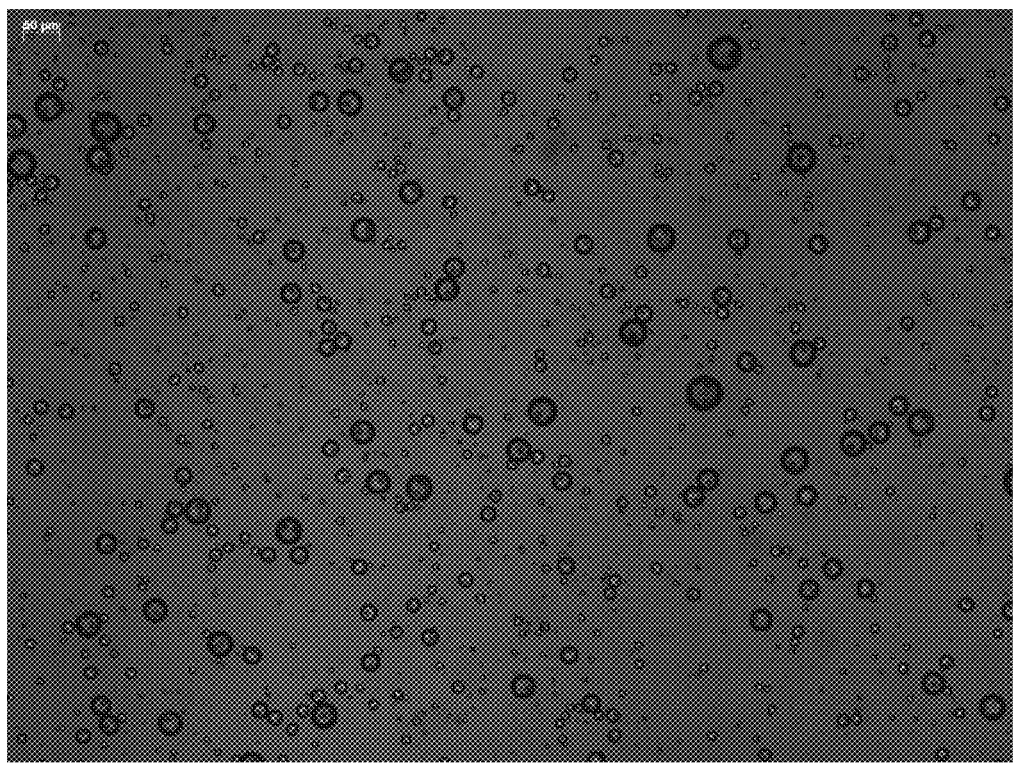
FIG. 18B is an optical microscopy image of a population of capsules not in accordance with embodiments of the disclosure.
Figure 19A:
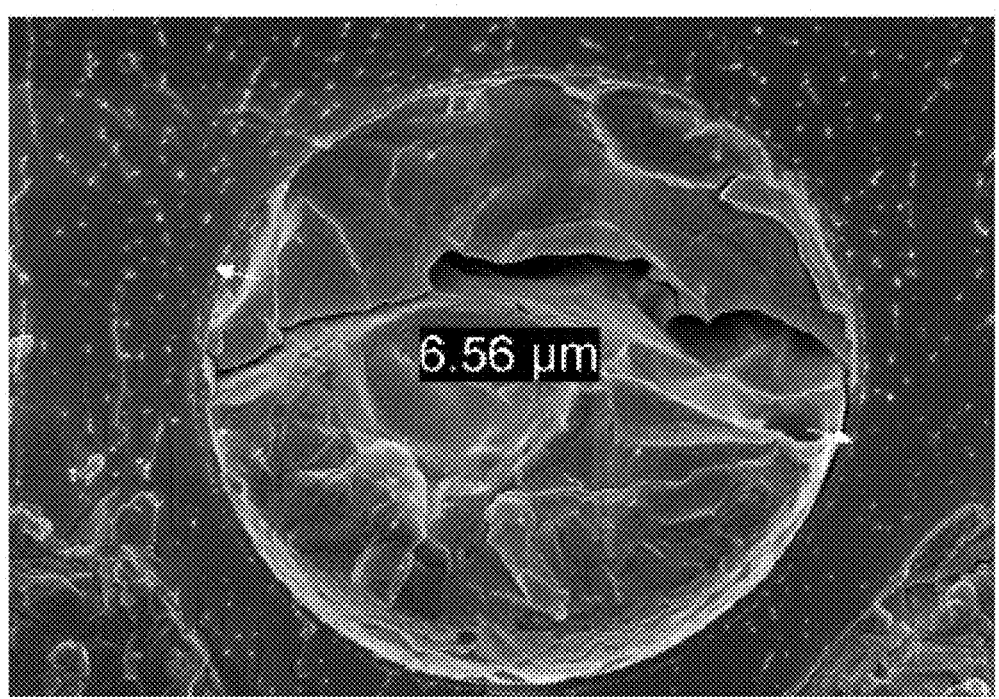
FIG. 19A is a cryo-scanning electron microscopy image of a capsule prepared by conventional batch processing in accordance with the comparative examples, illustrating the diameter of the capsule is 6.56 µm (the white arrows indicate the two end points of the diameter measurement)
Figure 19B:
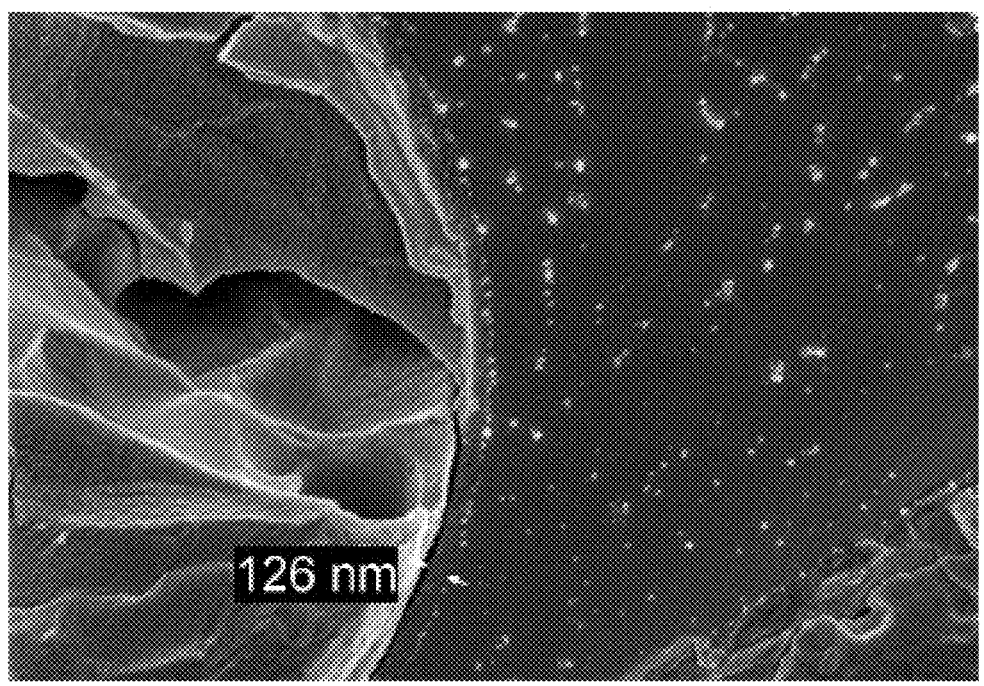
FIG. 19B is a cryo-scanning electron microscopy image of the capsule of FIG. 19A, illustrating the shell thickness of the capsule is 126 nm (the white arrows indicate the two end points of the shell thickness measurement)
Figure 20A:
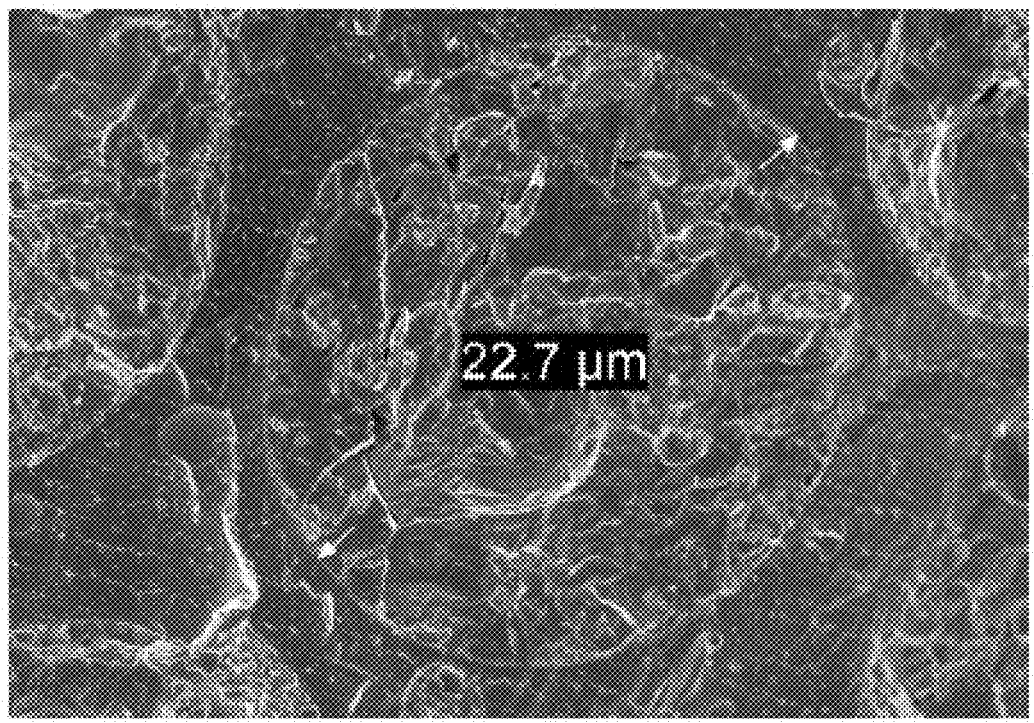
FIG. 20A is a cryo-scanning electron microscopy image of a capsule prepared by conventional batch processing in accordance with the comparative examples, illustrating the diameter of the capsule is 22.7 µm (the white arrows indicate the two end points of the diameter measurement)
Figure 20B:
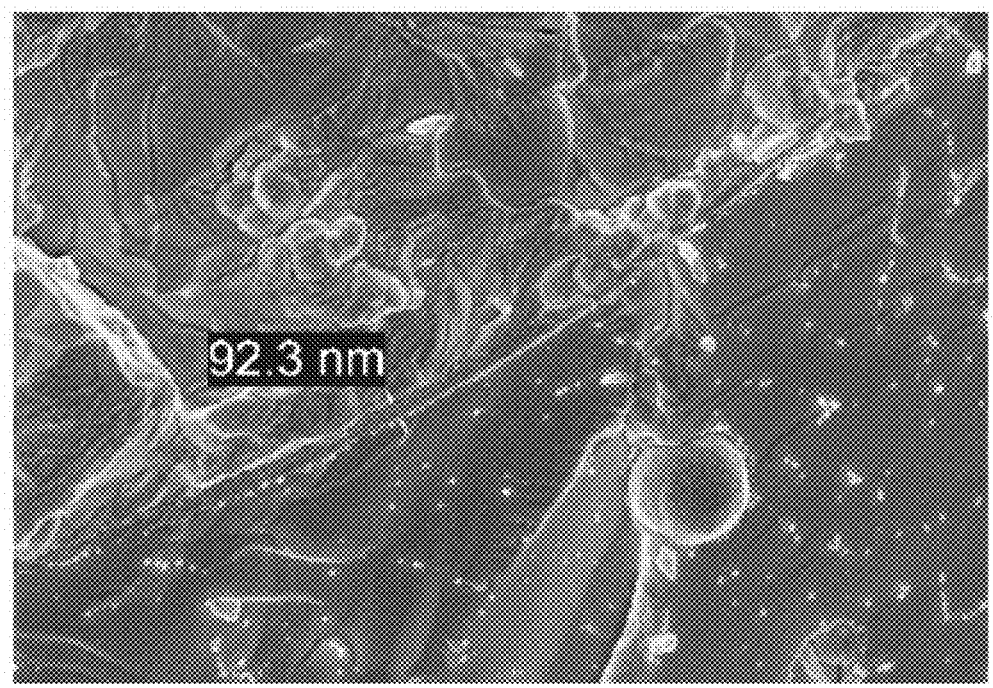
FIG. 20B is a cryo-scanning electron microscopy image of the capsule of FIG. 20A, illustrating the shell thickness of the capsule is 92.3 nm (the white arrows indicate the two end points of the shell thickness measurement)
Figure 21A:
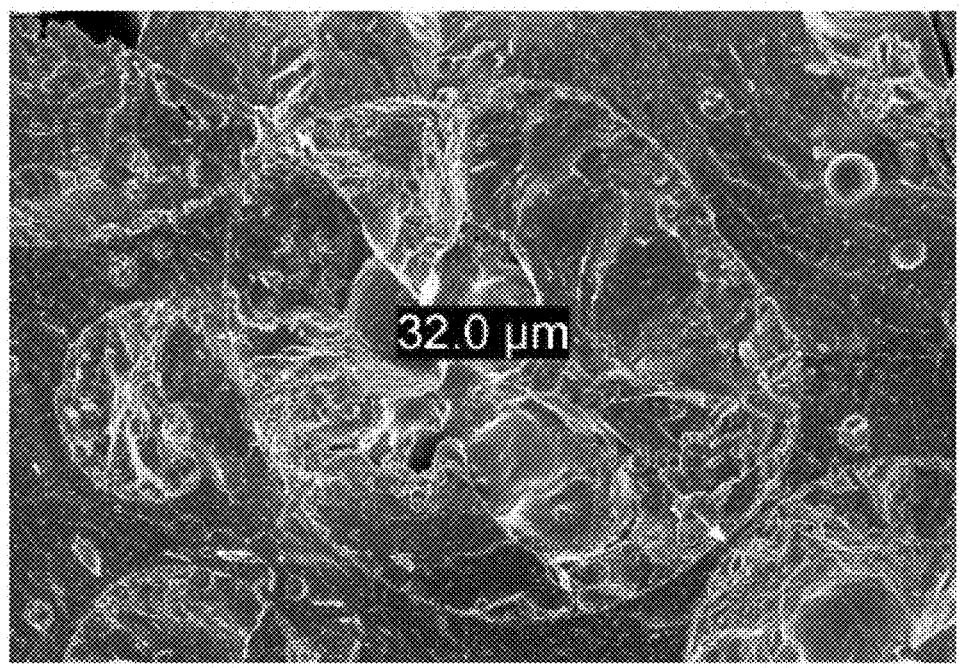
FIG. 21A is a cryo-scanning electron microscopy image of a capsule prepared by conventional batch processing in accordance with the comparative examples, illustrating the diameter of the capsule is 32.0 µm (the white arrows indicate the two end points of the diameter measurement)
Figure 21B:
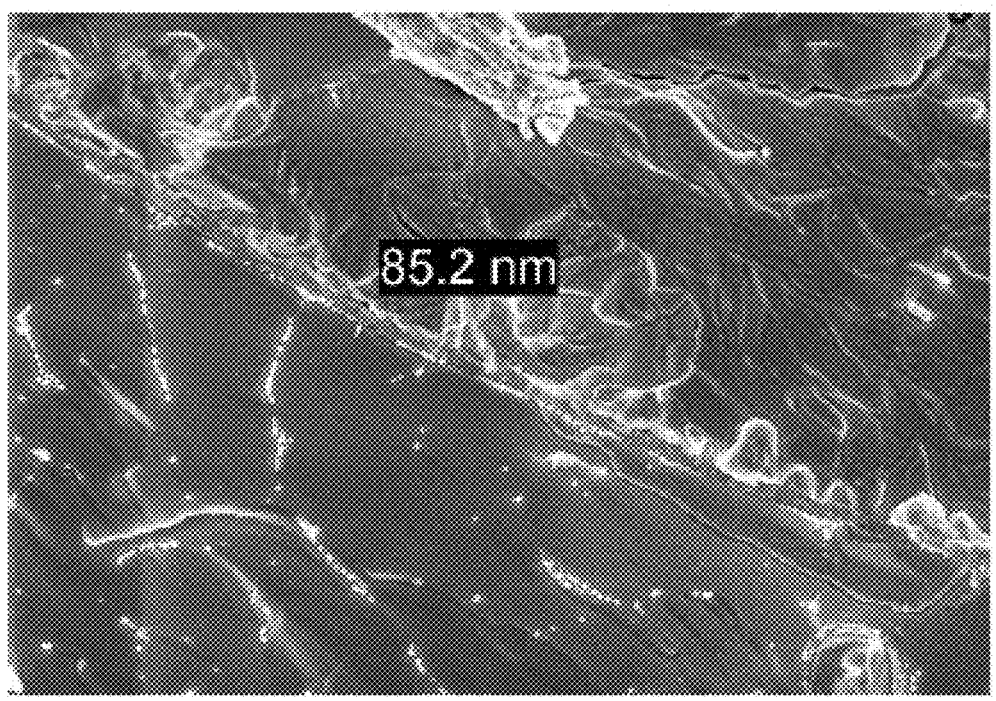
FIG. 21B is a cryo-scanning electron microscopy image of the capsule of FIG. 21A, illustrating the shell thickness of the capsule is 85.2 nm (the white arrows indicate the two end points of the shell thickness measurement)
Figure 22A:
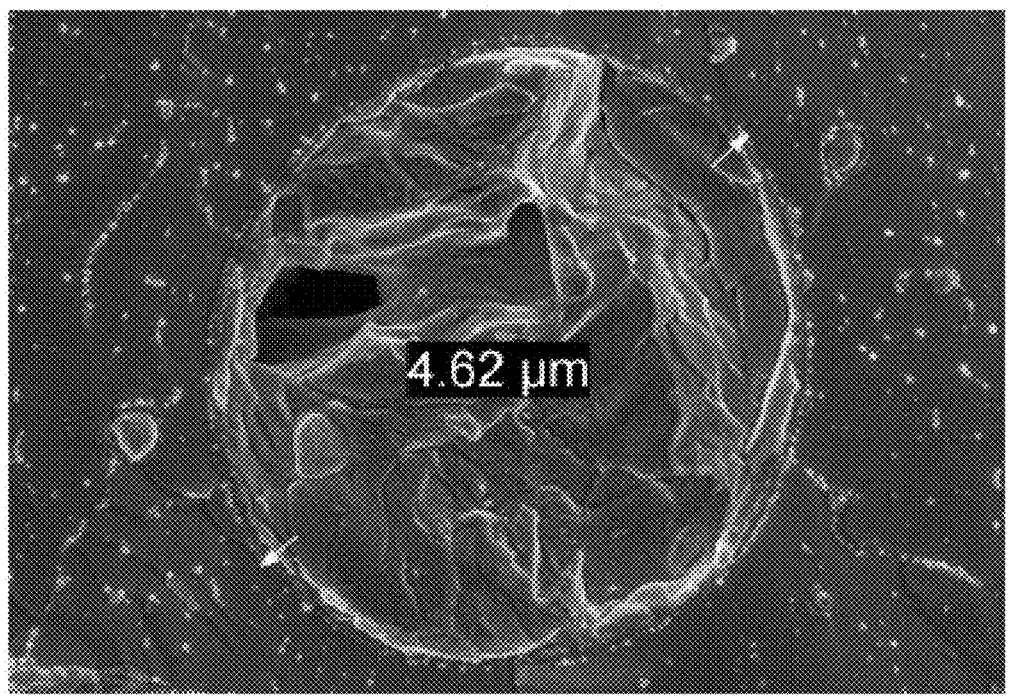
FIG. 22A is a cryo-scanning electron microscopy image of a capsule prepared by conventional batch processing in accordance with the comparative examples, illustrating the diameter of the capsule is 4.62 µm (the white arrows indicate the two end points of the diameter measurement)
Figure 22B:
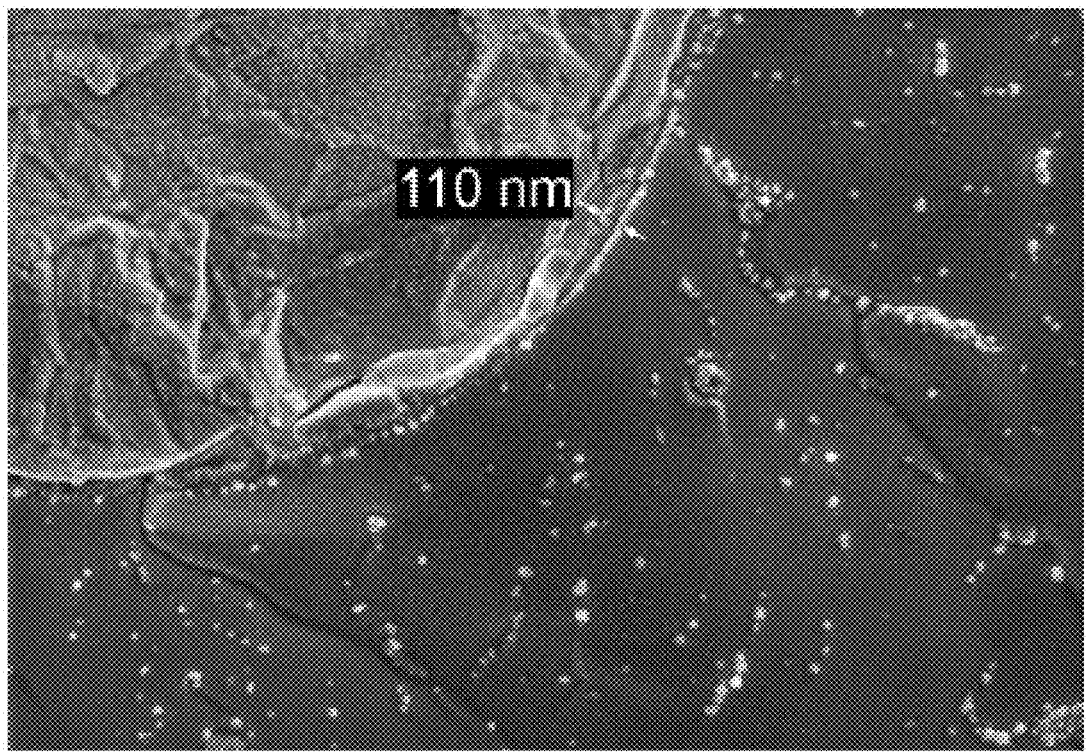
FIG. 22B is a cryo-scanning electron microscopy image of the capsule of FIG. 22A, illustrating the shell thickness of the capsule is 110 nm (the white arrows indicate the two end points of the shell thickness measurement)
Figure 23A:
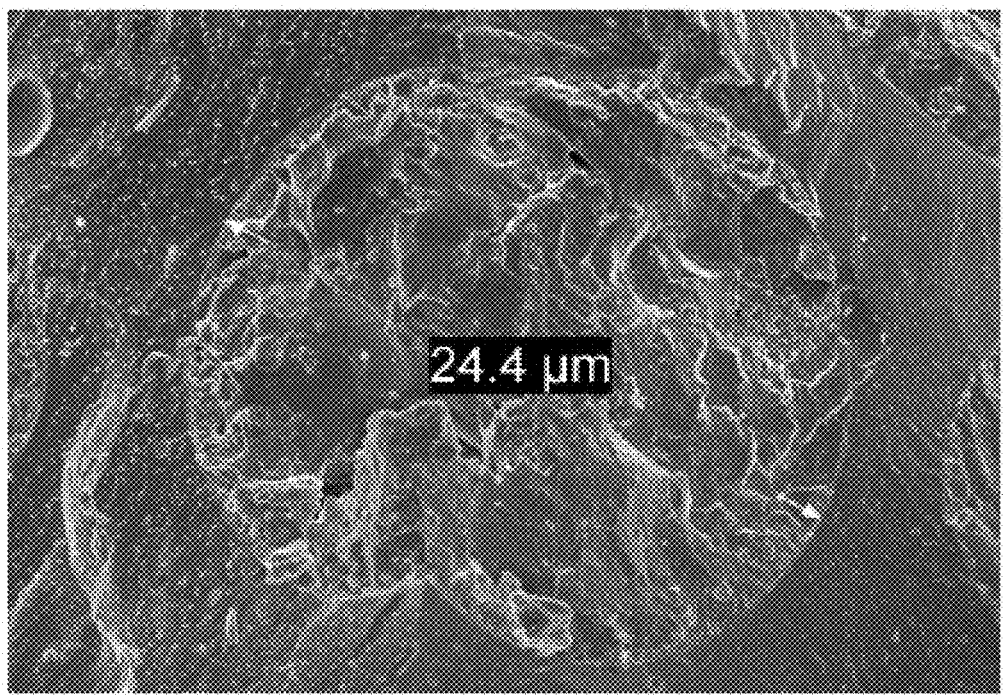
FIG. 23A is a cryo-scanning electron microscopy image of a capsule prepared by conventional batch processing in accordance with the comparative examples, illustrating the diameter of the capsule is 24.4 µm (the white arrows indicate the two end points of the diameter measurement)
Figure 23B:
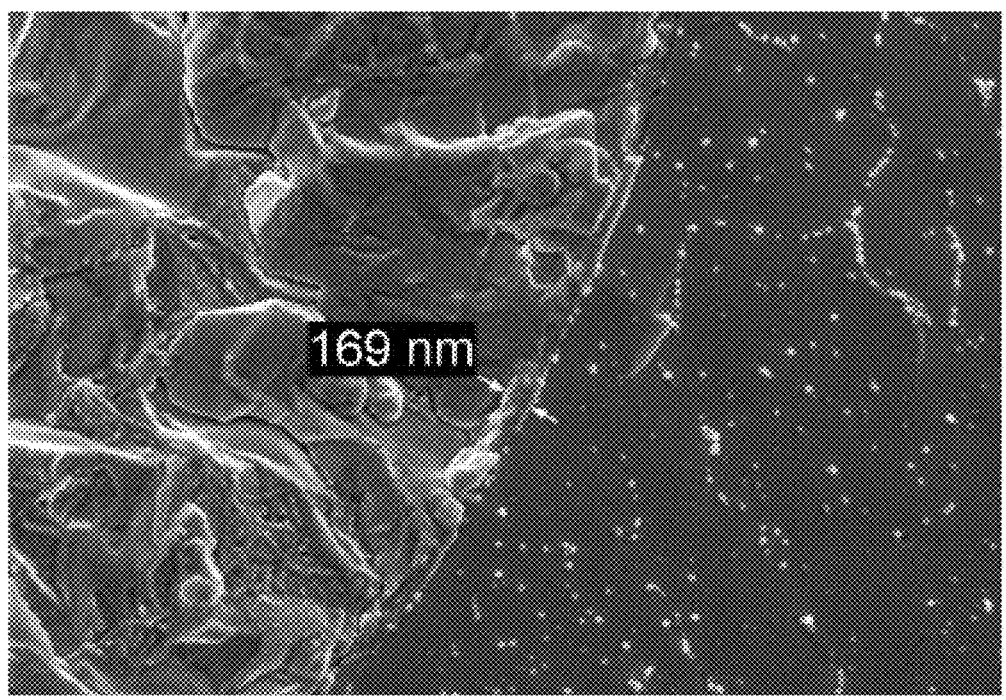
FIG. 23B is a cryo-scanning electron microscopy image of the capsule of FIG. 23A, illustrating the shell thickness of the capsule is 169 nm (the white arrows indicate the two end points of the shell thickness measurement)
Figure 24A:
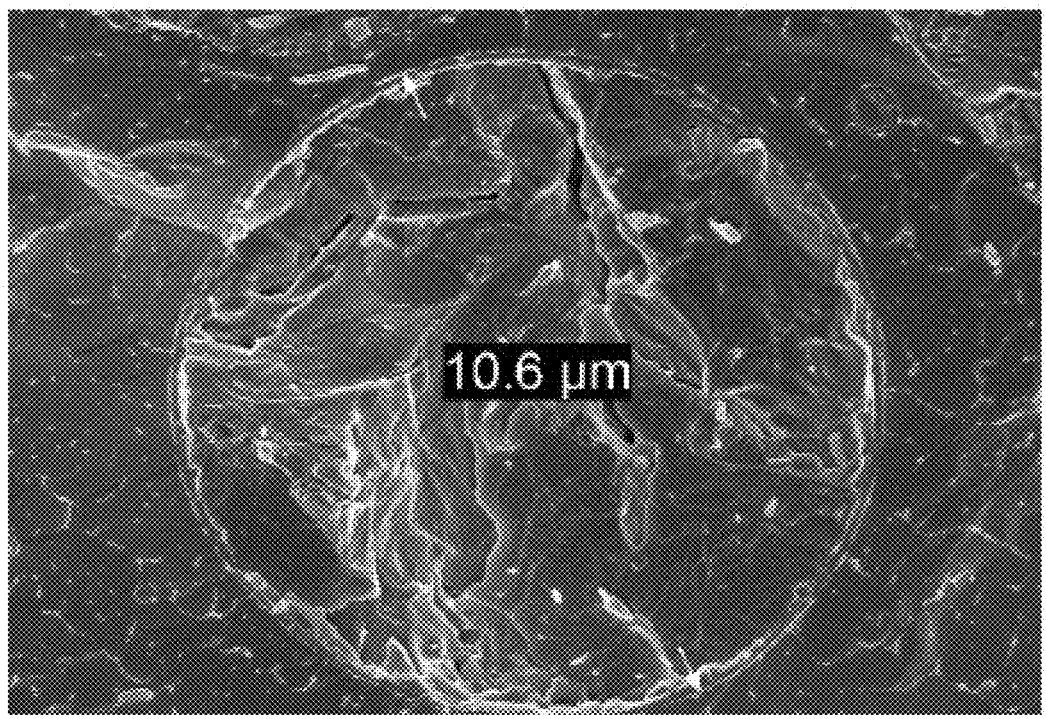
FIG. 24A is a cryo-scanning electron microscopy image of a capsule prepared by conventional batch processing in accordance with the comparative examples, illustrating the diameter of the capsule is 10.6 µm (the white arrows indicate the two end points of the diameter measurement)
Figure 24B:
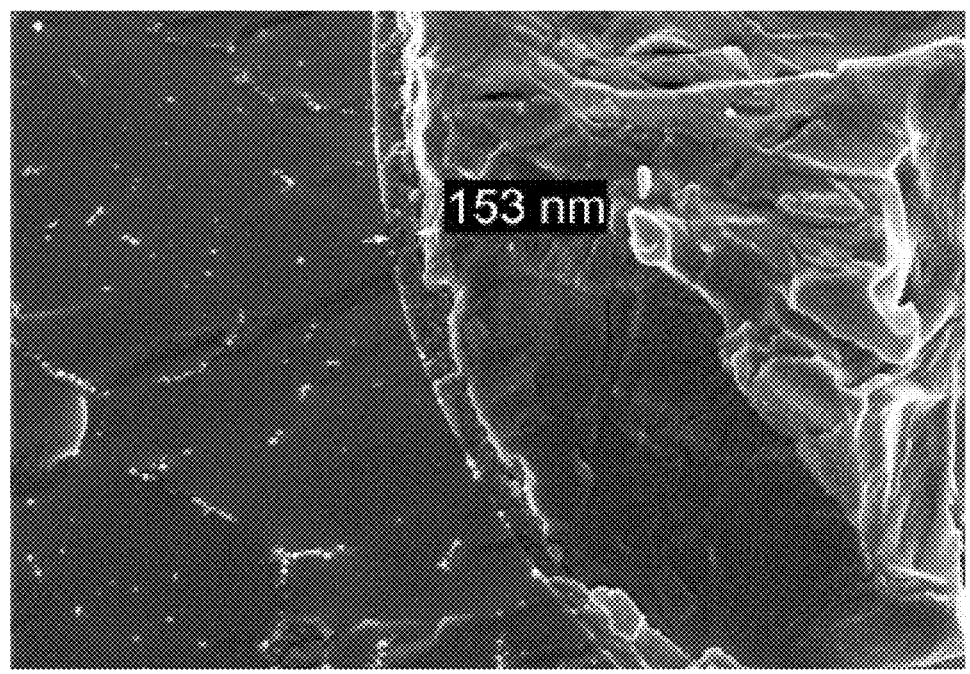
FIG. 24B is a cryo-scanning electron microscopy image of the capsule of FIG. 24A, illustrating the shell thickness of the capsule is 153 nm (the white arrows indicate the two end points of the shell thickness measurement).

Referring to FIGS. 2-3B, in embodiments, the membrane has a plurality of holes or pores. The holes or pores can have any suitable size, density, and arrangement on the membrane surface. In embodiments, the holes or pores can have a mean diameter of about 0.1 μm to about 50 μm, or about 0.1 μm to about 35 μm, or about 0.5 μm to about 30 μm, or about 0.5 μm to about 20 μm, or about 1 μm to about 20 μm, about 4 μm to about 20 μm, For example, the plurality of holes or pores in the membrane can have an mean diameter of about 0.1, 0.5, 1, 2, 3, 4, 5, 6, 7, 8, 9, 10, 15, 20, 25, 30, 35, 40, 45, 50 μm. The plurality of holes or pores can be dispersed randomly across the surface of the membrane or can be arranged in a designated pattern covering the membrane surface. For example, the membrane can include a plurality of pores in a circular, rectangular, square, triangular, pentagonal, hexagonal, or octagonal array.

The example membrane pattern illustrated in FIG. 2 included a pore diameter of 5 μm, with 75 μm spacing between adjacent pores as measured by the distance between the centers of the adjacent pores. The example of FIG. 2 illustrates a hexagonal array. Any suitable membranes can be used including commercially available membranes. Table 1 below provides some example membrane features that can be used in embodiments of the disclosure.

TABLE 1

| Pore Size ($d_p$, μm) | Distance between pores (L, μm) | Open Area (%) | L/$d_p$* |
|---|---|---|---|
| 5 | 75 | 0.4 | 15 |
| 7 | 40 | 2.8 | 5.7 |
| 4.64 | 75 | 0.35 | 16.2 |
| 2.5 | 40 | 0.35 | 16 |
| 17.6 | 75 | 5 | 4.3 |
| 9.4 | 40 | 5 | 4.3 |

*L/$d_p$ is the distance between the pores divided by the diameter of the pores

In FIG. 2, the open area percentage can be calculated as:

$$\text{Open Area Percentage} = \frac{\text{Open Area}}{\text{Total Area}*}$$
$$= \frac{2 \times \text{pore cross section}}{\text{Total Area}*}$$
$$= \frac{2(\pi/4)(d_p)^2}{\text{Total Area}*}$$

*where the total area calculation is dependent on the shape of the membrane.

In embodiments, the open area percentage can be calculated using a rectangular subsection of the membrane, assuming regular spacing and sizing of the pores across the remaining surface of the membrane. In such embodiments the cross section of the pores within the rectangle is used and the total area is represented by the area of the rectangle. For example, the open area % of a membrane with a pore size of 7 μm can be calculated as such:

Open Area=(2×pore cross section)=2(π/4)($d_p$)=77 μm [wherein $d_p$=7 μm]

Total area=75 μm×130 μm=9750 μm [area of the rectangle]

% Open area=open area/total area=0.8%

In embodiments, adjacent pores of the plurality of holes or pores in the membrane can be spaced a mean distance between the center of each pore or hole of about 5 μm to about 500 μm, or about 10 μm to about 250 μm, or about 10 μm to about 200 μm. For examples, the plurality of holes or pores in the membrane can have a distance between the center of each pore of about 5 μm, 10 μm, 20 μm, 30 μm, 40 μm, 50 μm, 60 μm, 70 μm, 75 μm, 80 μm, 90 μm, 100 μm, 110 μm, 120 μm, 130 μm, 140 μm, 150 μm, 160 μm, 170 μm, 180 μm, 190 μm, 200 μm, 210 μm, 220 μm, 230 μm, 240 μm, or 250 μm. In embodiments, adjacent pores of the plurality of holes or pores in the membrane can have an irregular or random spacing or alternatively the spacing can be uniform or patterned.

In embodiments, one or both of the first and second sides of the membrane can have an open area of about 0.01% to about 20% of the surface area of the membrane side, or about 0.1% to about 10%, or about 0.2% to about 10%, or about 0.3% to about 5%. For example, the membrane has an open area of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15% or 20%, or the surface area of the membrane side. In embodiments, the pores can be conically shaped or otherwise tapered such that the opening on the first side is different in size than the opening on the second side, resulting in different open areas on the first and second size. For example, the pores can have a larger opening on the first side and a smaller opening on the second side. In embodiments, the pores can have a smaller opening on the first side and taper to a larger opening on the second side.

In embodiments, the dispersed phase can be passed through the plurality of holes in the membrane at a flux of about 1 m³/m²h to about 500 m³/m²h, or about 1 m³/m²h to about 300 m³/m²h, or about 2 m³/m²h to about 200 m³/m²h, or about 5 m³/m²h to about 150 m³/m²h, 5 m³/m²h to about 100 m³/m²h For example, the dispersed phase can be passed through the plurality of holes in the membrane at a flux rate of 1 m³/m²h, 2 m³/m²h, 3 m³/m²h, 4 m³/m²h, 5 m³/m²h, 6 m³/m²h, 7 m³/m²h, 8 m³/m²h, 9 m³/m²h, 10 m³/m²h, 20 m³/m²h, 30 m³/m²h, 40 m³/m²h, 50 m³/m²h, 60 m³/m²h, 70 m³/m²h, 80 m³/m²h, 90 m³/m²h, 100 m³/m²h, 150 m³/m²h, 200 m³/m²h, 250 m³/m²h, 300 m³/m²h, 350 m³/m²h, 400 m³/m²h, 450 m³/m²h, or 500 m³/m²h. As described herein, the flux is calculated by the following equation:

$$\text{FLUX}\left(\frac{m^3}{m^2h}\right) = \frac{\text{Flow Rate Disperse Phase}\left(\frac{m3}{h}\right)}{\text{Open Area of Membrane (m2)}}$$

$$= \frac{\text{Flow Rate Disperse Phase}\left[\frac{m^3}{h}\right]}{(\#\,\text{pores}) * \frac{\pi}{4} D_{pores}^2 [m^2]}$$

wherein, #pores is the number of pores and $D_{pores}$ is the diameter of the pores in the membrane.

The flow rate of the continuous phase can be adjusted in combination with the flow rate of the dispersed phase to achieve a desired concentration of dispersed phase in the continuous phase.

It has been advantageously found that the concentration of dispersed phase in the continuous phase by weight can be controlled as a function of the ratio of the flow rate of the dispersed phase through the plurality of holes in the membrane and the flow rate of the continuous phase across the second side of the membrane. Advantageously, methods of the disclosure can allow for fine control of the concentration of the dispersed phase in the continuous phase. This can beneficially allow high concentrations of dispersed phase to be incorporated into the continuous phase with the control necessary to prevent overloading of the continuous phase and avoid concentrations at which the droplets of dispersed phase start to coalesce. In embodiments, the ratio of the continuous phase flow rate to dispersed phase flow rate can be 0.1:1, 0.5:1, 1:1, 1.2:1, 1.5:1, 1.8:1, 2:1, 2.5:1, 3:1, 4:1, or 5:1. Selection of the stabilizer system, as described above, can also allow for prevention or limiting of coalescence of the droplets while allowing high concentrations of dispersed phase in the continuous phase. This is advantageous to maintaining narrow capsule size distributions while obtaining high concentrated emulsions.

In accordance with embodiments, the concentration of dispersed phase in the continuous phase can be about 1 wt % to about 70 wt % based on the weight of the dispersed phase divided by the total weight of the emulsion, or about 5% to about 60%, or about 20% to about 60%, or about 30% to about 60%, or about 40% to about 60%. Advantageously, the method herein can have a concentration of dispersed phase in the continuous phase of about 30% or more, for example, about 1%, 5%, 10%, 15%, 20%, 25%, 30%, 35%, 40%, 45%, 50%, 55% or 60%. In embodiments, concentrations of dispersed phase in continuous phase can be up to about 60%, while maintaining limited coalescence, such that the number population diameter CoV in the emulsion is less than or equal to 100%. In embodiments, with the resulting emulsion can have a concentration of dispersed phase in the continuous phase of greater than or equal to 40%, or greater than or equal to 50%, while maintaining a number population diameter CoV in the emulsion of less than or equal to 100%. In embodiments, a high concentration of dispersed phase in the continuous phase can be achieved by having the following: (1) a high flux of dispersed phase through the membrane, (2) a tuned stabilizer system, and (3) high shear stress at the membrane surface.

Having high flux of dispersed phase in the membrane can be advantageous to achieving a high concentration of dispersed phase in the continuous phase, because the higher the velocity of the dispersed phase, the more dispersed phase reaches the surface of the membrane, increasing the frequency of droplet formation, and therefore increasing the overall concentration of dispersed phase in continuous phase. Having a tuned stabilizer system can be advantageous because the stabilizer system can stabilize the droplets of dispersed phase and lower the rate of coalescence of the dispersed phase droplets and increase mass transfer rate. Increasing mass transfer rate can be favorable to avoid coalescence and achieve a narrow size distribution as fresh molecules of the stabilizer system have to reach the surface of the membrane while droplets are forming. Increasing mass transfer rate can help the transportation of dispersed phase droplets away from the membrane surface where new droplets are being formed in order to avoid further coalescence and decrease the local concentration of dispersed phase near the membrane. However, having a high concentration of stabilizer system in the emulsion increases the viscosity of the entirety of the emulsion. Having an increased viscosity of the emulsion can slow the mass transfer of stabilizer molecules as well as the droplets of disperse phase through the continuous phase leading to higher rate of coalescence of the dispersed phase. The stabilizer system therefore needs to be tuned to have enough concentration in the emulsion to achieve the advantages while not negatively effecting the emulsion by increasing viscosity too much. Having high shear stress at the membrane surface can be advantageous because the increased shear stress reduces the size of the droplets of dispersed phase, which favors the movement of said droplets of dispersed phase from the membrane surface.

In embodiments, Table 2 shows the minimum and maximum values as it pertains to the concentration of dispersed phase in the continuous phase. The τ can be calculated with the following equation:

$$\frac{\tau_{max}}{(2*\rho\mu)^{0.5}} = 2a(\pi f)^{1.5}$$

Where:
$\tau_{max}$ is the peak shear event during the oscillation (max shear stress)
ρ—density of continuous phase
μ—viscosity of continuous phase
a—amplitude of oscillation
f—frequency of oscillation

TABLE 2

| | Disperse Phase Flux (m³/(m²h)) | Viscosity of stabilizer solution (cP) | Specific Shear Stress $\left[\frac{\tau_{max}}{(2*\rho\mu)^{0.5}}, \text{m s}^{-1.5}\right]$ |
|---|---|---|---|
| Min Value | 14.3 | 1 | 0.63 |
| Max Value | 120 | 120 | 23 |

The methods further include initializing polymerization of the polymer precursor within the droplets of the dispersed phase. Various initiation methods can be used as are known in the art and selected based on the monomers to be polymerized. By way of example, initializing polymerization of the polymer precursor can include methods involving one or more of a radical, thermal decomposition, photolysis, redox reactions, persulfates, ionizing radiation, electrolysis, or sonication. In embodiments, initializing polymerization of the polymer precursor can include heating the dispersion of droplets of dispersed phase in the continuous phase. In embodiments, initializing polymerization of the polymer precursor can include exposing the dispersion of droplets of dispersed phase in the continuous phase to ultraviolet radiation. In embodiments, initializing polymerization can include activating an initiator present in one or both the dispersed phase and the continuous phase. In embodiments, the initiator can be one or more of thermally activated, photoactivated, redox activated, and electrochemically activated.

In embodiments, the initiator can include a free radical initiator, wherein the free radical initiator can be one or more of peroxy initiators, azo initiators, peroxides, and compounds such as 2,2'-azobismethylbutyronitrile, dibenzoyl peroxide. More particularly, and without limitation, the free radical initiator can be selected from the group of initiators comprising an azo or peroxy initiator, such as peroxide, dialkyl peroxide, alkylperoxide, peroxyester, peroxycarbonate, peroxyketone and peroxydicarbonate, 2,2'-azobis (isobutylnitrile), 2,2'-azobis(2,4-dimethylpentanenitrile), 2,2'-azobis (2,4-dimethylvaleronitrile), 2,2'-azobis(2-methylpropanenitrile), 2,2'-azobis(2-methylbutyronitrile), 1,1'-azobis (cyclohexanecarbonitrile), 1,1'-azobis(cyanocyclohexane), benzoyl peroxide, decanoyl peroxide; lauroyl peroxide; benzoyl peroxide, di(n-propyl)peroxydicarbonate, di(sec-butyl) peroxydicarbonate, di(2-ethylhexyl)peroxydicarbonate, 1,1-dimethyl-3-hydroxybutyl peroxyneodecanoate, a-cumyl peroxyneoheptanoate, t-amyl peroxyneodecanoate, t-butyl peroxyneodecanoate, t-amyl peroxypivalate, t-butyl peroxypivalate, 2,5-dimethyl 2,5-di (2-ethylhexanoyl peroxy)hexane, t-amyl peroxy-2-ethylhexanoate, t-butyl peroxy-2-ethylhexanoate, t-butyl peroxyacetate, di-t-amyl peroxyacetate, t-butyl peroxide, dit-amyl peroxide, 2,5-dimethyl-2,5-di-(t-butylperoxy)hexyne-3, cumene hydroperoxide, 1,1-di-(t-butylperoxy)-3,3,5-trimethyl-cyclohexane, 1,1-di-(t-butylperoxy)-cyclohexane, 1,1-di-(t-amylperoxy)-cyclohexane, ethyl-3,3-di-(t-butylperoxy)-butyrate, t-amyl perbenzoate, t-butyl perbenzoate, ethyl 3,3-di-(t-amylperoxy)-butyrate, and the like.

In embodiments, the initiator can include a thermal initiator. In embodiments, the thermal initiator can have a bond dissociation energy of about 100 kJ per mol to about 170 kJ per mol. The thermal initiator can include one or more of peroxides, such as acyl peroxides, acetyl peroxides, and benzoyl peroxides, azo compounds, such as 2,2'-azobisisobutyronitrile, 2,2'-azobis(2,4-dimethylpentanenitrile), 4,4'-azobis(4-cyanovaleric acid), and 1,1'-azobis(cylohexanecarbonitrile), and disulfides.

In embodiments, the initiator can include a redox initiator such as a combination of an inorganic reductant and an inorganic oxidant. For example, reductants such as peroxydisulfate, $HSO_3^-$, $SO_3^{2-}$, $S_2O_3^{2-}$, $S_2O_5^{2-}$, or an alcohol with a source of oxidant such as $Fe^{2+}$, $Ag^+$, $Cu^{2+}$, $Fe^{3+}$, $ClO_3^-$, $H_2O_2$, $Ce^{4+}$, $V^{5+}$, $Cr^{6+}$, or $Mn^{3+}$.

In embodiments, the initiator can include one or more photochemical initiators, such as benzophenone; acetophenone; benzil; benzaldehyde; o-chlorobenzaldehyde; xanthone; thioxanthone; 9,10-anthraquinone; 1-hydroxycyclohexyl phenyl ketone; 2,2-diethoxyacetophenone; dimethoxyphenylacetophenone; methyl diethanolamine; dimethylaminobenzoate; 2-hydroxy-2-methyl-1-phenylpropane-1-one; 2,2-di-sec-butoxyacetophenone; 2,2-dimethoxy-1,2-diphenylethan-1-one; dimethoxyketal; and phenyl glyoxal.2,2'-diethoxyacetophenone, hydroxycyclohexyl phenyl ketone, alpha-hydroxyketones, alpha-aminoketones, alpha and beta naphthyl carbonyl compounds, benzoin ethers such as benzoin methyl ether, benzil, benzil ketals such as benzil dimethyl ketal, acetophenone, fluorenone, 2-hydroxy-2-methyl-1-phenylpropan-1-one. UV initiators of this kind are available commercially, e.g., Irgacure 184, Irgacure 369, Irgacure LEX 201, Irgacure 819, Irgacure 2959 Darocur 4265 or Degacure 1173 from Ciba or visible light initiator: Irgacure 784 and Camphorquinone (Genocure CQ). In embodiments, the initiator can be a thermal initiator as described in patent publication: WO 2011084141 A1.

In embodiments, the initiator can include one or more of 2,2'-Azobis(2,4-dimethylvaleronitrile), 2,2'-Azobis(2-methylbutyronitrile), 4,4'-Azobis(4-cyanovaleric acid), 2,2'-azobis [N-(2-hydroxyethyl)-2-methylpropionamide], 1,1'-Azobis(cyclohexane-1-carbonitrile. Commercially available initiators, such as Vazo initiators, typically indicate a decomposition temperature for the initiator. In embodiments, the initiator can be selected to have a decomposition point of about 50° C. or higher. In embodiments, initiators are selected to stagger the decomposition temperatures at the various steps, pre-polymerization, shell formation and hardening or polymerizing of the capsule shell material. For example, a first initiator in the dispersed phase can decompose at 55° C., to promote prepolymer formation; a second can decompose at 60° C. to aid forming the shell material. Optionally, a third initiator can decompose at 65° C. to facilitate polymerization of the capsule shell material.

In embodiments, the total amount of initiator can be present in the dispersed phase in an amount of about 0.001 wt % to about 5 wt % based on the total weight of the dispersed phase, or about 0.01 wt % to about 4 wt %, or about 0.1 wt % to about 2 wt %. For example, the total amount of initiator can be present in the dispersed phase in an amount of about 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 2 wt %, 3 wt %, 4 wt %, or 5 wt %.

In embodiments, the continuous phase can be substantially free of initiator. In embodiments, the total amount of initiator can be present in the continuous phase in an amount of about 0% to about 3%, or about 0.01% to about 3%, or about 0.01% to about 2%. For example, the total amount of initiator can be present in the continuous phase in an amount of about 0.1 wt %, 0.2 wt %, 0.3 wt %, 0.4 wt %, 0.5 wt %, 0.6 wt %, 0.7 wt %, 0.8 wt %, 0.9 wt %, 1 wt %, 1.1 wt %, 1.2 wt %, 1.3 wt %, 1.4 wt %, 1.5 wt %, 2 wt %, 3 wt %.

In embodiments, the dispersed phase can further include an inhibitor. In embodiments, the inhibitor can be one or more of oxygen, quinones, sodium nitrite. In embodiments, the inhibitor can be included to delay or prevent polymerization of the polymer precursor to form the capsules shell. The inhibitor may inhibit polymerization until certain conditions are met, such as, until the inhibitor is consumed by the system over time, or the polymerization can be intentionally triggered despite having the inhibitor in the dispersed phase by an addition of one or more secondary compounds, or a change of conditions that overcomes the effect of the inhibitor. The inhibitor can be advantageous for multiple reasons including controlling the capsule formation process and/or avoiding unintentional early polymerization before the dispersed phase is entirely dispersed in the continuous phase.

In embodiments, the continuous phase may content phase transfer catalyst to improve the effectiveness of the initiators in this phase. Phase transfer catalyst materials can include, for example, one or more of quaternary ammonium and phosphonium salts, crown ethers and cryptands.

In embodiments, and without intending to be bound by theory it is believed that as the polymer precursor begins polymerizing, the resulting polymer becomes insoluble in the dispersed phase, and further migrates to the interface between the dispersed phase and the continuous phase.

In any of the embodiments disclosed herein, the capsules can include a benefit agent in the core. In embodiments, the benefit agent can include one or more perfume compositions, perfume raw materials, silicone oils, waxes, hydrocarbons, higher fatty acids, essential oils, lipids, skin coolants, vitamins, sunscreens, antioxidants, glycerine, catalysts, bleach encapsulates, silicon dioxide encapsulates, malodor reducing agents, odor-controlling materials, chelating agents, antistatic agents, softening agents, agricultural materials such as pesticides, insecticides, nutrients, herbicides, fungus control, insect and moth repelling agents, colorants, antioxidants, chelants, bodying agents, drape and form control agents, smoothness agents, wrinkle control agents, sanitization agents, disinfecting agents, germ control agents, mold control agents, mildew control agents, antiviral agents, drying agents, stain resistance agents, soil release agents, fabric refreshing agents and freshness extending agents, chlorine bleach odor control agents, dye fixatives, dye transfer inhibitors, color maintenance agents, optical brighteners, color restoration/rejuvenation agents, anti-fading agents, whiteness enhancers, anti-abrasion agents, wear resistance agents, fabric integrity agents, anti-wear agents, anti-pilling agents, defoamers, anti-foaming agents, UV protection agents, sun fade inhibitors, anti-allergenic agents, enzymes, water proofing agents, fabric comfort agents, shrinkage resistance agents, stretch resistance agents, stretch recovery agents, other construction agents, such as phase change materials, self-healing materials, skin care agents, glycerin, and natural actives, antibacterial actives, antiperspirant actives, cationic polymers, and dyes, food and feed agents such as antioxidants, probiotics and food and beverage colorants. In embodiments, the benefit agent can include one or more of perfume compositions, perfume raw materials, sanitization agents, disinfecting agents, antiviral agents, fabric refreshing agents and freshness extending agents, chlorine bleach odor control agents, dye fixatives, dyes, optical brighteners, color restoration/rejuvenation, enzymes, anti-foaming agents, fabric comfort agents, skin care agents, lubricants, waxes, hydrocarbons, malodor reducing agents, odor-controlling materials, fertilizers, nutrients, and herbicides.

In embodiments, the benefit agent can include a perfume or a perfume composition. In embodiments, the perfume composition can include one or more of perfume raw materials, essential oils, malodour reducing agents, and odour controlling agents.

Malodour reducing agents maybe selected from antibacterial materials, enzyme inhibitors, reactive aldehydes, masking perfume raw materials and masking accords, and binding polymers, e.g., polyethylene imines. In embodiments, the dispersed phase can further include additional components such as excipients, carriers, diluents, and other agents. In embodiments, the benefit agent can be admixed with an oil. In embodiments, the oil admixed with the benefit agent can include isopropyl myristate.

In embodiments, the dispersed phase can further include a process-aid. In embodiments, the process-aid can include one or more of a carrier, an aggregate inhibiting material, a deposition aid, and a particle suspending polymer. Non-limiting examples of aggregate inhibiting materials include salts that can have a charge-shielding effect around the capsule, such as magnesium chloride, calcium chloride, magnesium bromide, magnesium sulfate, and mixtures thereof. Non-limiting examples of particle suspending polymers include polymers such as xanthan gum, carrageenan gum, guar gum, shellac, alginates, chitosan; cellulosic materials such as carboxymethyl cellulose, hydroxypropyl methyl cellulose, cationically charged cellulosic materials; polyacrylic acid; polyvinyl alcohol; hydrogenated castor oil; ethylene glycol distearate; and mixtures thereof.

In accordance with embodiments, capsules can be produced according to the methods described herein.

Test Methods

When encapsulated actives are incorporated into products, the sample preparation for analysis should yield an aqueous suspension of non-aggregated particles for analysis that has not altered the original size distribution. For example, a representative preparation could include that described in WO2018169531A1, pp. 31-34, the disclosure of which is incorporated herein.

Capsule Size and Distribution Test Method

Capsule size distribution is determined via single-particle optical sensing (SPOS), also called optical particle counting (OPC), using the AccuSizer 780 AD instrument and the accompanying software CW788 version 1.82 (Particle Sizing Systems, Santa Barbara, Calif., U.S.A.), or equivalent. The instrument is configured with the following conditions and selections: Flow Rate=1 ml/sec; Lower Size Threshold=0.50 μm; Sensor Model Number=LE400-05 or equivalent; Autodilution=On; Collection time=60 sec; Number channels=512; Vessel fluid volume=50 ml; Max coincidence=9200. The measurement is initiated by putting the sensor into a cold state by flushing with water until background counts are less than 100. A sample of delivery capsules in suspension is introduced, and its density of capsules adjusted with DI water as necessary via autodilution to result in capsule counts of at least 9200 per ml. During a time period of 60 seconds the suspension is analyzed. The range of size used was from 1 μm to 493.3 μm. Accordingly, the volume distributions and number distributions are calculated as shown and described above.

From the cumulative volume distribution, also the diameter of the percentiles 5 ($d_5$), 50 ($d_{50}$) and 90 ($d_{90}$) are calculated (Percentile j is determined by the cumulative volume distribution where the j percentage of the volume is accumulated ($\Sigma_{d=1\ um}^{d_j} x_{i,v} = j$ (%))).

Delta Fracture Strength Test Method

To measure delta Fracture Strength, three different measurements are made: i) the volume-weighted capsule size distribution; ii) the diameter of 10 individual capsules within each of 3 specified size ranges, and; iii) the rupture-force of those same 30 individual capsules.

a.) The volume-weighted capsule size distribution is determined via single-particle optical sensing (SPOS), also called optical particle counting (OPC), using the AccuSizer 780 AD instrument and the accompanying software CW788 version 1.82 (Particle Sizing Systems, Santa Barbara, Calif., U.S.A.), or equivalent. The instrument is configured with the following conditions and selections: Flow Rate=1 ml/sec; Lower Size Threshold=0.50 μm; Sensor Model Number=Sensor Model Number=LE400-05 or equivalent; Autodilution=On; Collection time=60 sec; Number channels=512; Vessel fluid volume=50 ml; Max coincidence=9200. The measurement is initiated by putting the sensor into a cold state by flushing with water until background counts are less than 100. A sample of delivery capsules in suspension is introduced, and its density of capsules adjusted with DI water as necessary via autodilution to result in capsule counts of at least 9200 per ml. During a time period of 60 seconds the suspension is analyzed. The resulting volume-weighted PSD data are plotted and recorded, and the values of the median, $5^{th}$ percentile, and $90^{th}$ percentile are determined.

b.) The diameter and the rupture-force value (also known as the bursting-force value) of individual capsules are measured via a custom computer-controlled micromanipulation instrument system which possesses lenses and cameras able to image the delivery capsules, and which possess a fine, flat-ended probe connected to a force-transducer (such as the Model 403A available from Aurora Scientific Inc, Canada) or equivalent, as described in: Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602, and as available at the University of Birmingham, Edgbaston, Birmingham, UK.

c.) A drop of the delivery capsule suspension is placed onto a glass microscope slide, and dried under ambient conditions for several minutes to remove the water and achieve a sparse, single layer of solitary capsules on the dry slide. Adjust the concentration of capsules in the suspension as needed to achieve a suitable capsule density on the slide. More than one slide preparation may be needed.

d.) The slide is then placed on a sample-holding stage of the micromanipulation instrument. Thirty benefit delivery capsules on the slide(s) are selected for measurement, such that there are ten capsules selected within each of three pre-determined size bands. Each size band refers to the diameter of the capsules as derived from the Accusizer-generated volume-weighted PSD. The three size bands of capsules are: the Median Diameter+/−2 μm; the $5^{th}$ Percentile Diameter+/−2 μm; and the $90^{th}$ Percentile Diameter+/−2 μm. Capsules which appear deflated, leaking or damaged are excluded from the selection process and are not measured.

e.) For each of the 30 selected capsules, the diameter of the capsule is measured from the image on the micromanipulator and recorded. That same capsule is then compressed between two flat surfaces, namely the flat-ended force probe and the glass microscope slide, at a speed of 2 μm per second, until the capsule is ruptured. During the compression step, the probe force is continuously measured and recorded by the data acquisition system of the micromanipulation instrument.

f.) The cross-sectional area is calculated for each of the selected capsules, using the diameter measured and assuming a spherical capsule ($\pi r^2$, where r is the radius of the capsule before compression). The rupture force is determined for each selected capsule from the recorded force probe measurements, as demonstrated in Zhang, Z. et al. (1999) "Mechanical strength of single microcapsules determined by a novel micromanipulation technique." *J. Microencapsulation*, vol 16, no. 1, pages 117-124, and in: Sun, G. and Zhang, Z. (2001) "Mechanical Properties of Melamine-Formaldehyde microcapsules." *J. Microencapsulation*, vol 18, no. 5, pages 593-602.

g.) The Fracture Strength of each of the 30 capsules is calculated by dividing the rupture force (in Newtons) by the calculated cross-sectional area of the respective capsule.

With the recorded data, the Delta Fracture Strength is calculated $$\text{Delta Fracture Strength}(\%) = \frac{FS@d_5 - FS@d_{90}}{FS@d_{50}} * 100$$

where FS at $d_i$ is the FS of the capsules at the percentile i of the volume size distribution.

Shell Thickness Measurement Test Method

The capsule shell thickness is measured in nanometers on 20 benefit agent containing delivery capsules using freeze-fracture cryo-scanning electron microscopy (FF cryoSEM), at magnifications of between 50,000× and 150,000×. Samples are prepared by flash freezing small volumes of a suspension of capsules or finished product. Flash freezing can be achieved by plunging into liquid ethane, or through the use of a device such as a High Pressure Freezer Model 706802 EM Pact, (Leica Microsystems, and Wetzlar, Germany) or equivalent. Frozen samples are fractured while at −120° C., then cooled to below −160° C. and lightly sputter-coated with gold/palladium. These steps can be achieved using cryo preparation devices such as those from Gatan Inc., (Pleasanton, Calif., USA) or equivalent. The frozen, fractured and coated sample is then transferred at −170° C. or lower, to a suitable cryoSEM microscope, such as the Hitachi S-5200 SEM/STEM (Hitachi High Technologies, Tokyo, Japan) or equivalent. In the Hitachi S-5200, imaging is performed with 3.0 KV accelerating voltage and 5 μA-20 μA tip emission current.

Images are acquired of the fractured shell in cross-sectional view from 20 benefit delivery capsules selected in a random manner which is unbiased by their size, so as to create a representative sample of the distribution of capsule sizes present. The shell thickness of each of the 20 capsules is measured using the calibrated microscope software, by drawing a measurement line perpendicular to the tangent of the outer surface of the capsule wall. The 20 independent shell thickness measurements are recorded and used to calculate the mean thickness, and the percentage of the capsules having a selected shell thickness.

The diameter of the 20 cross sectioned capsules is also measured using the calibrated microscope software, by drawing a measurement line perpendicular to the cross section of the capsule.

Effective Volumetric Core-Shell Ratio Evaluation

The effective volumetric core-shell ratio values were determined as follows, which relies upon the mean shell thickness as measured by the Shell Thickness Test Method.

The effective volumetric core-shell ratio of a capsule where its mean shell thickness was measured is calculated by the following equation:

$$\frac{\text{Core}}{\text{Shell}} = \frac{\left(1 - \frac{2*\text{Thickness}}{D_{caps}}\right)^3}{\left(1 - \left(1 - \frac{2*\text{Thickness}}{D_{caps}}\right)^3\right)}$$

wherein thickness is the thickness of the shell of an individual capsule and the Dcaps is the diameter of the cross-sectioned capsule.

The 20 independent effective volumetric core-shell ratio calculations were recorded and used to calculate the mean effective volumetric core-shell ratio.

This ratio can be translated to fractional core-shell ratio values by calculating the core weight percentage using the following equation:

$$\% \text{Core} = \left(\frac{\frac{\text{Core}}{\text{Shell}}}{1 + \frac{\text{Core}}{\text{Shell}}}\right) * 100$$

and shell percentage can be calculated based on the following equation:

$$\% \text{Shell} = 100 - \% \text{Core}.$$

Logarithm of Octanol/Water Partition Coefficient (log P) Test Method

The value of the log of the Octanol/Water Partition Coefficient (log P) is computed for each perfume raw material (PRM) in the perfume mixture being tested. The log P of an individual PRM (log $P_i$) is calculated using the Consensus log P Computational Model, version 14.02 (Linux) available from Advanced Chemistry Development Inc. (ACD/Labs) (Toronto, Canada), or equivalent, to provide the unitless log P value. The ACD/Labs' Consensus log P Computational Model is part of the ACD/Labs model suite.

The individual log P for each PRM is recorded to calculate the mean log P of the perfume composition by using the following equation:

$$\log P = \sum_{i=1}^{n} \frac{x_i}{100} \log P_i$$

where $x_i$ is the % wt of PRM in perfume composition.

EXAMPLES

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure. In each of examples 1-7 below, the membrane utilized is illustrated in FIG. 1.

Comparison of Capsules Made in Accordance with the Disclosure to Conventional Batch Processing

Example 1

Chemistry 1 by Using Membrane Emulsification

Referring to FIG. 4A-10B, capsules in accordance with the disclosure were made. The following method was utilized. A first oil solution, which was the initiator solution, was formed by mixing Fragrance Oil (44.85 wt %), Isopropyl myristate (54.2 wt %), 2,2'-Azobis(2,4-dimethylvaleronitrile) (Vazo 52, 0.58 wt %), and 2,2'-Azobis(2-methylbutyronitrile) (Vazo-67 0.38 wt %), at 20° C. A second oil solution, which was the monomer solution, was formed by mixing Fragrance Oil (81.34 wt %), and Sartomer CN975 (hexafunctional aromatic urethane-acrylate oligomer, 18.66 wt %) at 20° C. The first oil solution and the second oil solution were then pumped using two gear pumps (IS-MATEC, micropump 0.32 ml/rev) at a proportion of 1:1 by weight to form the disperse phase before entering into the membrane shaft.

A continuous phase (aqueous solution) was prepared containing Selvol 540 (1.78 wt %), NaOH (0.07 wt %) and 4,4'-Azobis(4-cyanovaleric acid) (Vazo 68WSP, 0.37 wt %) in water. The continuous phase was pumped across the second surface of the membrane by using a Tuthill GDS pump.

The emulsification was prepared using an oscillatory membrane emulsification rig. The membrane device included a laser-drilled membrane, which had a stainless steel film laser welded and mounted vertically on a membrane shaft (supplied by Micropore). The membrane had pores having a diameter of 7 µm, with the pores being arranged in a hexagonal array and adjacent pores spaced a distances of 40 µm as measured from pore center to pore center. The membrane shaft was inserted into the membrane housing and coupled to an oscillatory motor. The continuous phase was pumped in the gap between the membrane shaft and the housing. The dispersed phase was injected from the top of the membrane shaft towards the back part of the membrane. The disperse phase permeated through the pores of the membrane to the continuous phase, forming an emulsion that exited the emulsification chamber to be collected in a collection vessel.

The flux of disperse phase though the membrane was 24.9 $m^3/(m^2$ of membrane open area*h) and the mass flow rate of the continuous phase was adjusted to achieve a ratio of continuous phase to dispersed phase of 1.5. Both flow rates were measured by using Coriolis mass flowmeters (Bronkhorst, m14), placed between the pumps and the membrane device. The membrane shaft was oscillated at a frequency of 30 Hz and 12.9 mm of amplitude of oscillation.

Once a liter of the emulsion was collected in a jacketed vessel, polymerization was initiated to form the capsules. Polymerization was initiated by mixing the emulsion gently at 200 rpm and the temperature was raised to 60° C. over a 15 minute ramp period. The temperature was then held at 60° C. for 45 minutes. The temperature was then increased to 75° C. over a 30 minute ramp period, and subsequently held at 75° C. for 4 hours. Finally the temperature was raised to 90° C. over a 30 minute ramp period, and held at 90° C. for 8 hours. The batch was then allowed to cool to room temperature.

Comparative Example 1 for Chemistry 1

Batch Process

Referring to FIGS. 11A-17B, capsules made by a conventional batch process are illustrated. The capsules were made by the following method. An oil solution (dispersed phase) was made by mixing a Fragrance Oil (63.09% wt), Isopropyl myristate (27.1% wt), Vazo 52 (0.29% wt), and Vazo-67 (0.19% wt), Sartomer CN975 (hexafunctional aromatic urethane-acrylate oligomer, 9.33% wt), at 20° C.

An aqueous solution (continuous phase) was made by mixing Selvol 540 polyvinyl alcohol (1.78 wt %), NaOH (0.07 wt %), and Vazo-68WSP (0.37 wt %).

The dispersed phase and the continuous phase were mixed at a ratio of continuous phase to disperse phase of 1.5 and at 1100 rpm for 30 min with a 5 cm diameter 4 pitched blade stirrer, to achieve an emulsion.

Once the emulsion was accomplished, it was transferred to a jacketed vessel and gently mixed at 200 rpm. and its temperature was raised to 60° C. in 15 min. Then, the temperature was held at 60° C. for 45 minutes, the temperature was increased to 75° C. in 30 minutes, held at 75° C. for 4 hours, heated to 90° C. in 30 minutes and held at 90° C. for 8 hours. The batch is then allowed to cool to room temperature.

Comparative Example 2 for Chemistry 1

Batch Process

Referring to FIGS. 18A-24B, capsules were made in accordance with a conventional batch process. A first oil solution was prepared by mixing Fragrance Oil (61.86 wt %), Isopropyl myristate (37.48 wt %), Vazo-52 (0.40 wt %), and Vazo-67 (0.26 wt %), at 35° C. in a temperature controlled steel jacketed reactor, with mixing at 1000 rpm (4 tip. 2" diameter, pitched mill blade) and a nitrogen blanket applied at 100 cc/min. The oil solution was heated to 75° C. over a 45 minute ramp, held at 75° C. for 45 minutes, and cooled to 60° C. over a 75 minute ramp.

A second oil solution was prepared by mixing Fragrance Oil (64.77 wt %), tertiarybutylaminoethyl methacrylate (0.86 wt %), 2-carboxyethyl acrylate (0.69 wt %), and Sartomer CN975 (33.68 wt %) (hexafunctional aromatic urethane-acrylate oligomer) and then adding the second oil solution to the first oil solution when the first oil solution reached 60° C. The ratio of first oil solution to second oil solution was 2.6 to 1. The combined oil solutions represented the dispersed phase and were held at 60° C. for an additional 10 minutes.

Separately, a continuous phase was prepared as an aqueous solution containing Selvol 540 (1.78 wt %), NaOH (0.07 wt %) and Vazo 68WSP (0.37 wt %) in water.

The continuous phase and disperse phase were mixed at 1100 rpm, for 30 minutes at 60° C. (5 cm diameter stirrer) to emulsify the disperse phase into the continuous phase. The ratio continuous phase to disperse phase was 1.5. After emulsification is accomplished, mixing was continued with an anchor mixer at 200 rpm. The batch was held at 60° C. for 45 minutes, the temperature was then increased to 75° C. over a 30 minute ramp, held at 75° C. for 4 hours, and then finally heated to 90° C. over a 30 minute ramp and held at 90° C. for 8 hours to polymerize the capsules shell. The batch was then allowed to cool to room temperature.

Example 2

Chemistry 2 by Using Membrane Emulsification

The phases in the membrane emulsification is as follow:

Dispersed phase consisted of Fragrance.

Continuous phase is made of the following chemicals and they are listed in order of dissolution in water

| Substance | % Wt |
|---|---|
| poly(ethylene-alt-maleic anhydride) [p-EMA (CAS #9 006-26-2)] | 0.60 |
| Urea | 1.94 |
| Resorcinol | 0.19 |
| Water | 97.27 |

Once the chemicals are dissolved in water, the solution pH is adjusted at 3.5 by adding 16% wt NaOH solution in water.

The emulsification was prepared using an oscillatory membrane emulsification device (LTS-1 torsional cell). The membrane device included a laser-drilled membrane, which had a stainless steel film laser welded and mounted vertically on a membrane shaft (supplied by Micropore). The membrane had pores having a diameter of 7 µm, with the pores being arranged in a hexagonal array and adjacent pores spaced a distances of 40 µm as measured from pore center to pore center. The membrane shaft was inserted into the membrane housing and coupled to an oscillatory motor. The continuous phase was pumped in the gap between the membrane shaft and the housing. The dispersed phase was injected from the top of the membrane shaft towards the back part of the membrane. The disperse phase permeated through the pores of the membrane to the continuous phase, forming an emulsion that exited the emulsification chamber to be collected in a collection vessel.

The flux of disperse phase though the membrane was 30 m3/(m2 of membrane open area*h) and the mass flow rate of the continuous phase was adjusted to achieve a ratio of continuous phase to dispersed phase of 2. Both flow rates were measured by using Coriolis mass flowmeters (Bronkhorst, m14), placed between the pumps and the membrane device. The membrane shaft was oscillated at a frequency of 30 Hz and 12.9 mm of amplitude of oscillation.

Once the emulsion is achieved, 36% formaldehyde solution was dropwise added over 5 minutes. Then the emulsion was heated at 50 C in 30 min, kept at 50 C for 4 h, and cooled to room temperature.

The final composition of the capsule slurry was as follow:

| Substance | % Wt |
|---|---|
| Formaldehyde solution 36% | 6.18 |
| p-EMA (CAS # 9006-26-2) | 0.4 |
| Resorcinol | 1.17 |
| Urea | 0.12 |
| Voyager Zen | 33.3 |
| Water | 58.83 |

Comparative Example 1 for Chemistry 2

Batch Process

The final composition of the capsule slurry is collected at the end of the description. The protocol is as follow.

A 3% wt solution of poly(ethylene-alt-maleic anhydride) in water [p-EMA solution] was done. Urea was dissolved into the p-EMA solution. Then, Resorcinol was dissolved in the urea/pEMA solution. pH of the solution was adjusted at 3.5 by adding 16% wt NaOH solution. After pH adjusting, the fragrance was added and emulsification was carried out at 1150 rpm using an overhead stirrer. for 30 min.

Once the emulsion is achieved, 36% formaldehyde solution was dropwise added over 5 minutes. Then the emulsion was heated at 50 C in 30 min, kept at 50 C for 4 h, and cooled to room temperature.

The final composition of the capsule slurry was as follows:

| Substance | % Wt |
| --- | --- |
| Formaldehyde solution 36% | 6.17 |
| 3% solution of p-EMA (CAS # 9006-26-2) in water | 12.1 |
| Resorcinol | 0.11 |
| Urea | 1.17 |
| Voyager Zen | 33.33 |
| Water | 47.11 |

Summary of Example Results

As illustrated by comparison of FIGS. 4A-10B to FIGS. 11A-24B, capsules of Example 1 had a narrower distribution of capsules. Table 3 provides various parameters of the resulting capsules, including the mean diameter, coefficient of variation of the diameter expressed as a volume percent and as a number percent, the delta fracture strength percentage, mean wall thickness (nm), mean effective ratio of volume percent core to volume percent shell. As illustrated in Table 3, the capsules in accordance with the disclosure had a lower number population diameter CoV as compared to the batch process, as well as lower delta fracture strength percentage. Based on these results, it is believed that the capsules in accordance with the disclosure would have improved performance for reliably and more uniformly releasing a benefit agent when part of a formulated product.

TABLE 3

| Sample | Mean Diameter (um) | CoV of Diameter Vol (%) | Delta Fracture Strength (%) | Mean Wall thickness (nm) | Mean Effective Core-Shell Ratio | CoV of Diameter in Nb (%) |
| --- | --- | --- | --- | --- | --- | --- |
| Example 1 | 24.9 | 23 | 149.1 | 171 | 95.4/4.6 | 34.1 |
| Comparative Example 1 | 26.2 | 41 | 1773.1 | 128 | 96.4/3.6 | 130.0 |
| Comparative Example 2 | 27.3 | 39 | 1028.6 | 123 | 96.9/3.1 | 134.0 |
| Example 2 (chemistry 2) | 29.6 | 21 | 125.0 | 106 | 97.6/2.4 | 94.9 |
| Comparative Example 1 for chemistry 2 | 29.1 | 36 | 495.5 | 104 | 98.1/1.9 | 144.1 |

Method for Determining Performance

Product Preparation and Washtest

Prepare fabric enhancer products containing 0.158% (as 100% active) encapsulated perfume oil.

Liquid fabric enhancer products are prepared in the following manner. Water, chelant, HCl, formic acid, and preservative are mixed together in a glass beaker with a magnetic stirrer. This aqueous solution is heated up in an oven at 85° C. The fabric softener active (a diester quaternary ammonium compound) is heated up in an oven at 85° C. The aqueous solution directly coming from oven is mixed with an overhead mixer. The fabric softener active directly coming from the oven is added into the hot water. The obtained dispersion is cooled down by letting it rest in a room at 21° C. Encapsulated perfume oil is added.

Next, the structurant is added during overhead stirring, and it is further dispersed with the overhead stirrer.

Products are used to run a full scale wash in Miele PowerWash 2.0 W1_washing machine.

For the test 3 kg ballast load is used. The load consists of 1.5 kg of cotton and 1.5 kg of polycotton. Ballast loads are preconditioned in Miele Softronic W1714 washing machine by running a short cotton cycle wash at 95° C. In total 4 runs are done: 2 runs where 70 g unperfumed powder is added in dispenser followed by 2 runs without detergent.

After preconditioning the ballast loads are tumble dried.

For each washtest 6 small terry tracers (100% cotton, 30×30 cm) are added into the washing machine. These tracers are preconditioned in same way as ballast load (50 terry tracers per washing machine).

Before running the test washing machines are boiled out using a cotton cycle run at 95° C.

Liquid Fabric Enhancer Washtest

Two legs are run:

A=Liquid fabric enhance+0.158% encapsulated perfume oil from Example 1 for chemistry 1

B=Liquid fabric enhancer+0.158% encapsulated perfume oil from Comparative Example 1 from chemistry 1

Washtest is run in Miele PowerWash 2.0 W1_washing machine, wash cycle is short cotton cycle wash at 40° C. and a spin speed of 1200 rpm.

Put ballast load and terry tracers in washing machine. In dispenser add 79 g unperfumed powder. Run wash cycle. When last rinse starts add in dispenser liquid fabric enhancer product (35 ml liquid fabric enhancer product prediluted in 2 liter city water)

After wash remove terry tracers from washing machine.

Terry tracers are submitted for GC-HS evaluation: 1 day line dried terry tracers are submitted for headspace analysis.

Headspace Analysis

Dry fabric samples, originating from rinse/wash cycles, were analyzed by fast headspace GC/MS approach. 4×4 cm part of the terry cotton tracers were transferred to 25 ml headspace vials. The fabric samples were equilibrated for 10 minutes@ 65° C. The headspace above the fabrics was sampled via SPME (50/30 μm DVB/Carboxen/PDMS) approach for 5 minutes. The SPME fiber was subsequently on-line thermally desorbed into the GC. The analytes were analyzed by GC/MS in full scan mode.

Results of Comparative Performance Test

| Code | Product details | Mean (nM/L) | Standard Deviation (nM/L) |
|---|---|---|---|
| A | Liquid fabric enhancer + 0.158% encapsulated perfume oil from Example 1 for chemistry 1 | 162.9 | 45.0 |
| B | Liquid fabric enhancer + 0.158% encapsulated perfume oil from Comparative Example 1 from chemistry 1 | 93.7 | 35.5 |

To determine whether there is a statistically significative difference in the performance of the capsules from the two examples, the two samples t-test is used. Assuming that the variances for the performances of the two type of capsules were identical, then the appropriate test statistic to use for comparing two treatment means in the completely randomized design is:

$$t_0 = \frac{y_A - y_B}{S_P\sqrt{\frac{1}{n_A} + \frac{1}{n_B}}}$$

where $y_A$ and $y_B$ are the sample means, $n_A$ and $n_B$ are the sample sizes, $S_P$ is an estimate of the common variance of the results of the performance test for both capsules and computed from:

$$S_P^2 = \frac{(n_A - 1)S_A^2 + (n_B - 1)S_B^2}{n_A + n_B - 2}$$

and $S_A^2$ and $S_B^2$ are the variances of the samples that can be computed as follow:

$$S_i^2 = \frac{\sum_{i=1}^{ni}(y_{ji} - y_i)}{n_i - 1}$$

Where $S_i^2$ is the variance of sample i, $n_i$ is the size of sample i, $y_{ji}$ is the jth result of the sample i and $y_i$ is the means of sample i.
To determine whether to reject the null hypothesis where the means of the results of the performance is true, $t_0$ is compared to the t distribution with $n_A+n_B-2$ degrees of freedom. If $|t_0|>t_{\alpha/2,\ nA+nB-2}$, where $t_{\alpha/2,\ nA+nB-2}$ is the upper $\alpha/2$ percentage point of the t distribution with $n_A+n_B-2$ degrees of freedom, the null hypothesis will be rejected and concluded that the means of the results of the performance test differ (D. C. MONTGOMERY, Design and analysis of experiments, 8th Ed., john Wiley and Sons).
The values of $t_0$ is 4.18 And $t_{0.05/2,\ 22}=2.074$, so the null hypothesis can be rejected and conclude that the results of the performance differ (level of confidence=95%).

Additional Examples of Capsules Made by Methods in Accordance with the Disclosure Example 3

A first oil solution, which was the initiator solution, was formed by mixing Fragrance Oil (57.95% wt), Isopropyl myristate (41.39% wt) 2,2'-Azobis(2,4-dimethylvaleronitrile) (Vazo 52, 0.40% wt), and 2,2'-Azobis(2-methylbutyronitrile (Vazo-67 0.26% wt) at 20° C. The resulting solution was a transparent liquid.
A second oil solution, which was the monomer solution, was formed by mixing Fragrance Oil (64.77% wt), tertiarybutylaminoethyl methacrylate (0.86% wt), 2-carboxyethyl acrylate (0.69% wt), and Sartomer CN975 (hexafunctional aromatic urethane-acrylate oligomer, 33.68% wt). The second solution was then added to the first oil solution. The proportion of the first oil solution to second oil solution was 2.60 to 1 by total weight. The combined oils were mixed at 25° C. for an additional 10 minutes to form the dispersed phase.
The continuous phase was an aqueous solution containing Selvol 540 (5% wt), NaOH (0.07% wt), and 4,4'-Azobis(4-cyanovaleric acid) (0.37% wt) in water.
The emulsification was prepared by using oscillatory membrane emulsification rig supplied by Micropore. The membrane device consisted of a membrane which is laser drilled, stainless steel film laser welded and mounted vertically on a membrane shaft. The membrane shaft was inserted into the membrane housing and coupled to an oscillatory motor. The continuous phase was pumped into gap between the membrane shaft and the housing using a gear pump (ISMATEC, Micropump 0.32 ml/rev). The dispersed phase was injected, using gear pumps (ISMATEC, Micropump 0.017 ml/rev) from the top of the membrane shaft towards the back part of the membrane. The disperse phase permeated through the pores of the membrane to the continuous phase, in upwards movement to the collection vessel, injected by using a gear pump (ISMATEC, Micropump 0.32 ml/rev). The membrane had pores with 7 μm diameters, with the pores arranged in a hexagonal array and adjacent pores spaced 75 μm, as measured by the distance between the centers of the pores.
The flux of disperse phase though the membrane was 2.2 m$^3$/(m$^2$ of membrane open area*h) and the mass flow rate of the continuous phase was adjusted to achieve a ratio of continuous phase to disperse phase of 2.2. Both flow rates were measured by using Coriolis mass flowmeters (Bronkhorst, m14), placed between the pumps and the membrane device. The membrane shaft was oscillating at a frequency of 30 Hz and 3 mm of amplitude of oscillation. Once a liter of the emulsion is collected in a jacketed vessel, it was mixed gently at 200 rpm and its temperature was raised to 60° C. in 15 min. Then, the temperature was held at 60° C. for 45 minutes, the temperature was increased to 75° C. in 30 minutes, held at 75° C. for 4 hours, heated to 90° C. in 30 minutes and held at 90° C. for 8 hours. The batch was then allowed to cool to room temperature.
The mean size in volume of population of capsules obtained was 28.3 μm and the capsules had a coefficient of variation of diameter based on volume percent of 20.4%.

Example 4

A first oil solution, which was the initiator solution, was formed by mixing Fragrance Oil (44.85 wt %), Isopropyl myristate (54.2 wt %), 2,2'-Azobis(2,4-dimethylvaleronitrile) (Vazo 52, 0.58 wt %), and 2,2'-Azobis(2-methylbutyronitrile (Vazo-67 0.38 wt %), at 20° C. A second oil solution, which was the monomer solution, was formed by mixing Fragrance Oil (81.34 wt %), and Sartomer CN975 (hexafunctional aromatic urethane-acrylate oligomer, 18.66 wt %) at 20° C. The first oil solution and the second oil solution were then pumped using two gear pumps (IS- MATEC, micropump 0.32 ml/rev) at a proportion of 1:1 by weight to form the disperse phase before entering into the membrane shaft.

A continuous phase (aqueous solution) was prepared containing Selvol 540 (1.78 wt %), NaOH (0.07 wt %) and 4,4'-Azobis(4-cyanovaleric acid) (Vazo 68WSP, 0.37 wt %) in water. The continuous phase was pumped across the second surface of the membrane by using a Tuthill GDS pump.

The emulsification was prepared using an oscillatory membrane emulsification rig. The membrane device included a laser-drilled membrane, which had a stainless steel film laser welded and mounted vertically on a membrane shaft (supplied by Micropore). The membrane had pores having a diameter of 7 μm, with the pores being arranged in a hexagonal array and adjacent pores spaced a distances of 40 μm as measured from pore center to pore center. The membrane shaft was inserted into the membrane housing and coupled to an oscillatory motor. The continuous phase was pumped in the gap between the membrane shaft and the housing. The dispersed phase was injected from the top of the membrane shaft towards the back part of the membrane. The disperse phase permeated through the pores of the membrane to the continuous phase, forming an emulsion that exited the emulsification chamber to be collected in a collection vessel.

The flux of disperse phase though the membrane was 24.9 $m^3/(m^2$ of membrane open area*h) and the mass flow rate of the continuous phase was adjusted to achieve a ratio of continuous phase to dispersed phase of 1.5. Both flow rates were measured by using Coriolis mass flowmeters (Bronkhorst, m14), placed between the pumps and the membrane device. The membrane shaft was oscillated at a frequency of 30 Hz and 12.9 mm of amplitude of oscillation.

Once a liter of the emulsion was collected in a jacketed vessel, polymerization was initiated to form the capsules. Polymerization was initiated by mixing the emulsion gently at 200 rpm and the temperature was raised to 60° C. over a 15 minute ramp period. The temperature was then held at 60° C. for 45 minutes. The temperature was then increased to 75° C. over a 30 minute ramp period, and subsequently held at 75° C. for 4 hours. Finally the temperature was raised to 90° C. over a 30 minute ramp period, and held at 90° C. for 8 hours. The batch was then allowed to cool to room temperature.

The resulting capsules had mean size in volume of 24.9 μm and the capsules had a coefficient of variation of diameter based on the volume percent of 23%.

Example 5

An oil solution was made by mixing Fragrance Oil (97.19% wt), tertiarybutylaminoethyl methacrylate (0.07% wt), 2-carboxyethyl acrylate (0.06% wt), and Sartomer CN975 (hexafunctional aromatic urethane-acrylate oligomer, 2.68% wt) at 20° C. The resulting solution was a transparent liquid. Then, 2,2'-Azobis(2,4-dimethylvaleronitrile) (Vazo 52, 0.41% wt), and 2,2'-Azobis(2-methylbutyronitrile) (Vazo-67 0.27% wt), were added and the resultant liquid was mixed at 20° C. The resulting mixture remained a transparent liquid. Lastly, Isopropyl myristate (29.89% wt) is added. The combined oils were mixed at 25° C. for an additional 10 minutes to form the dispersed phase.

The continuous phase was prepared as an aqueous solution containing Selvol 540 (2% wt), NaOH (0.07% wt) and 4,4'-Azobis(4-cyanovaleric acid) (0.37% wt) in water.

The emulsification was prepared by using oscillatory membrane emulsification rig supplied by Micropore. The membrane device consisted of a membrane which is laser drilled Stainless steel film laser welded and mounted vertically on a membrane shaft. The membrane shaft was inserted into the membrane housing and couple to an oscillatory motor. The gap between the membrane shaft and the housing was where the continuous phase was pumped. The dispersed phase was injected, by using gear pumps (ISMATEC, Micropump 0.017 ml/rev) from the top of the membrane shaft towards the back part of the membrane. The disperse phase permeate through the pores of the membrane to the continuous phase, in upwards movement to the collection vessel, injected by using a gear pump (ISMATEC, Micropump 0.32 ml/rev).

The flux of disperse phase though the membrane was 65.6 $m^3/(m^2$ of membrane open area*h) and the mass flow rate of the continuous phase was adjusted to achieve a ratio of continuous phase to disperse phase of 1.5. Both flow rates were measured by using Coriolis mass flowmeters (Bronkhorst, m14), placed between the pumps and the membrane device. The membrane shaft was oscillating at a frequency of 30 Hz and 3 mm of amplitude of oscillation.

Once a liter of the emulsion was collected in a jacketed vessel, it was mixed gently at 200 rpm and its temperature was raised to 60° C. in 15 min. Then, the temperature was held at 60° C. for 45 minutes, the temperature was increased to 75° C. in 30 minutes, held at 75° C. for 4 hours, heated to 90° C. in 30 minutes and held at 90° C. for 8 hours. The batch was then allowed to cool to room temperature.

The mean size in volume of population of capsules obtained was 28.8 μm and the capsules had a coefficient of variation of diameter based on the volume percent of 22.7%.

Example 6

An oil solution was made by mixing Fragrance Oil (92.97% wt), tertiarybutylaminoethyl methacrylate (0.17% wt), 2-carboxyethyl acrylate (0.14% wt), and Sartomer CN975 (hexafunctional aromatic urethane-acrylate oligomer, 6.72% wt) at 20° C. The resulting solution was a transparent liquid. Then, 2,2'-Azobis(2,4-dimethylvaleronitrile) (Vazo 52, 0.41% wt), and 2,2'-Azobis(2-methylbutyronitrile) (Vazo-67 0.27% wt) were added and the resultant liquid was mixed at 20° C. The resulting solution remained a transparent liquid. Lastly, Isopropyl myristate (29.89% wt) is added and mixed at 25° C. for an additional 10 minutes to form the dispersed phase.

The continuous phase was formed as an aqueous solution containing Selvol 540 (2% wt), NaOH (0.07% wt) and 4,4'-Azobis(4-cyanovaleric acid) (0.37% wt) in water The emulsification was prepared by using oscillatory membrane emulsification rig supplied by Micropore. The membrane device included a membrane which was laser drilled stainless steel film laser welded and mounted vertically on a membrane shaft. The membrane shaft was inserted into the membrane housing and couple to an oscillatory motor. The continuous phase was pumped into the gap between the membrane shaft and the housing using a gear pump (ISMATEC, Micropump 0.32 ml/rev). The dispersed phase was injected, using gear pumps (ISMATEC, Micropump 0.017 ml/rev), from the top of the membrane shaft towards the back part of the membrane. The disperse phase permeated through the pores of the membrane to the continuous phase, in upwards movement to the collection vessel, injected by using a gear pump (ISMATEC, Micropump 0.32 ml/rev). The membrane had pores with 7 μm diameters, which were arranged in a hexagonal array and with adjacent pores spaced 75 µm as measured by the distance between the centers of the pores.

The flux of disperse phase though the membrane was 2.2 m³/(m² of membrane open area*h) and the mass flow rate of the continuous phase was adjusted to achieve a ratio of continuous phase to disperse phase of 2.2. Both flow rates were measured by using Coriolis mass flowmeters (Bronkhorst, m14), placed between the pumps and the membrane device.

Once a liter of the emulsion was collected in a jacketed vessel, it was mixed gently at 200 rpm and its temperature was raised to 60° C. in 15 min. Then, the temperature was held at 60° C. for 45 minutes, the temperature was increased to 75° C. in 30 minutes, held at 75° C. for 4 hours, heated to 90° C. in 30 minutes and held at 90° C. for 8 hours. The batch was then allowed to cool to room temperature.

The mean size in volume of population of capsules obtained was 24.0 um and the capsules had a coefficient of variation of diameter based on the volume percent of 18.7%.

Example 7

An oil solution was made by mixing a Fragrance Oil (96% wt), and Sartomer CN975 (hexafunctional aromatic urethane-acrylate oligomer, 4% wt) at 20° C. to get a transparent liquid.

Separately, a second oil solution was made by mixing a Fragrance Oil (39.84%), Isopropyl myristate (60% wt) and 2,2'-Azobis(2-methylbutyronitrile (Vazo-67 0.16% wt) at 20° C. to get a transparent liquid.

The two oil solutions were pumped using two gear pumps (ISMATEC, micropump 0.32 ml/rev) at a proportion of 1:1 in weight, forming the disperse phase when mixed before entering into the membrane shaft.

An aqueous solution (continuous phase) was prepared by mixing Selvol 540 (2% wt), NaOH (0.07% wt) and 4,4'-Azobis(4-cyanovaleric acid) (0.37% wt) in water. The continuous phase was pumped by using a Tuthill GDS pump.

The emulsification was prepared by using oscillatory membrane emulsification rig. The membrane device consisted of a membrane which is laser drilled Stainless steel film laser welded and mounted vertically on a membrane shaft (supplied by Micropore). The membrane shaft was inserted into the membrane housing and coupled to an oscillatory motor. The gap between the membrane shaft and the housing was where the continuous phase is pumped. The dispersed phase was injected from the top of the membrane shaft towards the back part of the membrane. The disperse phase permeated through the pores of the membrane to the continuous phase, forming an emulsion that exited the emulsification chamber and collected in a collection vessel.

The membrane included pores of 7 µm in diameter in a hexagonal array and a distance between the centers of the pores of 40 µm.

The flux of disperse phase though the membrane was 85.4 m³/(m² of membrane open area*h) and the mass flow rate of the continuous phase was adjusted to achieve a ratio of continuous phase to disperse phase of 1.5. Both flow rates were measured by using Coriolis mass flowmeters (Bronkhorst, m14), placed between the pumps and the membrane device. The membrane shaft was oscillating at a frequency of 30 Hz and 12.9 mm of amplitude of oscillation.

Once a liter of the emulsion was collected in a jacketed vessel, it was mixed gently at 200 rpm and its temperature was raised to 60° C. in 15 min. Then, the temperature was held at 60° C. for 45 minutes, the temperature was increased to 75° C. in 30 minutes, held at 75° C. for 4 hours, heated to 90° C. in 30 minutes and held at 90° C. for 8 hours. The batch was then allowed to cool to room temperature.

The mean size in volume of population of capsules obtained was 53.1 µm and the capsules had a coefficient of variation of diameter based on the volume percent of 38.4%.

Example 8

An oil solution was made by mixing Fragrance Oil (96.26% wt), and Sartomer CN975 (hexafunctional aromatic urethane-acrylate oligomer, 3.74% wt) at 20° C. to get a transparent liquid.

Separately, a second oil solution was made by mixing a Fragrance Oil (39.29%), Isopropyl myristate (59.78% wt) and 2,2'-Azobis(2-methylbutyronitrile (Vazo-67 0.94% wt) at 20° C. to get a transparent liquid.

The two oil solutions were pumped using two gear pumps (ISMATEC, micropump 0.32 ml/rev) at a proportion of 1:1 in weight, forming the disperse phase when mixed before entering into the membrane shaft.

An aqueous solution (Continuous phase) is prepared containing Selvol 540 (2% wt), NaOH (0.07% wt) and 4,4'-Azobis(4-cyanovaleric acid) (0.37% wt) in water. The continuous phase was pumped by using a Tuthill GDS pump.

The emulsification was prepared by using oscillatory membrane emulsification rig. The membrane device consisted of a membrane which was laser drilled Stainless steel film laser welded and mounted vertically on a membrane shaft (supplied by Micropore). The membrane shaft was inserted into the membrane housing and couple to an oscillatory motor. The gap between the membrane shaft and the housing was where the continuous phase is pumped. The dispersed phase was injected from the top of the membrane shaft towards the back part of the membrane. The disperse phase permeated through the pores of the membrane to the continuous phase, forming an emulsion that exited the emulsification chamber to be collected in a collection vessel.

The membrane included pores of 7 um in diameter in a hexagonal array and a distance between the centers of the pores of 40 um.

The flux of disperse phase though the membrane was 26.7 m³/(m² of membrane open area*h) and the mass flow rate of the continuous phase was adjusted to achieve a ratio of continuous phase to disperse phase of 1.5. Both flow rates were measured by using Coriolis mass flowmeters (Bronkhorst, m14), placed between the pumps and the membrane device. The membrane shaft was oscillating at a frequency of 30 Hz and 12.9 mm of amplitude of oscillation.

Once a liter of the emulsion was collected in a jacketed vessel, it was mixed gently at 200 rpm and its temperature was raised to 60° C. in 15 min. Then, the temperature was held at 60° C. for 45 minutes, the temperature was increased to 75° C. in 30 minutes, held at 75° C. for 4 hours, heated to 90° C. in 30 minutes and held at 90° C. for 8 hours. The batch was then allowed to cool to room temperature.

The mean size in volume of population of capsules obtained was 27.7 µm and the capsules had a coefficient of variation of diameter based on the volume percent of 16.1%.

Example 9

An oil solution was made by mixing a Fragrance Oil (44.86%, wt), Isopropyl Myristate (54.95%, wt), Vazo 52 (0.11%, wt), and Vazo 67 (0.07%, wt) at room temperature (RT) until the mixture was homogeneous.

A second oil solution was made by mixing a Fragrance Oil (96%, wt), and Sartomer CN975 (hexafunctional aromatic urethane-acrylate oligomer, 4.00%, wt) at RT until the mixture was homogeneous.

An aqueous solution (continuous phase) was prepared by adding Selvol 540 (2% wt) to reverse osmosis (RO) water and heating to 90° C. for 4 h with agitation followed by cooling to RT.

The membrane device consisted of a membrane which was laser drilled Stainless steel film laser welded and mounted vertically on a membrane manifold, the membrane manifold was introduced into the emulsification chamber and coupled to an oscillatory motor. The gap between the membrane manifold and the housing was where the continuous phase was pumped. The dispersed phase was injected from the top of the membrane manifold and distributed towards the back part of the membrane. The disperse phase permeated through the pores of the membrane to the continuous phase, forming an emulsion that exited the emulsification chamber to be collected in a collection vessel.

The membrane included pores of 7 μm in diameter in a hexagonal array and a distance between the centers of the pores of 40 μm.

The oscillation had a displacement of 8 mm and a frequency of 36 Hz. The two oil phases were mixed inline using a static mixer at a ratio of 53.5:46.5. The flux of disperse phase through the membrane was 37.4 m$^3$/(m$^2$ of membrane open area*h). The mass flow rate of the continuous phase was adjusted to achieve a ratio of continuous phase to disperse phase of 1.5.

A kilogram of the emulsion was collected in a jacketed vessel and mixed at 50 rpm using a paddle blade and overhead mechanical stirrer. The temperature was raised to 60° C. at 2.5° C./min and held for 45 min. Then the temperature was raised to 75° C. at 0.5° C./min and held for 240 min. Then temperature was raised to 90° C. at 0.5° C./min and held for 480 min. Finally, the batch was cooled to RT while maintaining stirring.

The final product was a suspension of encapsulated perfume capsules in PVOH solution. Additional components may be added as needed such as stabilizers and/or preservatives.

The mean size in volume of the population of capsules obtained was 29.7 μm and the capsules had a coefficient of variation of diameter based on the volume percent of 31.3%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A population of capsules comprising a plurality of capsules, the capsules comprising:
   a core comprising a benefit agent; and
   a polymeric shell surrounding the core,
wherein the population of capsules comprises a delta fracture strength percentage of about 15% to about 230% and a mean shell thickness of about 20 nm to about 400 nm.

2. The population of capsules of claim 1, wherein the population of capsules has a mean effective volumetric core-shell ratio of at least about 90 to 10.

3. The population of capsules of claim 1, wherein the population of capsules has a mean effective volumetric core-shell ratio of at least 95 to 5.

4. The population of capsules of claim 1, wherein the benefit agent comprises one or more perfume compositions, perfume raw materials, sanitization agents, disinfecting agents, antiviral agents, fabric refreshing and freshness extending agents, chlorine bleach odor control agents, dye fixatives, dyes, optical brighteners, color restoration/rejuvenation, enzymes, anti-foaming agents, fabric comfort agents, skin care agents, lubricants, waxes, hydrocarbons, malodor reducing agents, odor-controlling materials, fertilizers, nutrients, and herbicides.

5. The population of capsules of claim 4, wherein the benefit agent comprises a perfume composition.

6. The population of capsules of claim 5, wherein the perfume composition comprises a combination of perfume raw materials comprising by weight based on the total weight of the perfume composition (1) about 2.5% to about 30% of first perfume raw materials having a log P of less than 3.0, and a boiling point of less than 250° C.; (2) about 5% to about 30% of second perfume raw materials having a log P of less than or equal to 3.0 and a boiling point greater than or equal to 250° C.; (3) about 35% to about 60 of third perfume raw materials having a log P of greater than 3.0 and a boiling point less than 250° C.; and (4) about 10% to about 45% of fourth perfume raw materials having a log P greater than 3.0 and a boiling point greater than 250° C.

7. The population of capsules of claim 1, wherein the core comprises about 10 wt % or more benefit agent based on the total weight of the core.

8. The population of capsules of claim 1, wherein the benefit agent has a mean log P of greater than or equal to 1.

9. The population of capsules of claim 1, wherein the core further comprises an oil admixed with the benefit agent.

10. The population of capsules of claim 1, wherein the polymeric shell comprises a homopolymer, a copolymer, or a cross-linked polymer, and combinations thereof.

11. The population of capsules of claim 1, wherein the polymer comprises one or more of polyacrylate, polymethacrylate, melamine formaldehyde, polyurea, polyurethane, polyamide, polyvinyl alcohol, chitosan, gelatin, polysaccharides, and gums.

12. The population of capsules of claim 1, wherein the capsules have a mean fracture strength at the median size of the population (d50) of about 0.2 MPa to about 30 MPa.

13. The population of capsules of claim 1, wherein the capsules have a mean diameter of about 1 μm to about 100 μm.

14. A population of capsules comprising a plurality of capsules, the capsules comprising:
a core comprising a benefit agent; and
a polymeric shell surrounding the core,
wherein the population of capsules has a number population diameter coefficient of variation of about 10% to about 100% and a mean shell thickness of about 20 nm to about 400 nm.

15. The population of capsules of claim 14, wherein the population of capsules has a mean effective volumetric core-shell ratio of at least about 90 to 10.

16. The population of capsules of claim 14, wherein the population of capsules has a mean effective volumetric core-shell ratio of at least 95 to 5.

17. The population of capsules of claim 14, wherein the benefit agent comprises one or more perfume compositions, perfume raw materials, sanitization agents, disinfecting agents, antiviral agents, fabric refreshing agents and freshness extending agents, chlorine bleach odor control agents, dye fixatives, dyes, optical brighteners, color restoration/rejuvenation, enzymes, anti-foaming agents, fabric comfort agents, skin care agents, lubricants, waxes, hydrocarbons, malodor reducing agents, odor-controlling materials, fertilizers, nutrients, and herbicides.

18. The population of capsules of claim 17, wherein the benefit agent comprises a perfume composition.

19. The population of capsules of claim 18, wherein the perfume composition comprises a combination of perfume raw materials comprising by weight based on the total weight of the perfume composition (1) about 2.5% to about 30% of first perfume raw materials having a log P of less than 3.0, and a boiling point of less than 250° C.; (2) about 5% to about 30% of second perfume raw materials having a log P of less than or equal to 3.0 and a boiling point greater than or equal to 250° C.; (3) about 35% to about 60 of third perfume raw materials having a log P of greater than 3.0 and a boiling point less than 250° C.; and (4) about 10% to about 45% of fourth perfume raw materials having a log P greater than 3.0 and a boiling point greater than 250° C.

20. The population of capsules of claim 14, wherein the core comprises about 10 wt % or more benefit agent based on the total weight of the core.

21. The population of capsules of claim 14, wherein the benefit agent has a mean log P of greater than or equal to 1.

22. The population of capsules of claim 14, wherein the core further comprises an oil admixed with the benefit agent.

23. The population of capsules of claim 14, wherein the polymeric shell comprises a homopolymer, a copolymer, or a cross-linked polymer, and combinations thereof.

24. The population of capsules of claim 14, wherein the polymer comprises one or more of polyacrylate, polymethacrylate, melamine formaldehyde, polyurea, polyurethane, polyamide, polyvinyl alcohol, chitosan, gelatin, polysaccharides, and gums.

25. The population of capsules of claim 14, wherein the capsules have a mean fracture strength at the median size of the population (d50) of about 0.2 MPa to about 30 MPa.

26. The population of capsules of claim 14, wherein the capsules have a mean diameter of about 1 μm to about 100 μm.

* * * * *